(12) United States Patent
Weber et al.

(10) Patent No.: US 7,041,634 B2
(45) Date of Patent: May 9, 2006

(54) METHOD OF INHIBITING IMMUNE SYSTEM DESTRUCTION OF TRANSPLANTED VIABLE CELLS

(75) Inventors: Collin J. Weber, Atlanta, GA (US);
Mary K. Hagler, Loganville, GA (US);
Peter S. Linsley, Seattle, WA (US);
Judith A. Kapp, Atlanta, GA (US);
Susan A. Safley, Decatur, GA (US)

(73) Assignees: Emory University, Atlanta, GA (US);
Bristol Myers-Squibb Company, New York, NY (US)

( * ) Notice: Subject to any disclaimer, the term of this patent is extended or adjusted under 35 U.S.C. 154(b) by 0 days.

(21) Appl. No.: 09/049,865

(22) Filed: Mar. 27, 1998

(65) Prior Publication Data

US 2004/0047890 A1 Mar. 11, 2004

Related U.S. Application Data

(63) Continuation of application No. PCT/US96/15577, filed on Sep. 27, 1996.

(60) Provisional application No. 60/004,375, filed on Sep. 27, 1995.

(51) Int. Cl.
*A61K 38/00* (2006.01)
(52) U.S. Cl. ............ 514/2; 424/156.1; 424/137.1; 424/141.1; 424/93.7; 424/812; 530/350
(58) Field of Classification Search ............ 514/2; 424/19, 93.7, 137.1, 141.1, 156.1, 812; 530/350
See application file for complete search history.

(56) References Cited

U.S. PATENT DOCUMENTS

| 4,663,286 A | 5/1987 | Tsang et al. |
| 4,673,566 A * | 6/1987 | Goosen et al. ............ 424/424 |
| 4,696,286 A | 9/1987 | Cochrum |
| 5,334,640 A | 8/1994 | Desai et al. |
| 5,434,131 A | 7/1995 | Linsley et al. |

FOREIGN PATENT DOCUMENTS

| EP | 0613944 A2 * | 7/1994 |
| EP | 0613944 | 9/1994 |
| WO | WO9200092 | 1/1992 |
| WO | WO9300431 | 1/1993 |
| WO | WO9711607 | 4/1997 |

OTHER PUBLICATIONS

Burgess et al. Journal of Cell Biology, 1990, 11 : 2129-2138.*
Lazar et al. Molecular and Cell Biology, 1988, 8: 1247-1252.*
Tao. et al. The Journal of Immunology, 1989, 143(8): 2595-2601.*
Gillies et al. Human Antibodies and Hybridomas, 1990, 1(1): 47-54.*
Stites, DP et al, eds, 1997, Medical Immunology, Appleton & Lange, Stamford, Connecticut, p. 48).*
Lenschow, DJ et al, 1992, Science, 257: 789-792.*
Soon-shiong P et al, 1990, Horm Metab Res Suppl, 25: 215-9.*
Akalin, E et al, 1996, Transplantation, 62(12): 1942-5.*
Padrid PA et al, 1998, Am J Respir Cell Mol Biol, 1844): 453-62.*
Stetlrer, W et al, 1995, J. Immunol, 155 (3): 1165-74.*
Aomatsu, Y. et al. (1994) "Indefinite Graft Survival of Discordant Islet Xenografts in the NOD Mouse With Agarose Microencapsulation and 15-Deoxyspergualin", *Transplantation Proc.*, 26(2):805-06 (Exhibit 7).
Aomatsu, Y. et al., (1995) "Significance of Low Doses of 15-Deoxyspergualin in Agarose-Microencapsulated Discordant Islet Xenotransplantation", *Islet Xenotransplantation*, 292-93 (Exhibit 8).
Auchincloss, H., (1988) "Xenogeneic Transplantation", *Transplantation*, 46(1):1-20 (Exhibit 9).
Blazar, B.R., et al., (1993) "In Vivo Infusion of Soluble CTLA4-Ig Reduces Lethal Graft-Versus-Host Disease (GVHD) Induced Across the major Histocompatibility Complex (MHC) Barrier in Mice", *Blood*, 82(10):456a. 1809 (Exhibit 10).

(Continued)

*Primary Examiner*—Susan Ungar
*Assistant Examiner*—Minh-Tam Davis
(74) *Attorney, Agent, or Firm*—John P. White, Esq.; Cooper & Dunham LLP

(57) ABSTRACT

This invention provides a method of inhibiting viable cells transplanted into a subject from being destroyed by the subject's immune system which comprises: a) containing the viable cells, or tissue comprising the viable cells, prior to transplantation within a device comprising a semipermeable membrane; and b) treating the subject with a substance which inhibits an immune-system costimulation event in an amount effective to inhibit the subject's immune system from responding to said contained cells or tissue. In one embodiment, the substance which inhibits an immune-system costimulation event is CTLA4. Also provided by this invention is a method of treating diabetes in a subject which comprises: a) containing viable insulin-producing cells, or tissue comprising such cells, within a device comprising a semipermeable membrane; b) transplanting an effective amount of such contained viable insulin-producing cells into the subject; and c) treating the subject with an effective amount of a substance which inhibits an immune-system costimulation event.

12 Claims, 56 Drawing Sheets

OTHER PUBLICATIONS de Vos, P. et al., (1994) "Possible Relationship Between Fibrotic Overgrowth of Alginate-Polysine-Alginate Microencapsualted Pancreatic Islets and the Microcapsule Integrity", *Transplantation Proc.*, 26(2):782-83 (Exhibit 11).

Forty, J. et al., (1992) "Hyperacute Rejection of Rabbit Hearts by Human Blood is Mediated by the Alternative Pathway of Complement", *Transplantation Proc.*, 24(2):488-89 (Exhibit 12).

Iwata, H. et al., (1992) "Marked Prolongation of Islet Xenograft Survival (Hamster to Mouse) by Microencapsulation and Administration of 15-Deoxyspergualin", *Transplantation Proc.*, 24(4):1517-18 (Exhibit 13).

Krych, M. et al., (1992) "complement receptors", *Current Opinion in Immunology*, 4(1): 8-13 (Exhibit 14).

Lacy, P., (1993) "Status of islet cell transplantation", *Diabetes Rev.*, 1(1):76-92 (Exhibit 15).

Lafferty, K. et al., (1988) "Circumventing rejection of islet grafts: an overview", In: Van Schilfgaarde, R., and Hardy M. (eds.), Transplantation of the Endocrine Pancreas in Diabetes Medllitus. Elsevier Science Publishers B.V. (Biomedical Division), 279-91 (Exhibit 16).

Lanza, R. et al., (1995) "A Simple Method For Transplanting Discordant Islets Into Rats Using Alginate Gel Spheres", *Transplantation*, 59(10):1485-87 (Exhibit 17).

Lenschow, D. et al., (1992) "Long-Term Survival of Xenogeneic Pancreatic Islet Grafts Induced by CTLAIg", *Science*, 257(5071):789-92 (Exhibit 18).

Mazaheri, R. et al., (1991) "Transplantation of Encapsulated Allogenic Islets Into Diabetic BB/W Rats: Effects of Immunosuppression", *Transplantation*, 51(4):750-54 (Exhibit 19).

Pearson, T.C. et al., (1994) "Transplantation Tolerance Induced by CTLA4-Ig", *Transplantation*, 57(12):1701-06 (Exhibit 20).

Platt, J. et al., (1991) "The Barrier to Xenotranplantation", *Transplantation*, 52(6):937-47 (Exhibit 21).

Platt, J. et al., (1991) "The Role of Natural Antibodies in the Activation of Xenogeneic Endothelial Cells", *Transplantation*, 52(6):1037-43 (Exhibit 22).

Rabinovitch, A. et al., (1990) "Cytotoxic Effects of Cytokines on Human Pancreatic Islet Cells in Monolayer Culture", *J. Clinical Endocrinology & Metabolism*, 71(1):152-56 (Exhibit 23).

Ricker, A. et al., (1986) "Hyperimmune Response to Microencapsulated Xenogeneic Tissue in Non Obese Diabetic Mice", In: *The Immunology of Diabetes Mellitus*, Jaworski, M. (ed.) Elseview, Amsterdam, 193-200 (Exhibit 24).

Ricordi, C. et al., (1987) "Low-temperature culture of human islets of *in vivo* treatment L3T4 antibody produces a marked prolongation of islet human-to-mouse xenograft survival", *Proc. Natl. Acad. Sci. USA*, 84:8080-84 (Exhibit 25).

Soon-Shiong, P. et al., (1992) "Successful Reversal of Spontaneous Diabetes in Dogs by Intraperitoneal Microencapsulated Islets", *Transplantation*, 54(5):769-74 (Exhibit 26).

Weber, C. et al., (1989) "Microencapsualted Dog and Rat Islet Xenografts Into Sterptozotocin-Diabetic and NOD Mice", *Hormone and Metabolic Res.*, Supplement series 25:219-26 (Exhibit 27).

Weber, C. et al., (1990) "The Role of CD4+ Helper T Cells in the Destruction of Microencapsulated Islet Xenografts in NOD Mice", *Transplantation*, 49(2):396-404 (Exhibit 28).

Weber, C. et al., (1990) "Prolonged Functional Survival of Rat-to-NOD Mouse Islet Xenografts by Ultraviolet-B(UV-B) Irradiation Plus Microencapsulation of Donor islets" *Transplantation Proc.*, 2391);764-66 (Exhibit 29).

Weber, C. et al., (1993) "Humoral Reaction to Microencapsulated Rat, Canine, and Porcine islet Xenografts in Spontaneously diabetic NOD Mice", *Transplantatin Proc.*, 25(1):462-63 (Exhibit 30).

Weber, C. et al., (1994) "NOD Mouse Peritoneal Cellular Response to Poly-L-Lysine-Alginate-Microencapsualted Rat Islets", *Transplantation Proc.* 26(3):1116-19 (Exhibit 31).

Dupuy, B., et al. (1991) "Microencapsulation of isolated pituitary cells by polyacrylamide microlatex coagulation on agarose beads", *Biomaterials*, 12 (5) : 493-496. (Exhibit 3).

Hakim, F.T., et al. (1995) "Acute Graft-Versus-Host Reaction can be Aborted by Blockade of Costimulatory Molecules", *J. Immunol.*, 155(4) :1757-1766. (Exhibit 4).

Steurer, W., et al. (1995) "Ex Vivo Coating of Islet Cell Allografts with Murine CTLA4/Fc Promotes Graft Tolerance", *J. Immunol.*, 155(3) : 1165-1174. (Exhibit 5).

* cited by examiner

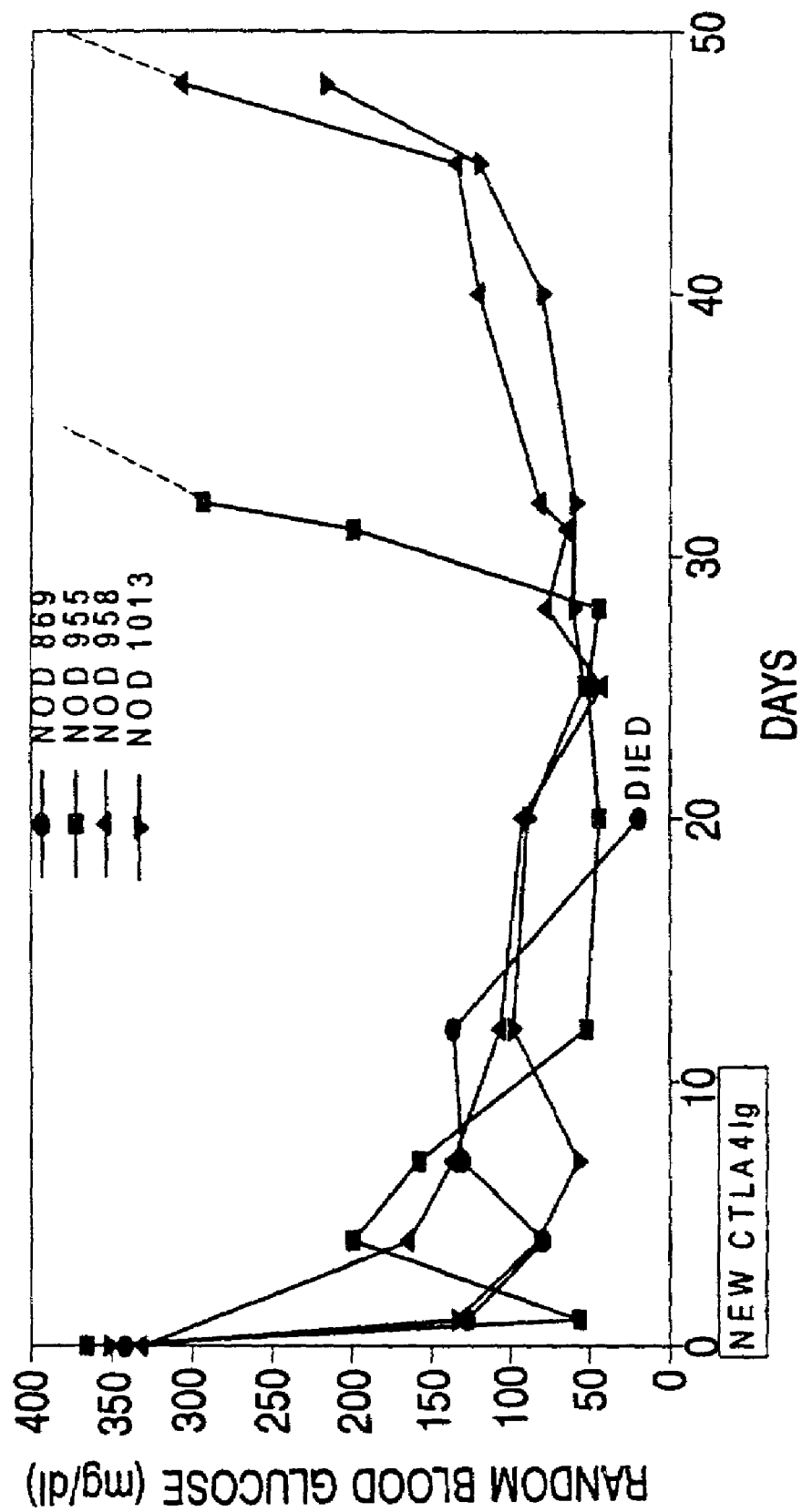

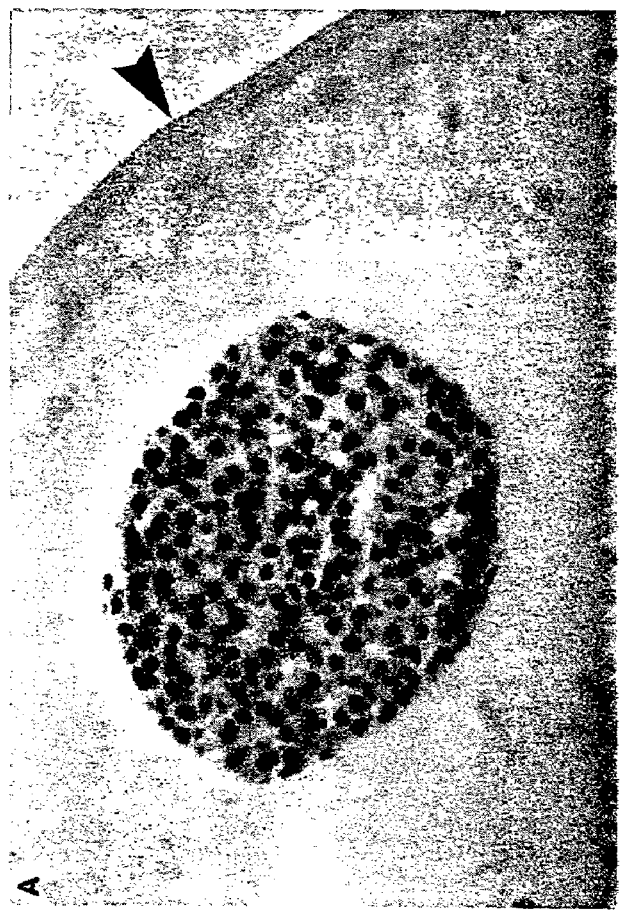
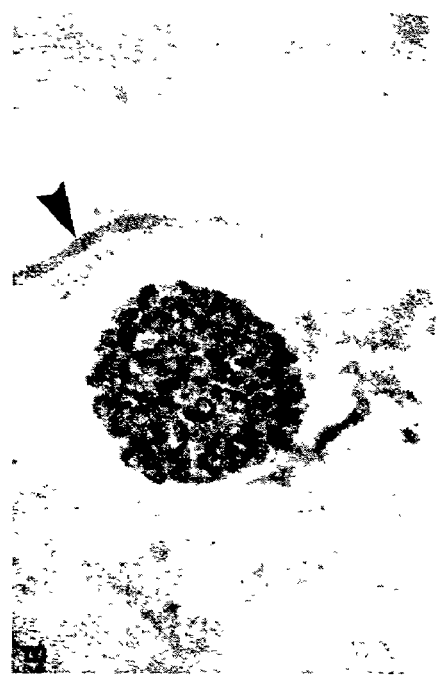
FIG. 28A
FIG. 28B

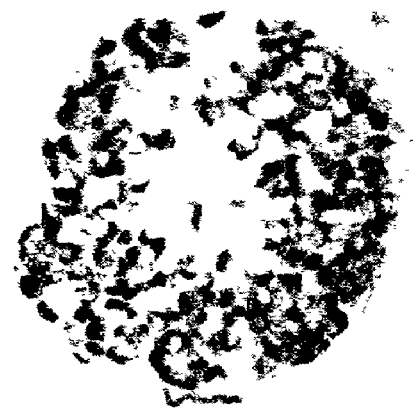
FIG. 29A
FIG. 29B

FIG. 35 Microencapsulated Neonatal Pig Islet Transplants into Diabetic NOD Mice Treated with mutant CTLA4-Ig for 21 Days

FIG. 39A IL-2 present in peritoneal fluid on sac day
Transplanted NODs
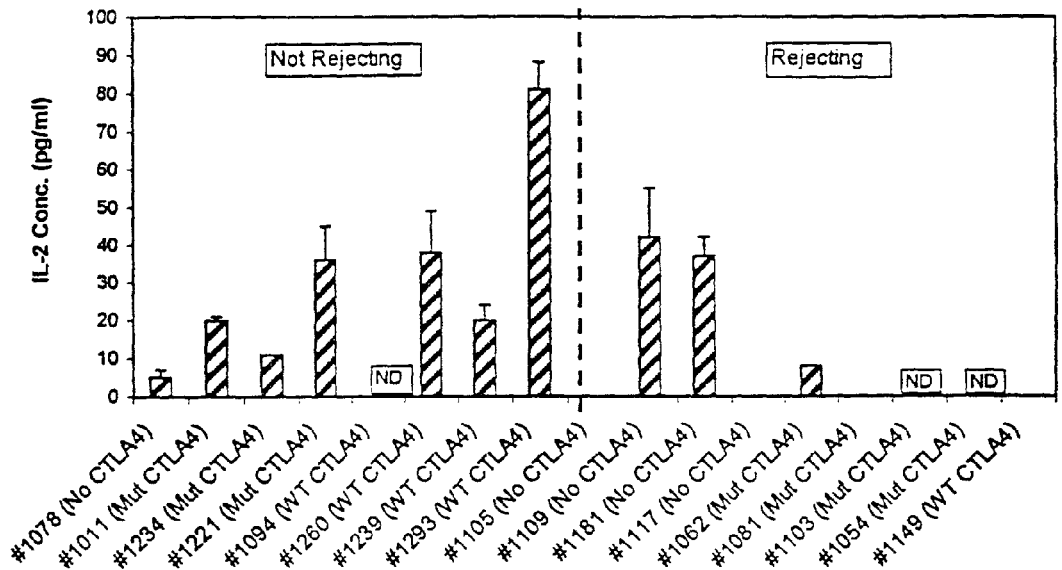
FIG. 39B IL-2 present in peritoneal fluid on sac day
Untransplanted mice
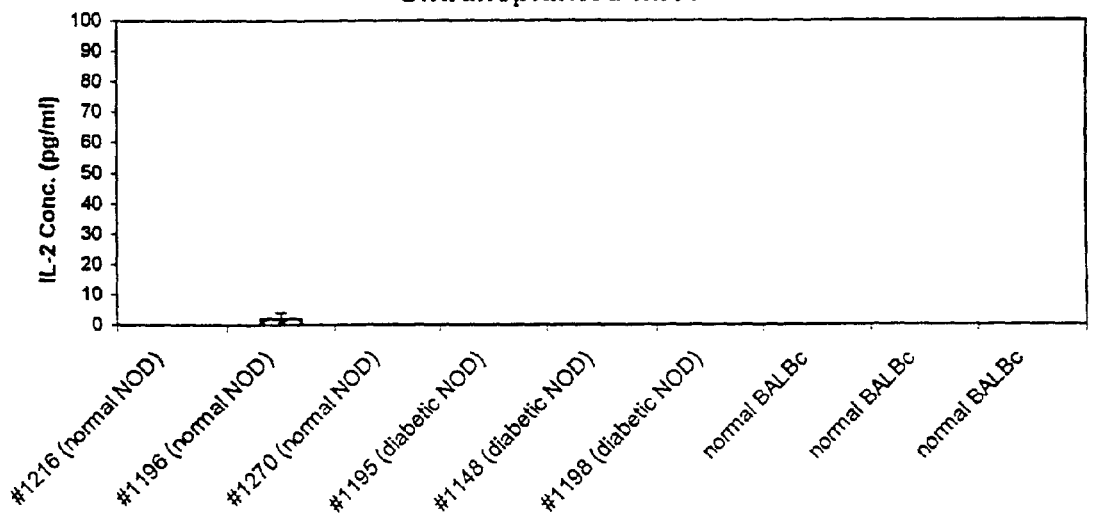

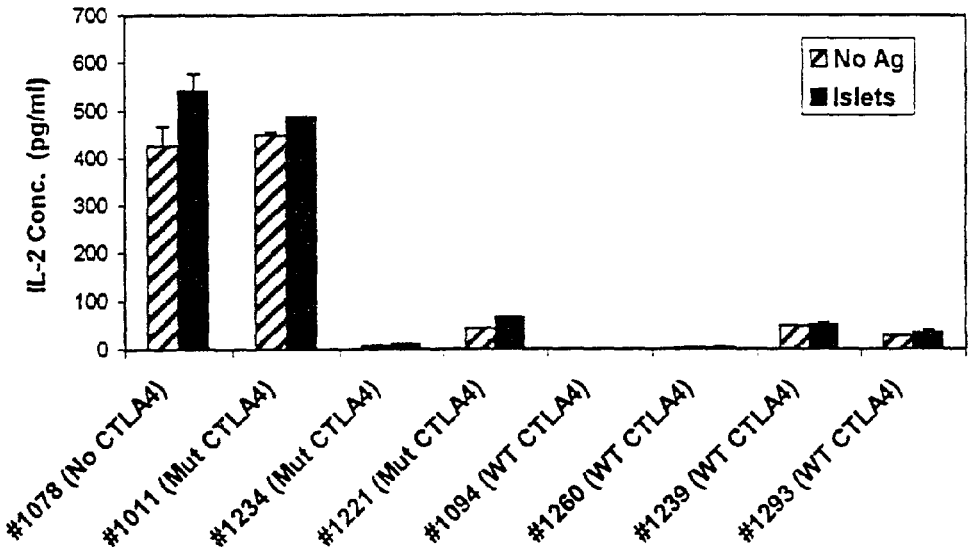
FIG. 40A  IL-2 secreted by SPC cultured with porcine islets
Transplanted NODs - Not Rejecting
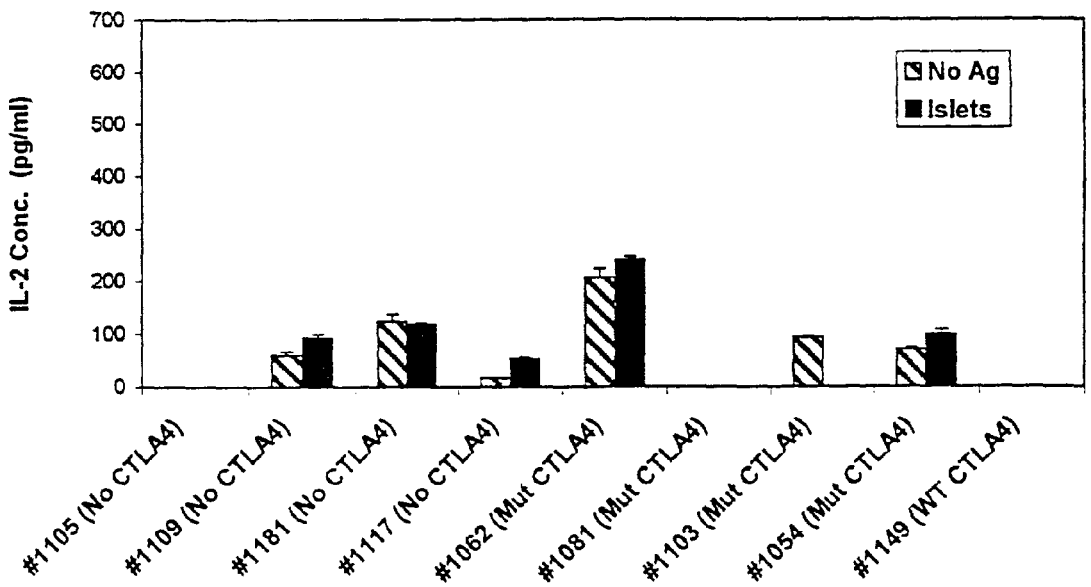
FIG. 40B  IL-2 secreted by SPC cultured with porcine islets
Transplanted NODs - Rejecting

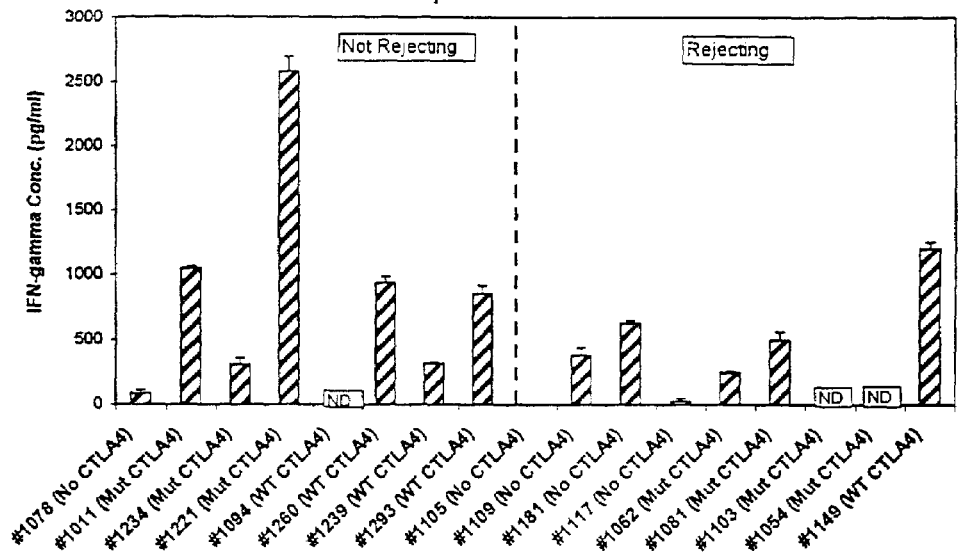
FIG. 41A  IFN-gamma present in peritoneal fluid on sac day Transplanted NODs
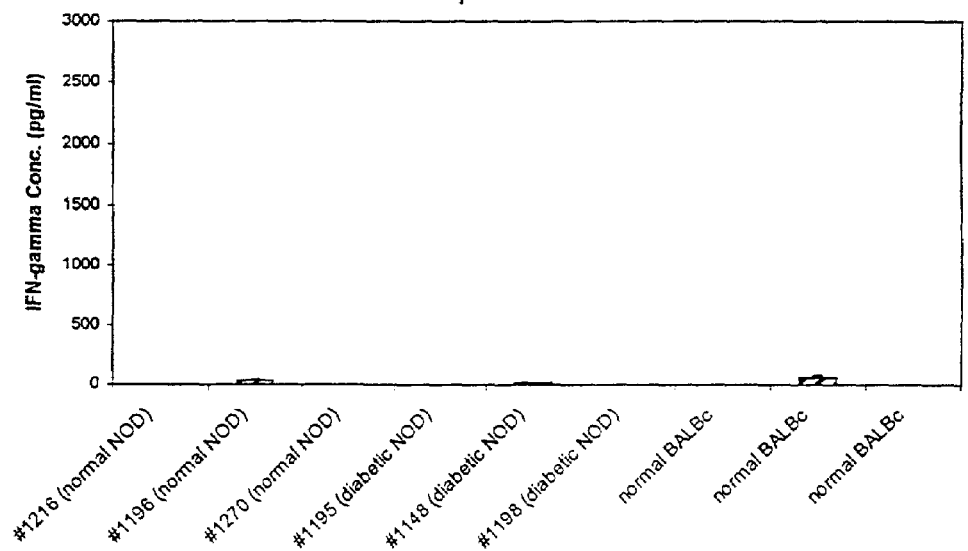
FIG. 41B  IFN-gamma present in peritoneal fluid on sac day Untransplanted mice

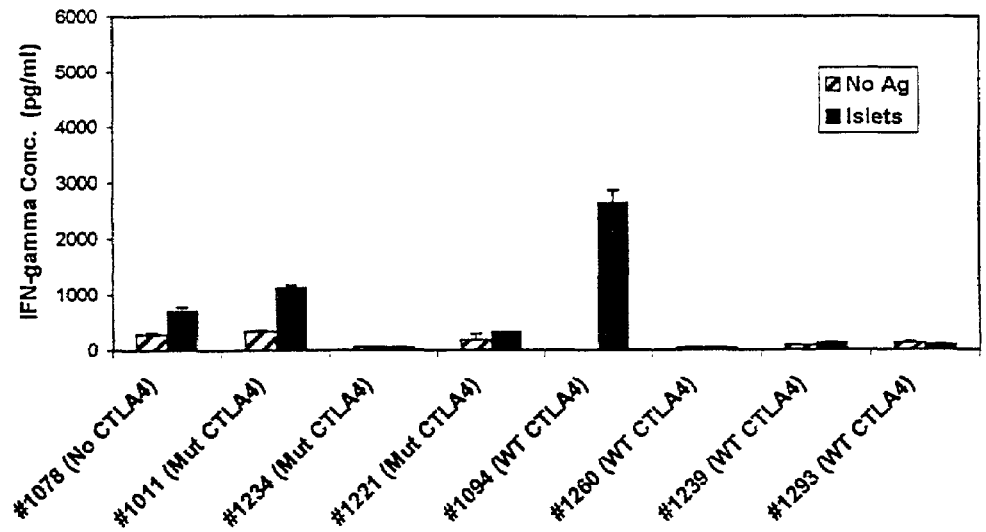
FIG. 42A IFN gamma secreted by SPC cultured with porcine islets
Transplanted NODs - Not Rejecting
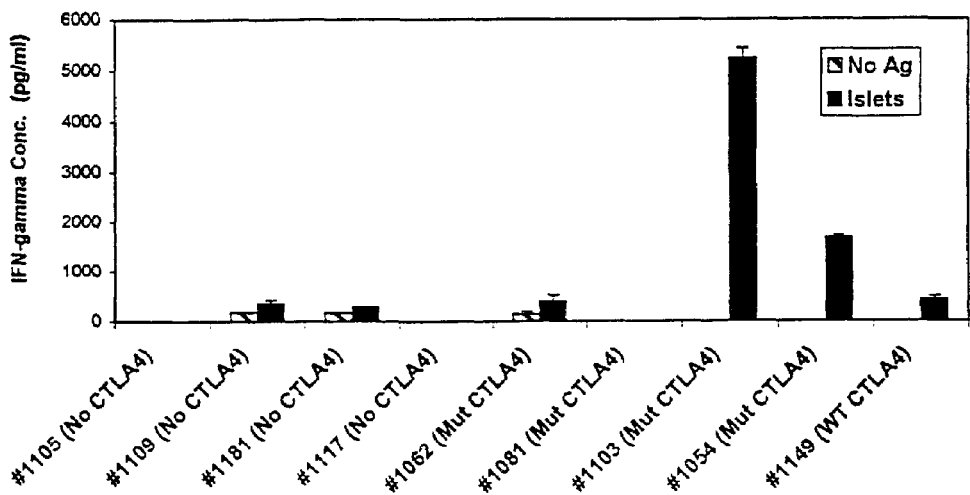
FIG. 42B IFN-gamma secretion by SPC cultured with porcine islets
Transplanted NODs - Rejecting

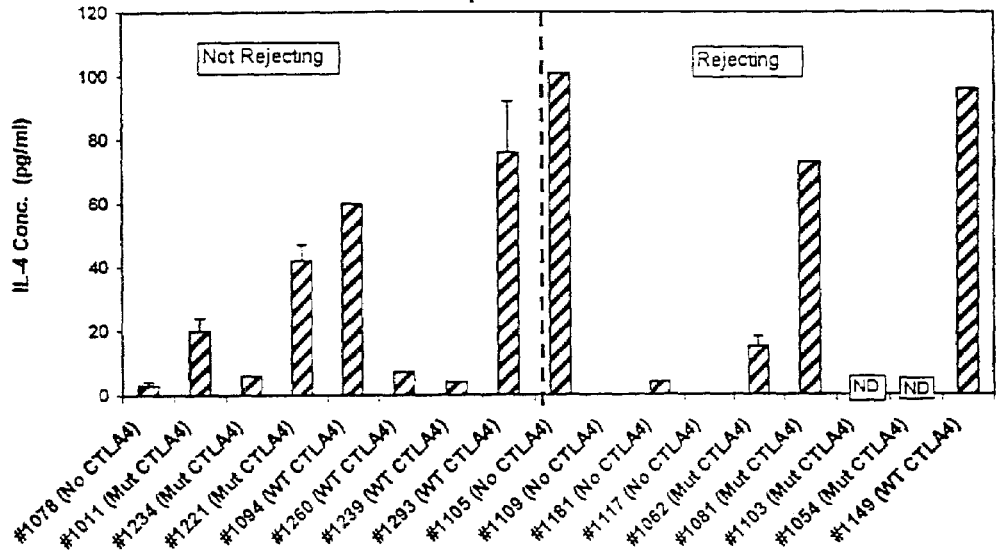
FIG. 43A  IL-4 present in peritoneal fluid on sac day
Transplanted NODs
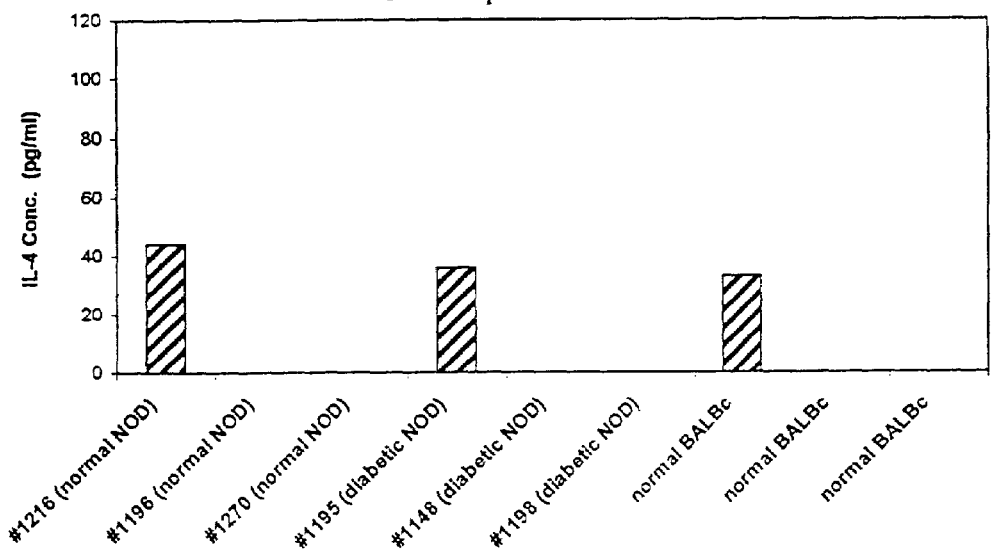
FIG. 43B  IL-4 present in peritoneal fluid on sac day
Untransplanted mice

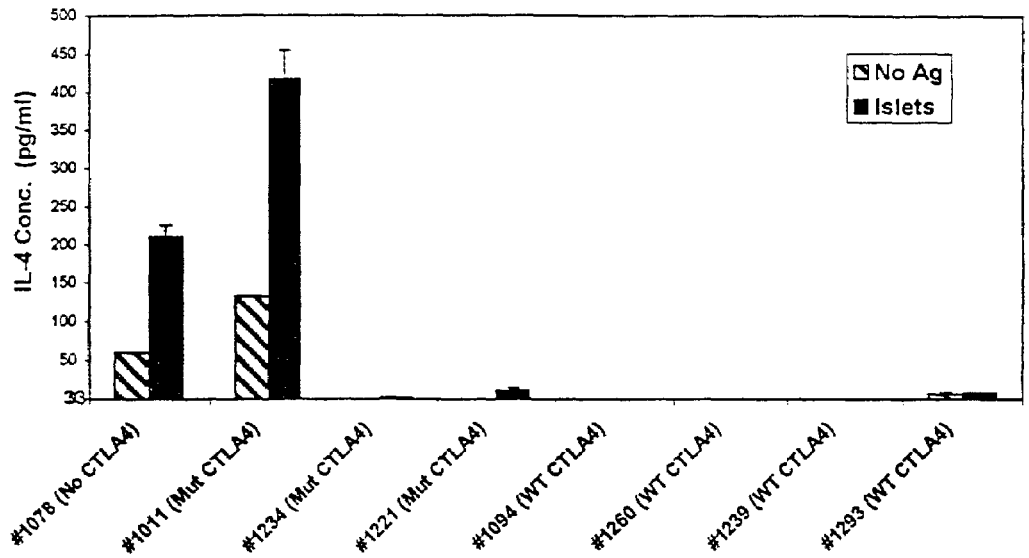
FIG. 44A  IL-4 secreted by SPC cultured with porcine islets
Transplanted NODs - Not Rejecting
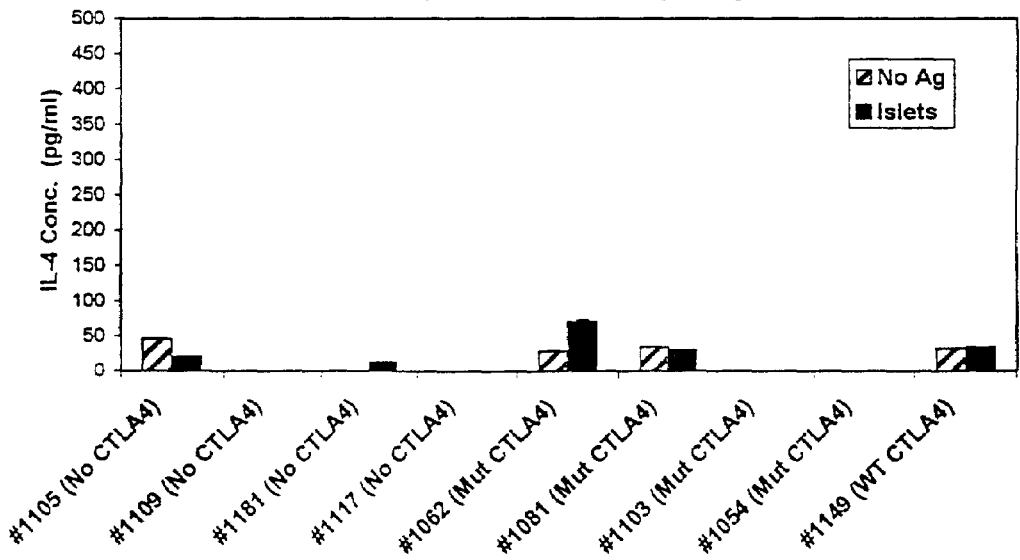
FIG. 44B  IL-4 secreted by SPC cultured with porcine islets
Transplanted NODs - Rejecting

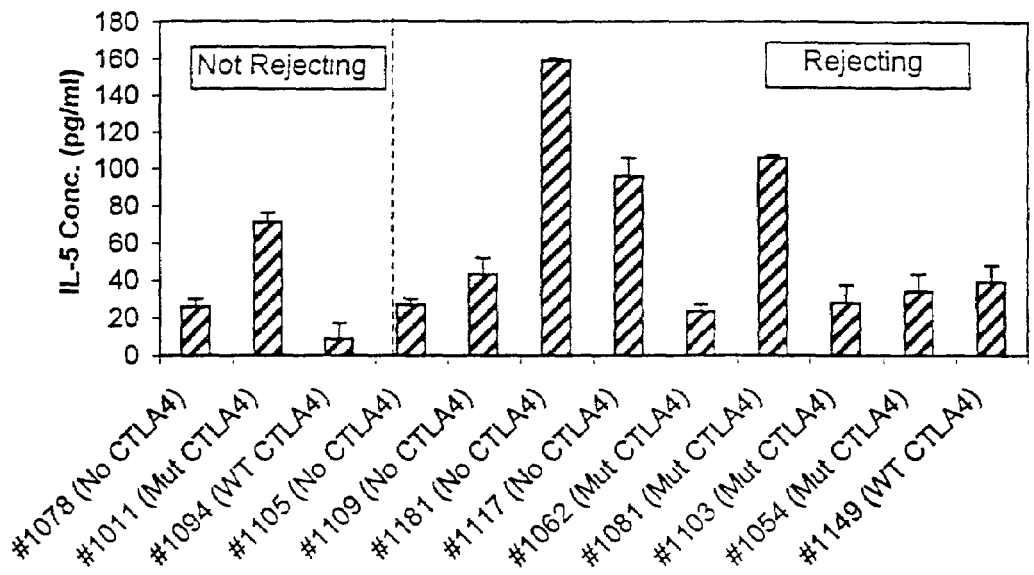
FIG. 45A  IL-5 present in peritoneal fluid on sac day Transplanted NODs
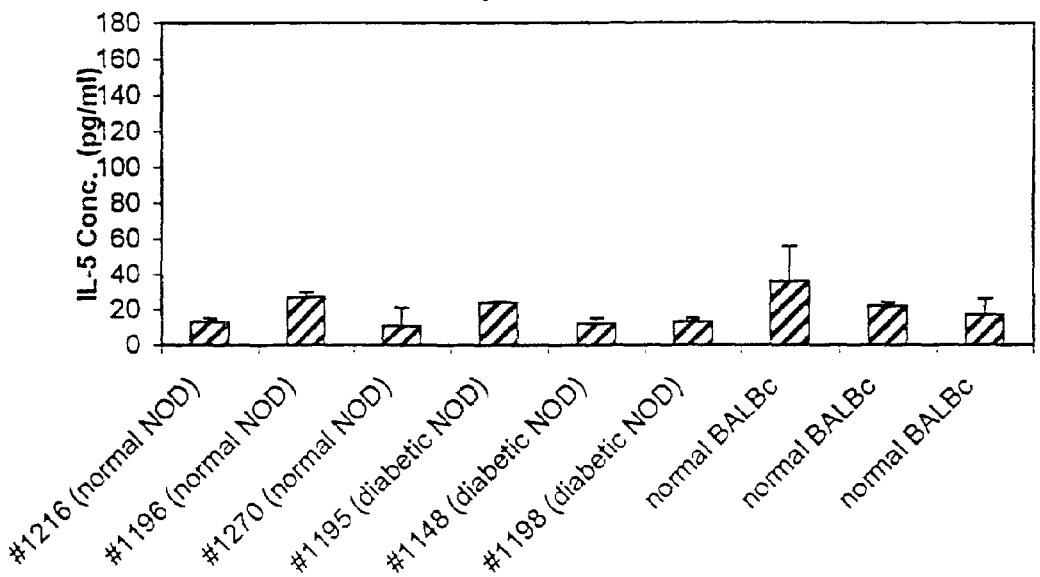
FIG. 45B  IL-5 present in peritoneal fluid on sac day Untransplanted mice

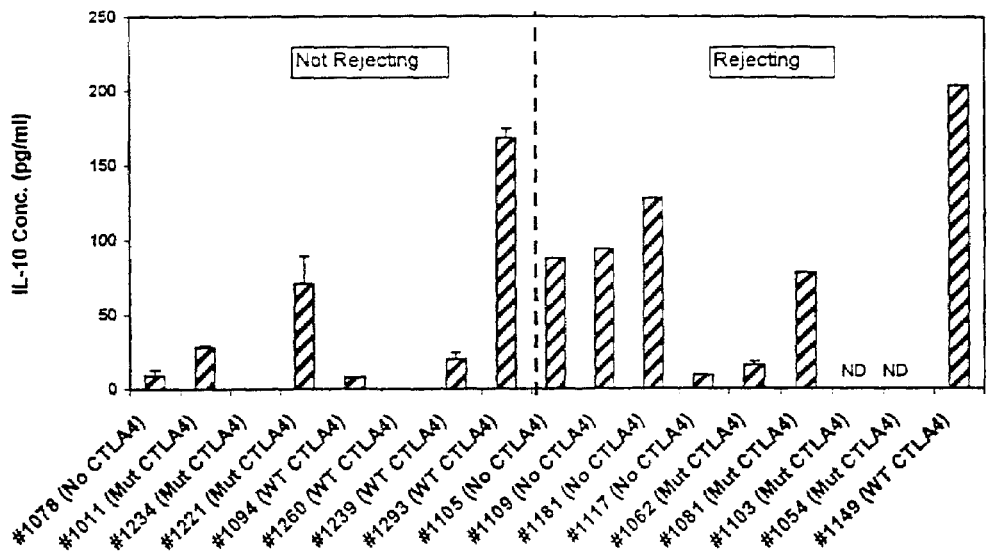
FIG. 46A   IL-10 present in peritoneal fluid on sac day
Transplanted NODs
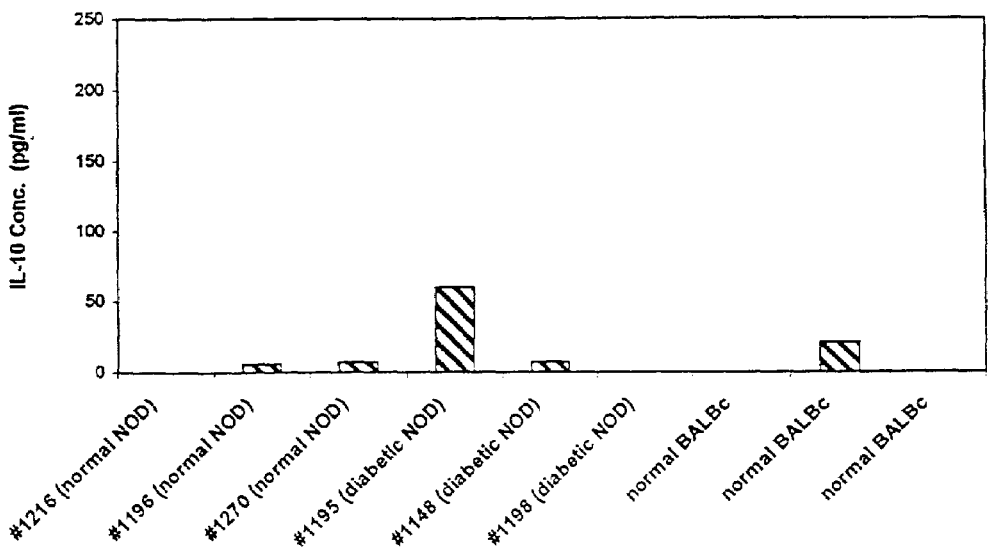
FIG. 46B   IL-10 present in peritoneal fluid on sac day
Untransplanted mice

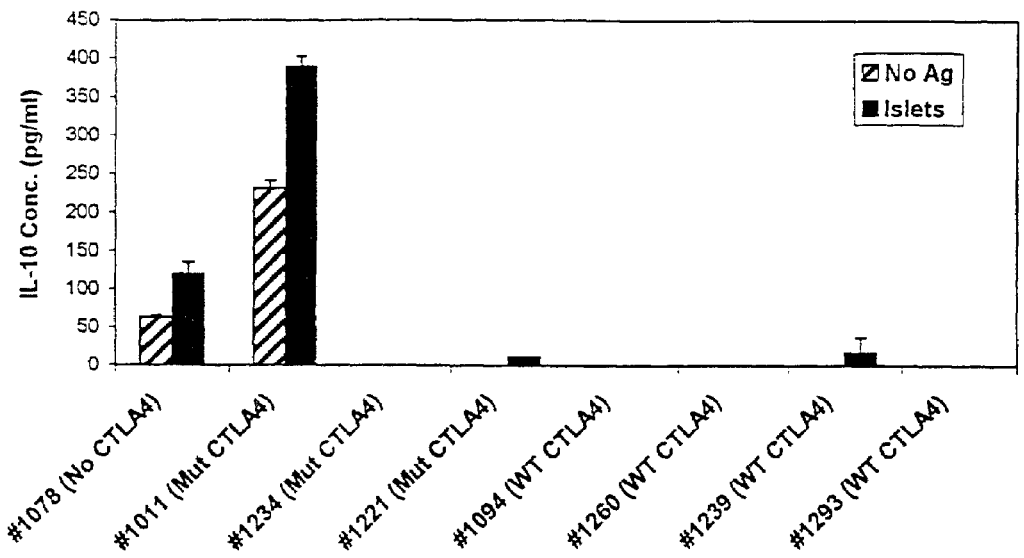
FIG. 47A  IL-10 secreted by SPC cultured with porcine islets
Transplanted NODs - Not Rejecting
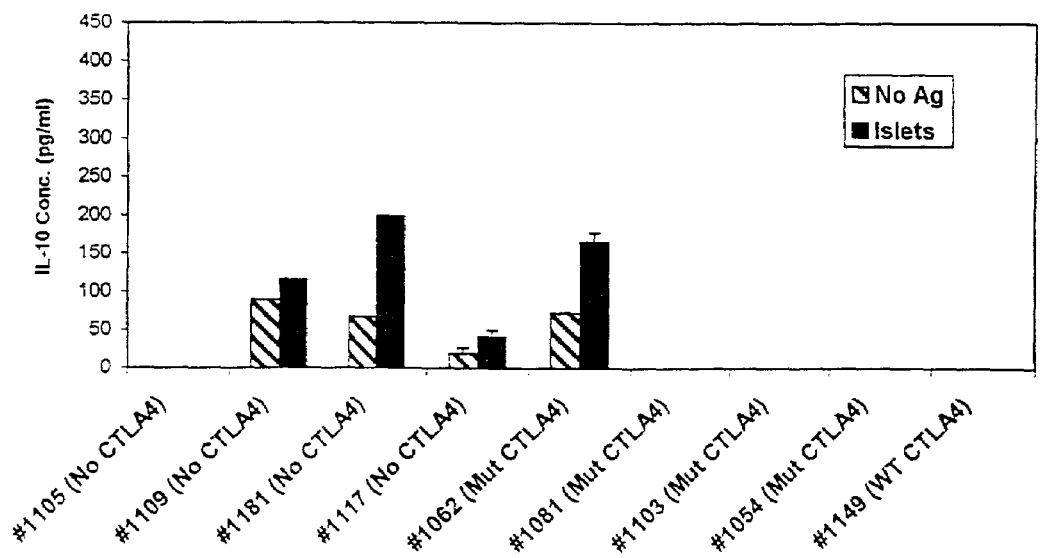
FIG. 47B  IL-10 secreted by SPC cultured with porcine islets
Transplanted NODs - Rejecting

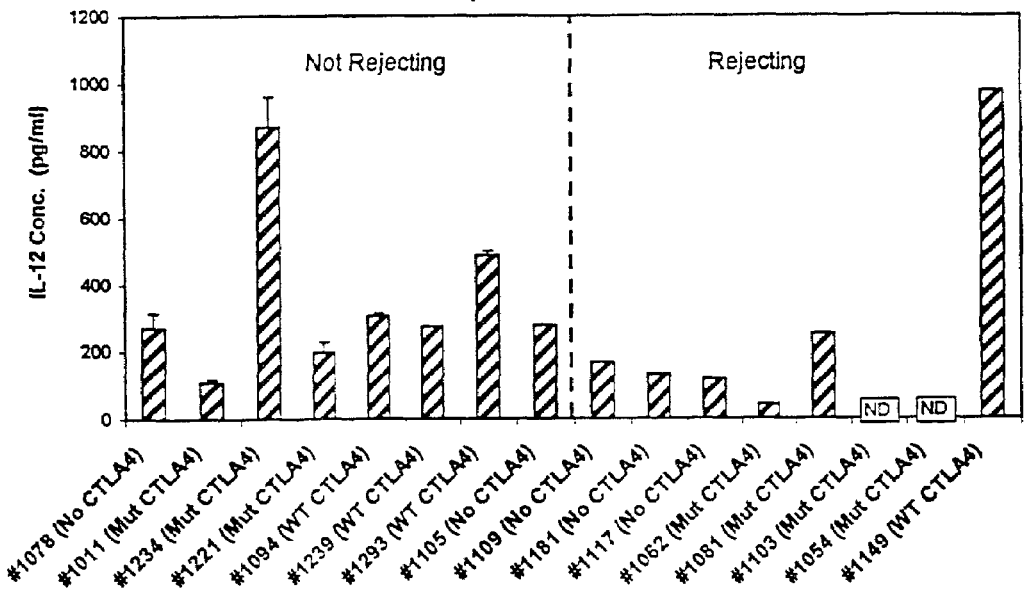
FIG. 48A  IL-12 present in peritoneal fluid on sac day
Transplanted NODs
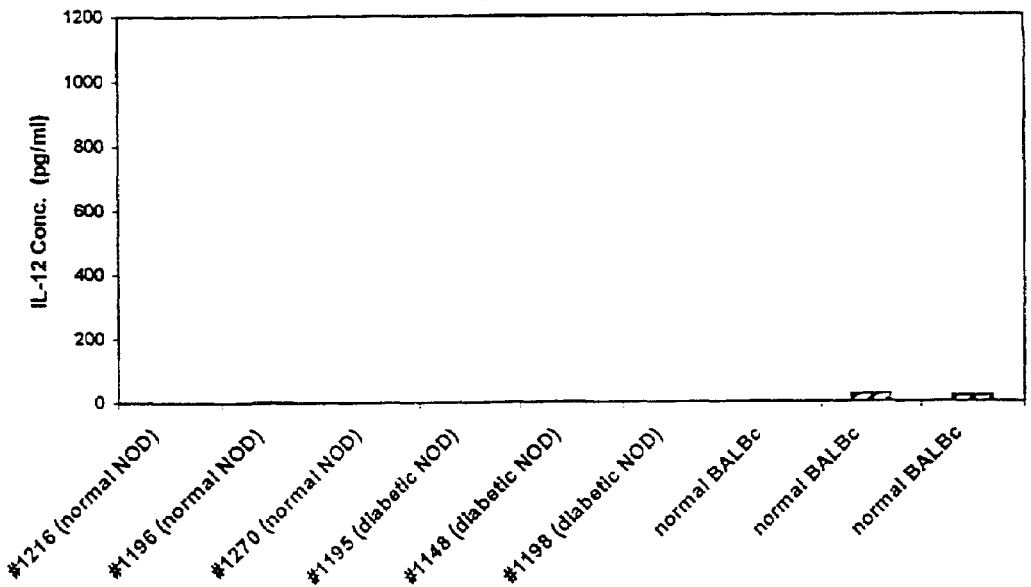
FIG. 48B  IL-12 present in peritoneal fluid on sac day
Untransplanted mice

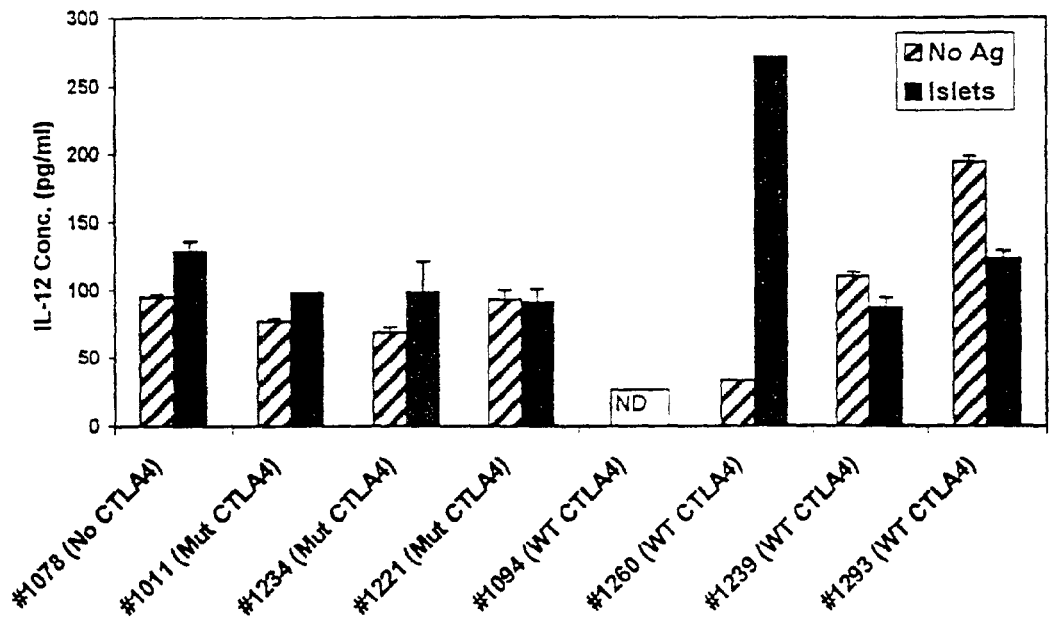
FIG. 49A   IL-12 secreted by SPC cultured with porcine islets
Transplanted NODs - Not Rejecting
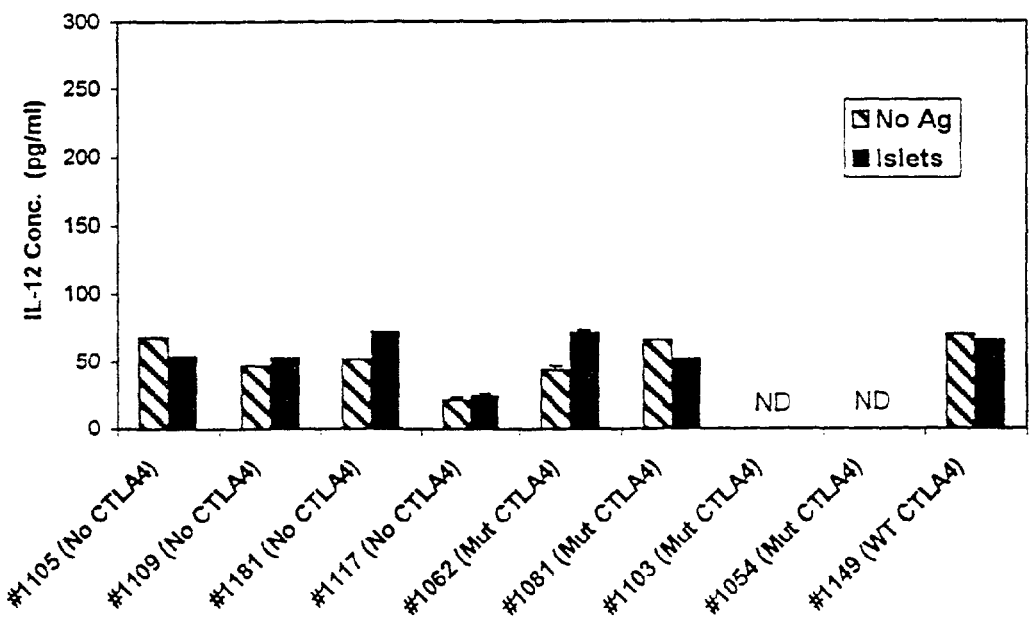
FIG. 49B   IL-12 secreted by SPC cultured with porcine islets
Transplanted NODs - Rejecting

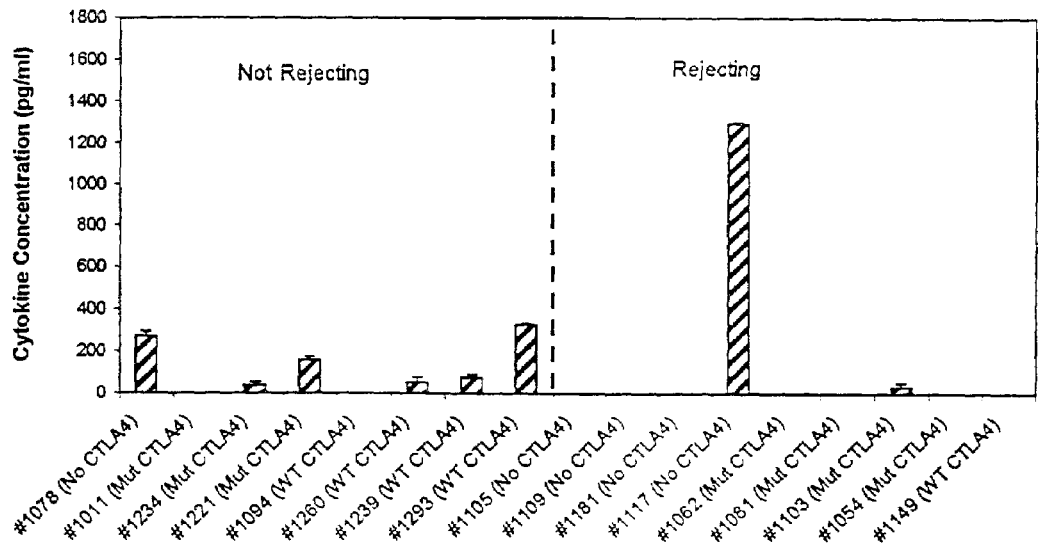
FIG. 50A  TNF alpha present in peritoneal fluid on sac day
Transplanted NODs
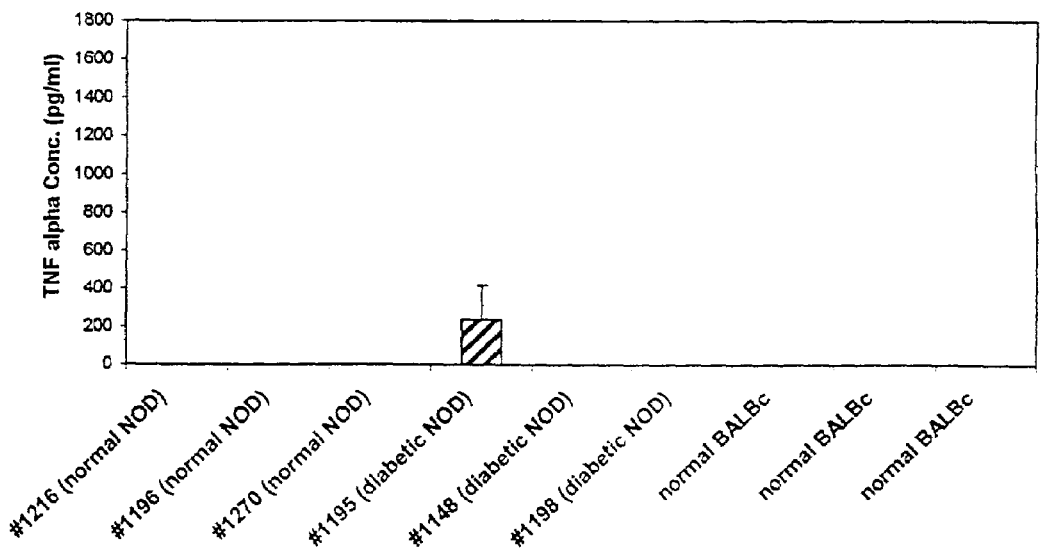
FIG. 50B  TNF alpha present in peritoneal fluid on sac day
Untransplanted NODs FIG. 51A  TNF-α secreted by SPC cultured with porcine islets
Transplanted NODs - Not Rejecting
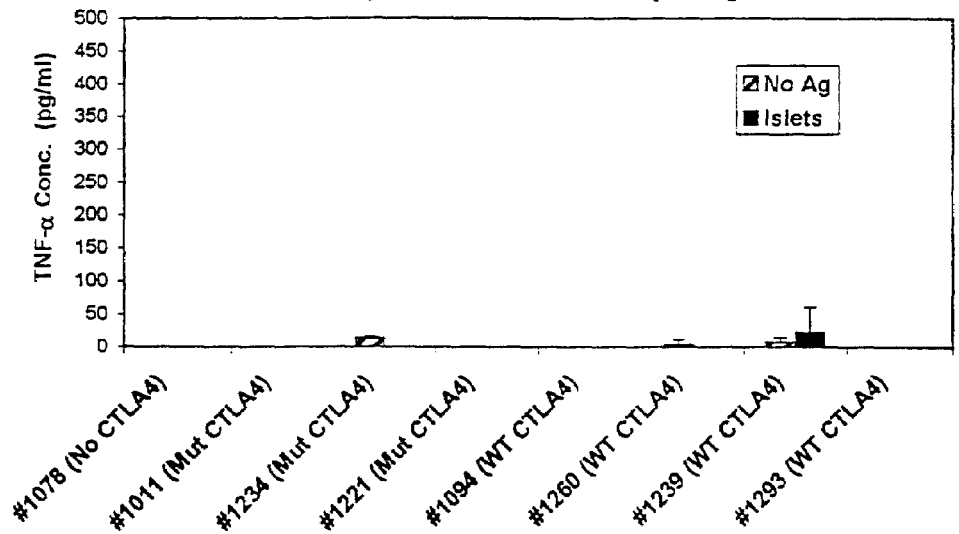
FIG. 51B  TNF-α secreted by SPC cultured with porcine islets
Transplanted NODs - Rejecting
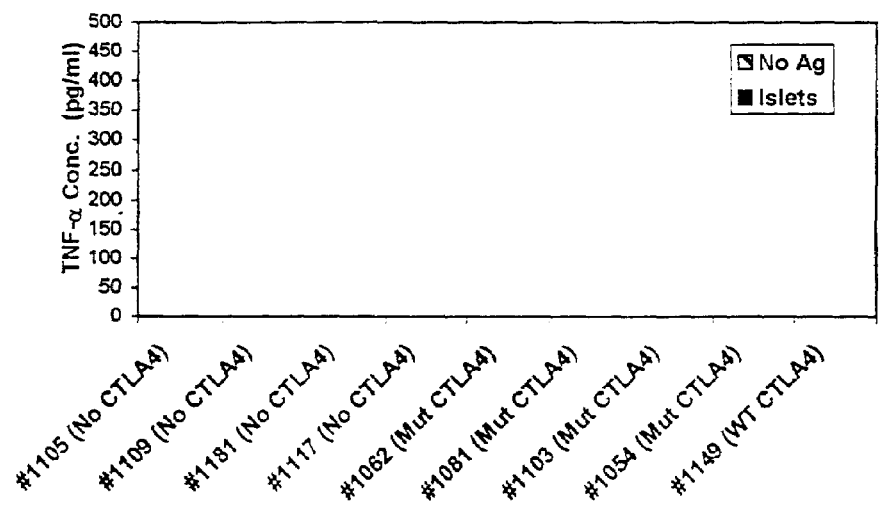

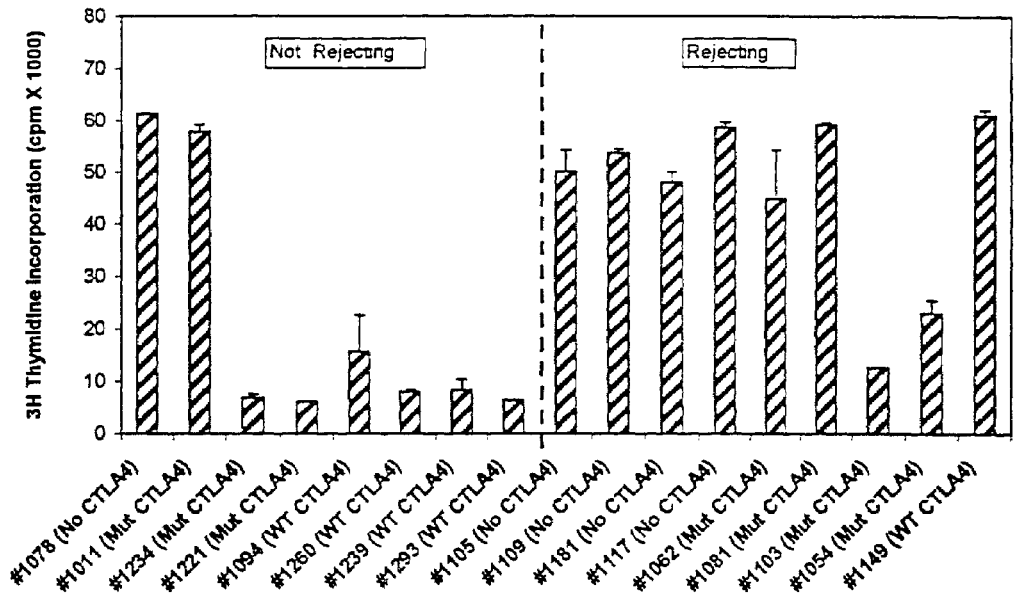
FIG. 52A  TGF beta present in peritoneal fluid on sac day
Transplanted NODs
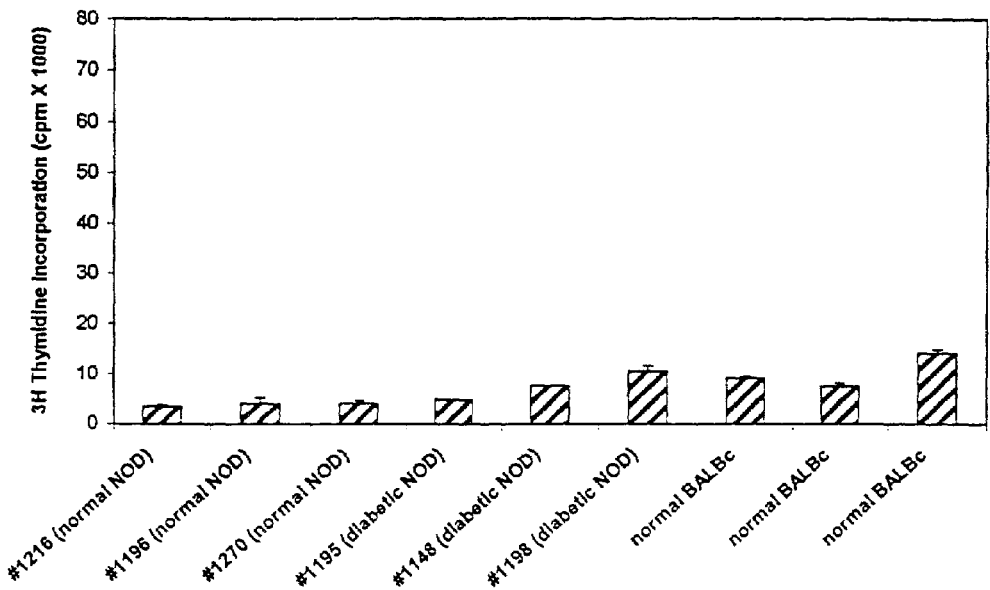
FIG. 52B  TGF beta present in peritoneal fluid on sac day
Untransplanted mice

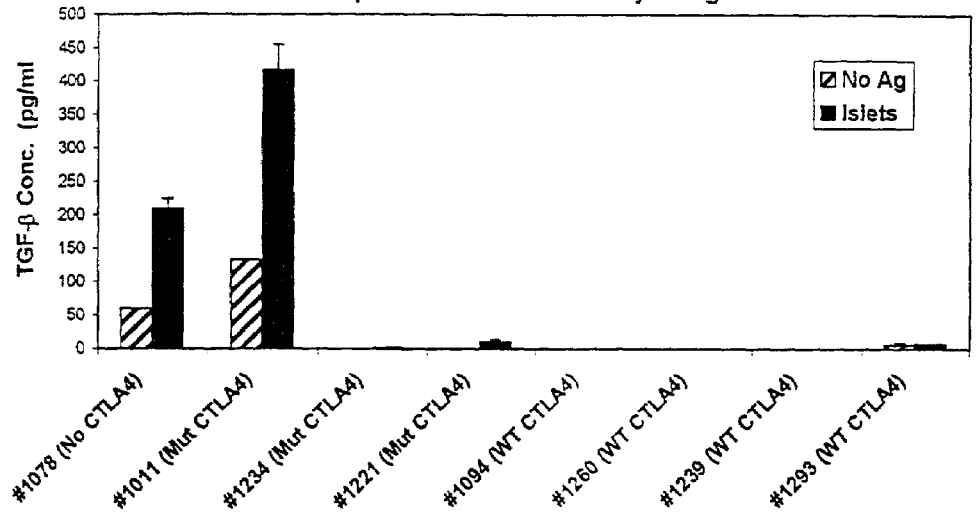
FIG. 53A TGF-β secreted by SPC cultured with porcine islets
Transplanted NODs - Not Rejecting
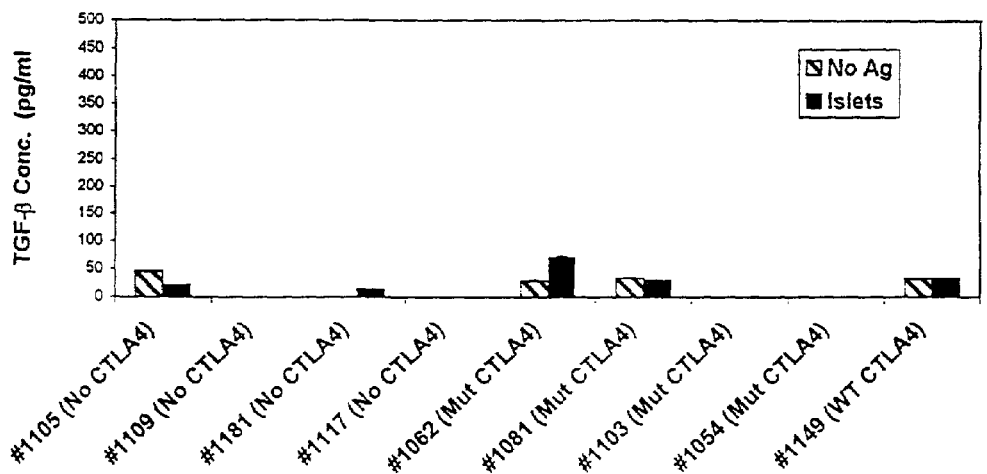
FIG. 53B TGF-β secreted by SPC cultured with porcine islets
Transplanted NODs - Rejecting FIG. 54A  NO2 produced by SPCs cultured with pig islets
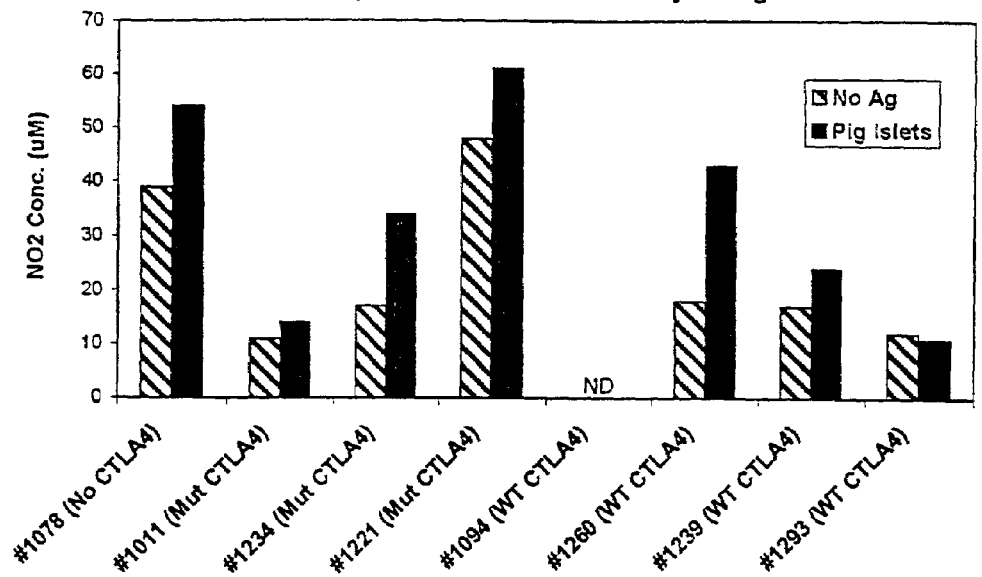
FIG. 54B
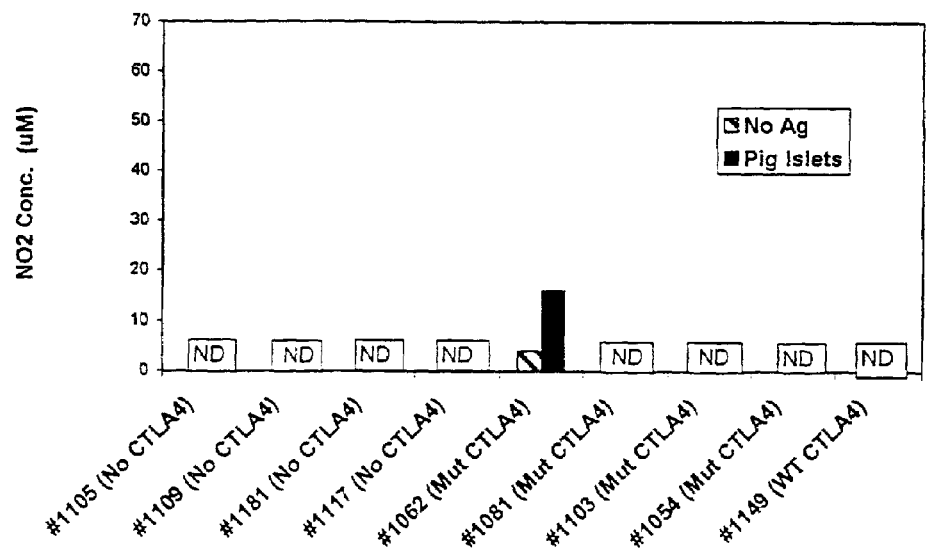

NO2 produced by PECs after 96 hr in culture with original encapsulated porcine islets

FIG. 57A Proliferation of SPC from NOD #1335 to pig islet cells in vitro (Expt 288)
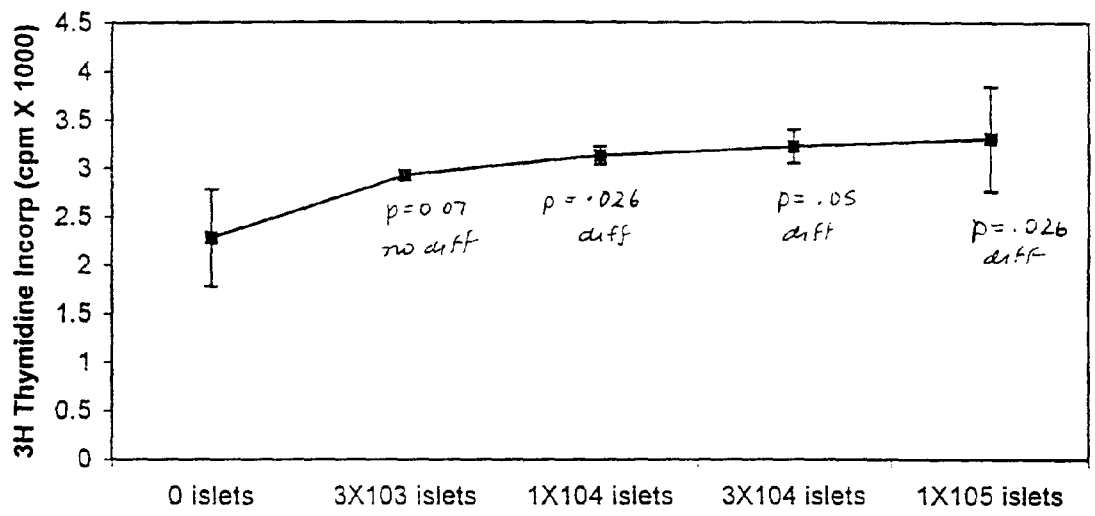
FIG. 57B Proliferation of SPC from NOD #1335 Expt 288
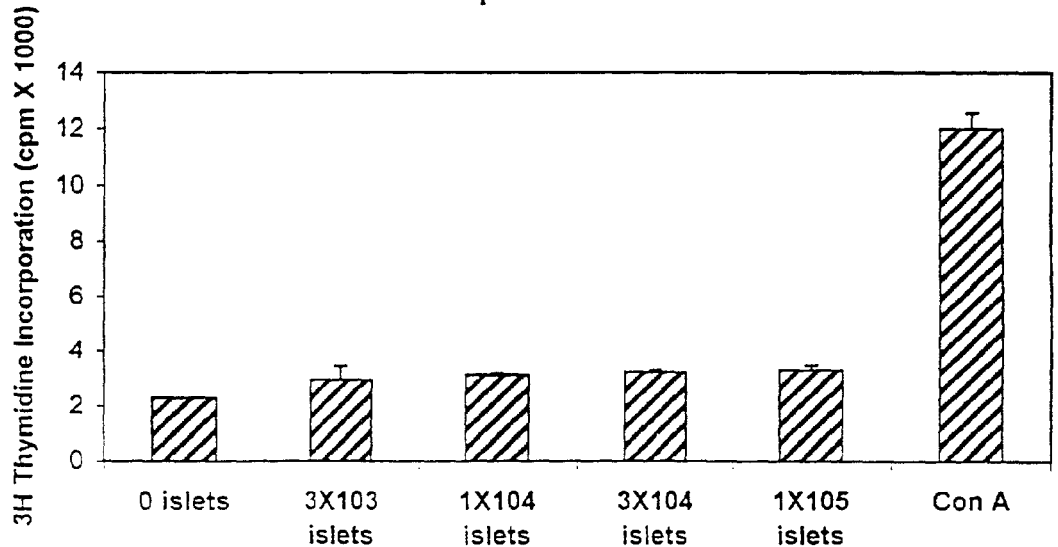

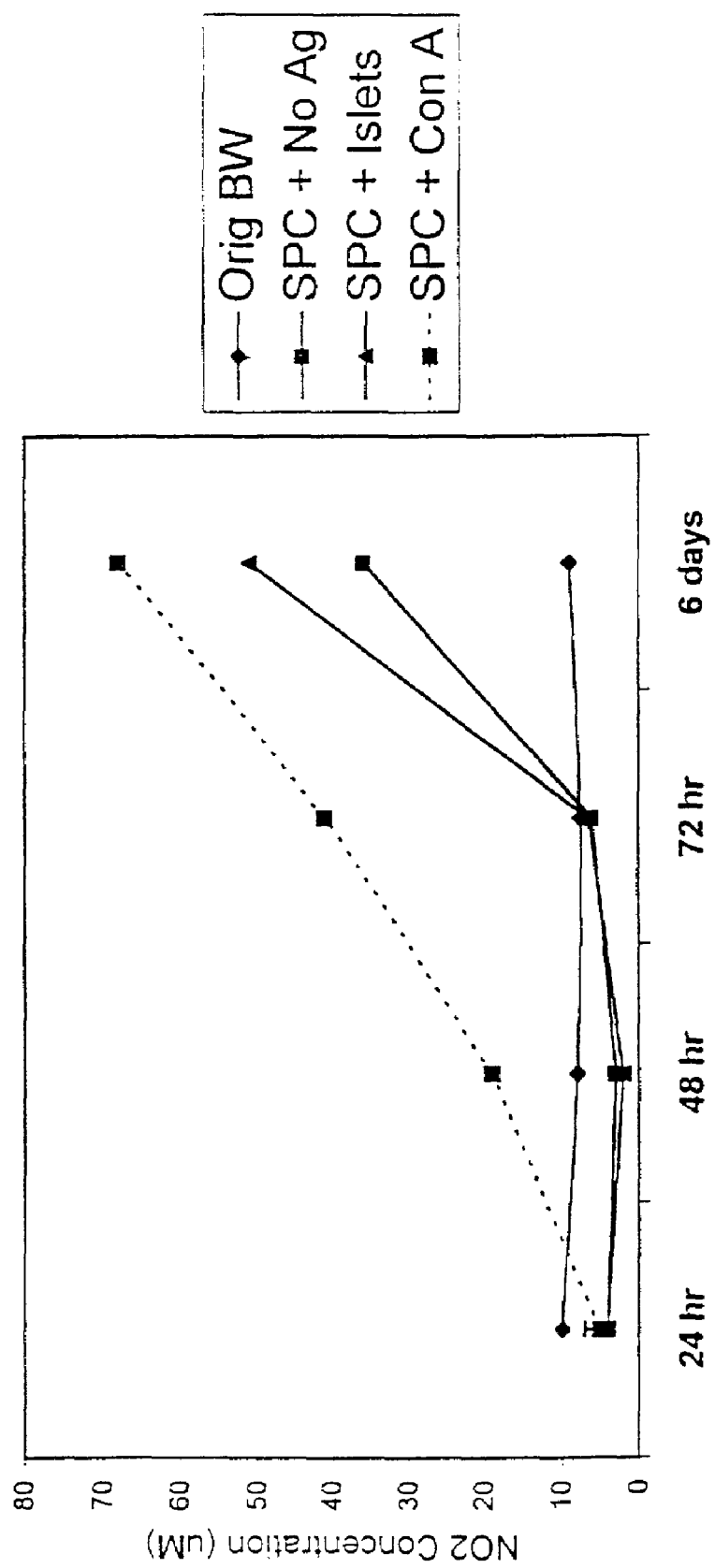
FIG. 58  NO2 Production by Cells from NOD #1335 (Expt 288)

METHOD OF INHIBITING IMMUNE SYSTEM DESTRUCTION OF TRANSPLANTED VIABLE CELLS

This application is a continuation-in-part of PCT International Application No. PCT/US96/15577, filed Sep. 27, 1996 which claims the benefit of U.S. Provisional Application No. 60/004,375, filed Sep. 27, 1995, the contents of which are hereby incorporated by reference.

The invention disclosed herein was made with Government support under NIH Grant Nos. RO1-DK39088 and RO1DK53057. Accordingly, the U.S. Government has certain rights in this invention.

Throughout this application, various references are referred to within parentheses. Disclosures of these publications in their entireties are hereby incorporated by reference into this application to more fully describe the state of the art to which this invention pertains. Full bibliographic citation for these references may be found at the end of this application, preceding the claims.

BACKGROUND OF THE INVENTION

There is a critical need for better insulin replacement therapy to circumvent the complications of insulin-dependent diabetes mellitus (IDDM). Our goal is to develop techniques for transplantation of microencapsulated, xenogeneic islets to provide a durable, physiological source of insulin to diabetic patients. It has previously been shown that microcapsules are biocompatible and that xenogeneic islet grafts contained in microcapsules functioned indefinitely in the peritoneal cavity of mice with streptozotocin-induced (SZN) diabetes. Thus, microcapsules may be intact and stable in vivo and factors that may be required for long-term survival and function of the xenogeneic islets are accessible. The microcapsules serve as a mechanical barrier that prevents cell-to-cell contact between recipient lymphocytes and donor islets. The mechanical barrier primarily prevents host sensitization rather than protecting the graft from immune destruction, because encapsulated islets are very rapidly destroyed by recipients that are presensitized to the islet donor cell antigens. Similarly, encapsulated xenogeneic islets were rejected (in two weeks) by NOD mice, which is possibly due to presensitization of NODs to islet antigens. Xenografts undergoing rejection in NOD mice were surrounded by large numbers of activated macrophages and immunoglobulins, with IL-1α, TNFα, both documented by immunocytochemistry, and IL-4 messenger RNA detected by RT-PCR. We postulate that NOD rejection is initiated by donor antigens that are secreted by or shed from the encapsulated islets and which are processed via the MHC (major histocompatibility complex) class II pathway by host APC (antigen presenting cells). These APC activate NOD CD4$^+$ T cells that develop into a Th2 response, with donor islet destruction occurring via cytokine-mediated events.

We have also been able to improve the microencapsulation process to permit long-term survival of concordant, rat islet xenografts, even in NOD mice. Furthermore, we have found that blockade of NOD co-stimulatory molecules with CTLA4Ig significantly prolongs survival of discordant, rabbit islet xenografts for up to 200 days. Thus, we have been able to overcome problems associated with transplanting encapsulated islet xenografts into autoimmune diabetic recipients.

Insulin-Dependent Diabetes Mellitus

The last several years have witnessed a remarkable increase in or knowledge of the effects of therapies for insulin-dependent diabetes mellitus (IDDM). The Diabetes Control and Complications Trial (DCCT) found that intensive insulin therapy delayed the onset and slowed progression of retinopathy, nephropathy, and neuropathy in patients with IDDM (1). Unfortunately, intensive insulin therapy is not appropriate for many IDDM patients; and even with careful monitoring, DCCT patients had increased episodes of severe hypoglycemia (1). Ironically, results of the DCCT support the rationale for pancreas and islet transplantation. Since the inception of islet transplant experiments, it has been the hope that such grafts might supply insulin more homeostatically than exogenous insulin can, and that 'near-normal' modulation of carbohydrate metabolism might prevent the secondary complications of IDDM (2). Clinical pancreas allografts have improved outcomes with the advent of combination immunosuppression; and near normal of glucose homeostasis follows most pancreatic allo- and autografts (3). However, the first-year mortality of a human pancreatic allograft remains high (10%), immunosuppression is required, and only limited numbers of clinical whole-organ pancreatic transplants are being done worldwide (2, 4, 5).

The Rationale for Microencapsulated Islet Xenografts

Islet transplantation is an attractive therapy for patients with IDDM, since problems related to the exocrine pancreas may be avoided. However, allografts of donor human islets have not been successful long-term (3); and availability and yield of human islets are limited. Therapeutic islet transplants for large number of patients almost certainly will require donor islets harvested from animals (xenografts) (2, 4).

The optimal source of xenogeneic islets for clinical use remains controversial. Islets have been isolated from sub-human primates and xenografted into immunosuppressed, diabetic rodents, with short-term reversal of diabetes (6). However, there are significant ethical issues surrounding use of primates, Other promising sources are porcine, bovine, canine, and rabbit islets, which function remarkably well, (i.e., maintaining normoglycemia) in diabetic rodents until transplant rejection occurs (7–11). Long-term human, bovine and porcine islet xenograft survival has been documented in nude mice and rats, suggesting that sufficient islet-specific growth factors are present in xenogeneic recipients (2, 12–17). For sociologic/ethical reasons, canine islets are not clinically appropriate. Porcine islets are both difficult to isolate (intact) and to maintain in vitro; nevertheless, they are extremely promising for eventual clinical application (18–21). Isolation of bovine islets is technically easier (than porcine islets), and calf islets are glucose-responsive (22). Recently, large scale rabbit islets isolation has been developed (23) (see Preliminary Studies). Rabbit pancreas is an attractive source of islets. Rabbit, like porcine insulin, differs from human insulin at only one amino acid, and rabbit islets are glucose responsive (22, 24). In addition, most humans do not possess natural anti-rabbit antibodies, which might improve the possibility of preventing xenograft rejection (25). It is currently feasible to consider isolation of 1,000,000 donor islets/per human diabetic recipient from either calves, pigs or rabbits, utilizing multiple donors.

The most significant obstacle to islet xenotransplantation on human IDDM is the lack of an effective immunosuppressive regiment to prevent cross-species graft rejection (2, 26–28). Recently, it has been reported that human islets will survive long-term in SZN-diabetic mice treated either with anti-CD4 antibody (16) or CTLA4Ig (a high affinity fusion protein which blocks CD28-B7 interactions) (12), or by exposure of donor islets to purified high affinity anti-HLA (ab)$_2$ (29). However, with the exception of these studies, indefinite survival of islet xenografts has rarely been achieved, except with the aid of porous, mechanical barriers. Both intra- and extra-vascular devices are under development. However, potential clinical complications, such as bleeding, coagulation, and bioincompatibility mitigate against their current use in diabetic patients (30, 31). For example, acrylic-copolymer hollow fibers placed subcutaneously maintained viability of human islet allografts for two weeks (50 islets per 1.5 cm fiber) (65,000 M.W. permeability) (32).

However, to implant 500,000 islet would require >150 meters of these hollow fibers, which is not clinically feasible.

One of the most promising islet envelopment methods is the polyamino acid-alginate microcapsule. A large number of recent studies have shown that intraperitoneal xenografts of encapsulated rat, dog, pig or human islets into streptozotocin-diabetic mice or rats promptly normalized blood glucose for 10–100$^+$ days (7, 19, 33–39). Long-term normalization of hyperglycemia by microencapsulated canine islet allografts, porcine islet xenografts, and one human islet allograft has been reported (21, 40–42). The mechanisms by which microcapsules protect islet xenografts from host destruction are not fully understood. However, it has been suggested that prohibition of cell-cell contact with host immunocytes is important (30, 35). The marked prolongation of widely unrelated encapsulated islet xenografts in rodents with induced diabetes has prompted studies in animals with spontaneous diabetes.

The Spontaneously Diabetic NOD Mouse as a Model of Human IDDM

Nonobese diabetic (NOD) mice develop diabetes spontaneously, beginning at approximately twelve weeks of age. NOD mice are the most appropriate model for studying the feasibility of islet xenotransplants because their disease resembles human IDDM in several ways. Macrophage, dendritic cell and lymphocytic infiltration of islets can be detected as early as four weeks of age and precedes overt hyperglycemia (43–46). NOD diabetes is T lymphocyte-dependent (43–45); and it is associated with (MHC) Class II genes (47–50). Cytotoxic T cells and antibodies specific for beta cells or for insulin have been identified, characterized and cloned from NOD mice (44, 45, 51–55). Loss of tolerance to islet antigens in NODs correlates with appearance of Th1 immune responses to glutamic acid decarboxylase, a factor which has been reported to be a primary auto-antigen in human IDDM (5,657). The disease can be induced in non-diabetic, syngeneic mice by transfer of both CD8$^+$ and CD4$^+$ T cells or T-cell clones from diabetic NODs (44, 52, 55, 58); and inhibition of NOD macrophages or CD4$^+$ T lymphocytes or treatment with anti-Class II monoclonal antibodies prevents or delays diabetes onset in NOD mice (59, 50). Defects in NOD macrophages, C5 complement and NK cell function have been reported (61). It has been suggested that helper T-cells function to activate CD8$^+$ cells, which damage beta cells by direct cytotoxic attack. However, some recent studies have suggested that beta cell killing may be indirect, from a nonspecific inflammatory response which initially involves CD4$^+$ cells, but also includes infiltrating macrophages, which release cytokines and oxygen free-radicals (particularly nitric oxide), known beta cell toxins (62–65). Because of similarities to IDDM, NOD mice are the best model in which to study islet xenografts.

Recently, the Scid mutation has been back-crossed onto the NOD background, resulting in immuno-deficient NOD-Scid mice (66–69). These mice homologous for the Scid mutation, which results in an inability to rearrange T-cell receptor and immunoglobulin genes (66, 67). The consequence is an absence of T and B-lymphocytes. These mice do not develop diabetes spontaneously; but they may be rendered diabetic with multiple low-dose streptozotocin (MLD-SZN) regimens, making them an optimal model for adoptive transfer experiments (67–69). NOD-Scids express NOD MHC genes and other genes that are relevant for development of the disease. They mount robust macrophage and limited NK-cell responses, but are functionally T- and B-lymphocyte deficient (69).

Islet Xenografts into Diabetic NOD Mice

Unlike mice with SZN-induced diabetes, diabetic NOD mice rapidly reject unencapsulated islet xenografts, allografts and isografts (7, 8, 10, 19, 33, 56, 70, 71). Conventional immunosuppressive regimens have little effect on this reaction (10, 71–73). Treatment of NOD recipients with monoclonal antibodies directed against CD4$^+$ helper T lymphocytes or FK506 prolongs islet graft function (from 5 to 25 days) (7, 8, 10, 73); but long-term islet graft survival in NODs has not been reported.

Several laboratories have reported that intraperitoneal microencapsulated islets (allo- and xeno-geneic) function significantly longer than non-encapsulated controls, but eventually are destroyed also by recipients with spontaneous (autoimmune) diabetes (NOD mice or BB rats) (7, 9, 19, 33, 35, 70, 74–78). Rejection is accompanied by an intense cellular reaction, composed primarily of macrophages and lymphocytes, which entraps islet-containing microcapsules and recurrence of hyperglycemia within 21 days, in both NOD and BB recipients (7, 19, 74, 76, 77). The mechanism of encapsulated islet rejection by animals with spontaneous diabetes remains incompletely understood, but the fact that it rarely occurs in mice with induced (SZN) diabetes suggests that anti-islet autoimmunity may be involved in islet graft destruction.

Mechanisms of NOD Destruction of Encapsulated Islet Xenografts: Macrophages, T-Cells, and Cytokines It has been suggested by several investigators that microcapsules, like other bioartificial membrane devices promote survival of xenogeneic and allogeneic islets by: (A) preventing or minimizing release of donor antigen(s), thereby reducing host sensitization, and/or (B) preventing or reducing host effector mechanisms (i.e. T-cell contact, anti-graft antibody binding, cytokine release).

Most studies of rejection of islets in microcapsules and other membrane devices have focused on effector mechanisms. For example, Halle (35) and Darquy and Reach (79) reported that microcapsules protected donor islets from host immunoglobulins, specifically human anti-islet antibodies and complement effects, in vitro. Although complement components, are too large (>>150,000 Kd) to enter conventional poly-l-lysine microcapsules, it is possible that antibodies combine with shed donor antigens forming complexes which bind to FcR of macrophages in vivo (in the peritoneal cavity) which could initiate cytokine release causing encapsulated islet destruction (80). Complement could facilitate binding of complexes to macrophages via the C3b receptor or by the release of chemotactic peptides that could increase the number of macrophages.

Involvement of NOD T-lymphocytes in rejection of encapsulated islets has been proposed by Iwata, et al. (81), who found significant prolongation of encapsulated hamster-to-NOD mouse encapsulated islet xenografts when NOD recipients were treated with deoxyspergualin (DSG), a T-cell inhibitory immunosuppressant (81). This data is consistent with prior finding of several laboratories, that treatment of NODs with monoclonal antibodies directed against CD4⁺ helper T cells or FK-506 prolonged function of both encapsulated and nonencapsulated rat-to-NOD islet xenograft (7, 8, 10, 73) and these finding are similar to observations of Auchincloss (27), Pierson (82) and Gill (83), that CD4⁺ T cells play a dominate role in xenoreactivity.

A prominence of macrophages/monocytes in peri-microcapsular infiltrates of encapsulated islet allografts and xenografts in NOD mice and BB rats has been reported (7, 33, 36, 74, 76–78, 84). Cytokines known to be products of macrophages, including IL-1 and TNF (62, 77, 85, 86), may be involved destruction of encapsulated islets. Both IL-1 and TNF have been reported to reduce insulin secretion and cause progressive damage of islet cells in vitro (58, 62–64, 85–87). Cytokine-mediated injury might occur directly or indirectly, by activation of an intraperitoneal inflammatory response (30, 77). Recently, it has been reported by Dr. J. Corbett (IPITA conf. June 1995), that there are as many as ten macrophages within each islet. IL-1 induces nitric oxide synthase (NOS) (63–65), with resultant generation of nitric oxide (NO), which causes injury to mitochondria and to DNA in beta cells (63–65). Furthermore, this pathway of islet damage is worsened by TNF (88, 89). Theoretically, macrophages from within donor islets and host peritoneal cavity or within the down islets could be involved in cytokine-mediated damage to encapsulated islets.

Studies of cytokine messenger RNA profiles in hamster-to-rat liver and pig-to-mouse islet xenografts have found selective increases in Th2 cytokines (IL-4, IL-5, IL-10) and no change from normal in IL-2 (11, 90). These are distinctly different from those of O'Connell, et al. (91, 92), who reported IL-2 messenger RNA in biopsies of allograft rejections of nonencapsulated islets. Increased Th2 activity relative to Th1 (93–95) activity is distinct from the known NOD 'Th1' anti-islet immune response (56, 57, 96). The Th2 response is characteristic of evoked antibody responses to foreign antigens and suggests that humoral reactions to encapsulated xenografts may be of critical importance. Furthermore, strategies designed to abrogate 'Th2' responses may significantly prolong encapsulated islet xenograft survival. The 'Th2' helper T-cell cytokine mRNA profile is characteristic of antibody responses to foreign antigens.

Costimulatory Molecules, APC's and Islet Xenograft Destruction by NOD Mice

Involvement of APCs in immune responses to islet xenografts is suggested by recent studies of Lenschow, et al. (12), who found that blockade of the co-stimulatory molecule, B7 with the soluble fusion protein, CTLA4Ig, prolonged human-to-mouse islet xenografts in SZN-diabetic mice. Several studies, in vitro and in vivo, have shown that foreign molecules which interact with the T cell receptor (peptides, specific antibodies, mitogens) fail on their own to stimulate naive T cells to proliferate (95, 97), and may induce antigen-specific anergy. At least one additional (co-stimulatory) signal is required, and it is delivered by APCs. In mice, one such costimulatory pathway involves the interaction of the T-cell surface antigen, CD28 with either one of two ligand, B7-1 and B7-2, on the APCs (95, 97–102). Once this full interaction of T-cells and APCs occurs, however, subsequent re-exposure of T-cells to peptide, mitogen, etc. will result in proliferation in the absence of costimulation. (95).

CTLA4 is a cell surface protein that is closely related to CD28; however, unlike CD28, CTLA4 is expressed only on activated T-cells. B7-1 has a high affinity for CLTA4 than CD28; and it has been suggested that CTLA4 may modulate functions of CD28 (97, 103, 104). CTLA4Ig is a recombinant soluble fusion protein, combining the extracellular binding domain of the CTLA4 molecule with constant region of the $IgG_1$ gene. Both human and murine CTLA4Ig have been shown to inhibit T-lymphocyte responses in mice (141, 142). Administration of CTLA4Ig to mice has been shown to induce antigen-specific unresponsiveness (in a murine lupus model) (97, 99, 105) and long-term acceptance of murine cardiac allografts (106, 107). In addition, Lenschow, et al., found that it induced tolerance to human islets in SZN-diabetic mice (12). CTLA4Ig has also been reported to reduce the incidence of diabetes in NODs (108). There are no reports of effects of CTLA4Ig on islet graft survival in spontaneously-diabetic recipients, such as NOD mice. However, our studies show that CTLA4Ig significantly prolongs survival of encapsulated rabbit islets in NOD recipients.

Recent studies have further illuminated helper T-cell-APC interactions, with recognition of the importance of binding of the APC-CD40 antigen to its ligand, GP39, on helper T-cells (109, 110). A monoclonal hamster anti-murine GP39 antibody (MR1) blocks helper T-cell interactions with APCs, macrophages, effector T-cells and B-lymphocytes (109, 110). Dr. A. Rossini has reported recently (IPITA conf. June 1995) that MR1 plus B7 negative donor spleen cells day 7 allows long-term survival of both allo- and xeno-geneic islets in SZN-diabetic mice.

The Immunogenicity of Encapsulated Islets and Mechanisms of Graft of Destruction Empty microcapsules have been reported to elicit no cellular responses (33, 35, 36). On the other hand, others have found reactions to empty capsules, (30, 76, 77, 111, 112). Impurities in reagents such as contamination with endotoxin or high concentrations of mannuronate most likely contribute to bioincompatibility (113). It is apparent that some formulations of poly-l-lysine microcapsules are biocompatible and some are not. Until standardized reagents are available, immunologic studies are microencapsulated islets can only be interpreted when investigators include empty microcapsule controls which document their biocompatibility.

Recently, de Vos, et al. (114) reported incomplete encapsulation or actual protrusion of islets through microcapsule membranes in some microcapsules, and suggested this biomechanical imperfection is one factor in microcapsule destruction. Similar observations have been made by Chang (115), who found incorporation of islets and hepatocytes within the walls of poly-l-lysine alginate microcapsules. Several other investigators have published photomicrographs of encapsulated islets showing obvious entrapment of islets in capsules, walls, but did not comment on this problem (35, 116, 117). Incomplete encapsulation would be anticipated to result in premature capsule fracture and exposure of donor islets to host cells; but there are no reports analyzing this as a source of donor antigen exposure, sensitization and host.

Relatively few studies have focused on the role of donor islet antigen(s) released from microcapsules in initiating host immune responses. Ricker, et al. (33) reported similar, intense cellular reactions by NOD mice to rat insulinoma, hepatoma and pheochromocytoma cell lines in microcapsules and concluded that the NOD immune reaction was not islet-specific. Horcher, et al. (36) reported 15-week survival of 6/7 encapsulated Lewis rat islet isografts, compared to failure of 8/10 encapsulated Wistar-to-Lewis islet allografts within 56 days. Isograft biopsies showed viable islets, intact capsules and no pericapsular immune reaction (36), while biopsies of failed allografts revealed pericapsular cellular responses and nonviable islets. This is the only report in the literature with encapsulated islet isograft controls. Although the Lewis rat model is not one with autoimmune diabetes, the results are significant, and suggest that donor antigen(s) are the stimulus for subsequent host responses.

SUMMARY OF THE INVENTION

This invention provides a method of inhibiting viable cells transplanted into a subject from being destroyed by the subject's immune system which comprises: a) containing the viable cells, or tissue comprising the viable cells, prior to transplantation within a device comprising a semipermeable membrane; and b) treating the subject with a substance which inhibits an immune-system costimulation event in an amount effective to inhibit the subject's immune system from responding to said contained cells or tissue.

In one embodiment, the substance which inhibits an immune-system costimulation event is CTLA4. Accordingly, this invention further provides a method of inhibiting viable cells transplanted into a subject from being destroyed by the subject's immune system which comprises: a) containing the viable cells, or tissue comprising the viable cells, prior to transplantation within a device comprising a semipermeable membrane; and b) treating the subject with CTLA4 in an amount effective to inhibit the subject's immune system from responding to said contained cells or tissue.

This invention also provides a method of treating diabetes in a subject which comprises: a) containing viable insulin-producing cells, or tissue comprising viable insulin-producing cells, within a device comprising a semipermeable membrane so as to obtain contained viable insulin-producing cells; b) transplanting contained viable insulin-producing cells obtained in step (a) into the subject in an amount effective to treat diabetes in the subject; and c) treating the subject with a substance which inhibits an immune-system costimulation event in an amount effective to inhibit the subject's immune system from responding to an amount of contained viable insulin-producing cells according to step (b).

BRIEF DESCRIPTION OF THE DRAWINGS

FIG. 24: Intraperitoneal microencapsulated neonatal porcine islet xenografts in NOD mice treated with CTLA4Ig*, which does not fix complement.

Figure 26:
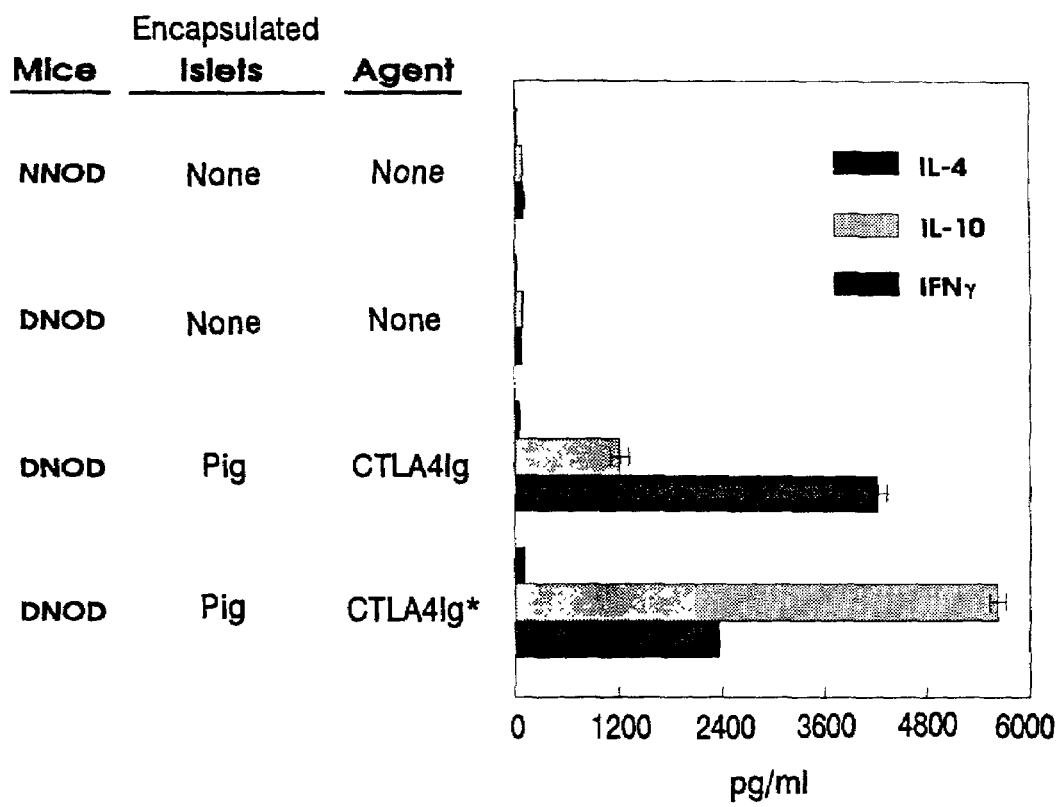

FIG. 26: Lymphokine production in cultures of spleen cells from the mice described in FIG. 24 were determined by ELISA. Spleen cells from normal or diabetic NOD mice were cultured with unirradiated neonatal, pig islets as described in FIG. 24. Supernatent fluids were harvested after 24 hrs of incubation and assayed for IL-4, IL-10 and IFNγ using a sandwich ELISA and the appropriate recombinant cytokines as standards.

Figure 27:
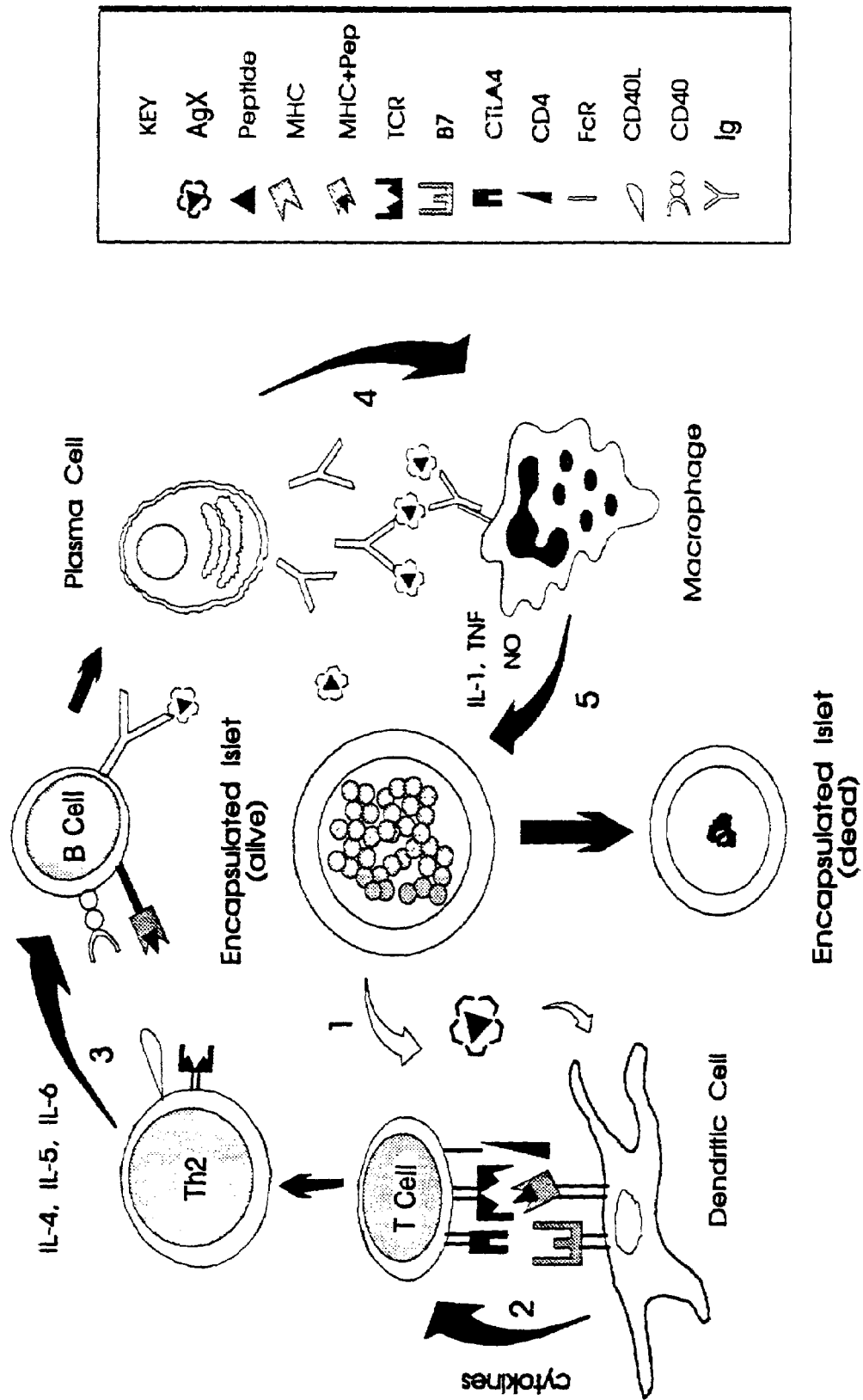

FIG. 27: Model of immune response to micro encapsulated, xenogeneic islets by autoimmune, NOD mice. Secreted insulin clearly crosses the membrane of double walled microcapsules and regulated glucose levels in engrafted mice. 1): Potentially, other donor proteins or protein fragments of less than 100,000 mw (AgX) that are shed or secreted by islets diffuse out of microcapsules and are endocytosed by dendritic cells. 2): Dendritic cells process proteins via the MHC class II pathway and present peptide X complexed with class II and co-stimulatory molecules to CD4⁺ T cells. In the presence of the appropriate cytokines, CD4⁺ T cells are activated and develop into Th2 cells that express CD40L (GP39). B cells with surface IgM that bind AgX endocytose and process it into peptides that bind MHC class II which are expressed on the surface of B cells. Th2 specific peptide X complexed with class II binds B cells and the interaction of CD40 with CD40L (GP39) causes the activation of B cells. 3): Activated B cells mature into plasma cells under the direction of Th2 lymphokines. 4): Plasma cells secrete specific antibody that forms complexed with AgX. 5): Binding of complexes to FcR activated macrophages to secrete a variety of mediators including IL-1, TNFα and nitric oxide (NO), all of which have toxic effects on islets and all of which are small enough to cross the double-walled microcapsules.

FIG. 28A-B: (A) Neonatal islet in microcapsule, biopsied day 103 from peritoneal cavity of SZN-diabetic NOD-Scid mouse (H&E) (approx. 240×). Arrow points to outer surface of microcapsule membrane. (B) Same biopsy as (A), adjacent section. Antiinsulin immunohistochemistrty, showing intensely insulin-positive beta cells, occupying approx. 80% of islet (approx. 240×). Arrow points to outer surface of microcapsule membrane.

FIG. 29A-B: (A) Functioning encapsulated neonatal porcine islets, biopsied day 101, from peritoneal cavity of NOD mouse, treated with CTLA4-Ig for 21 days. Note absence of NOD cell response on outside of membrane and viable islet within capsule (H&E) (×240). Arrows point to outside of capsule wall. (B) Same biopsy as (A). Adjacent section showing majority of cells positive for insulin. Antiinsulin immunocytochemistry (×240).

Figure 30:
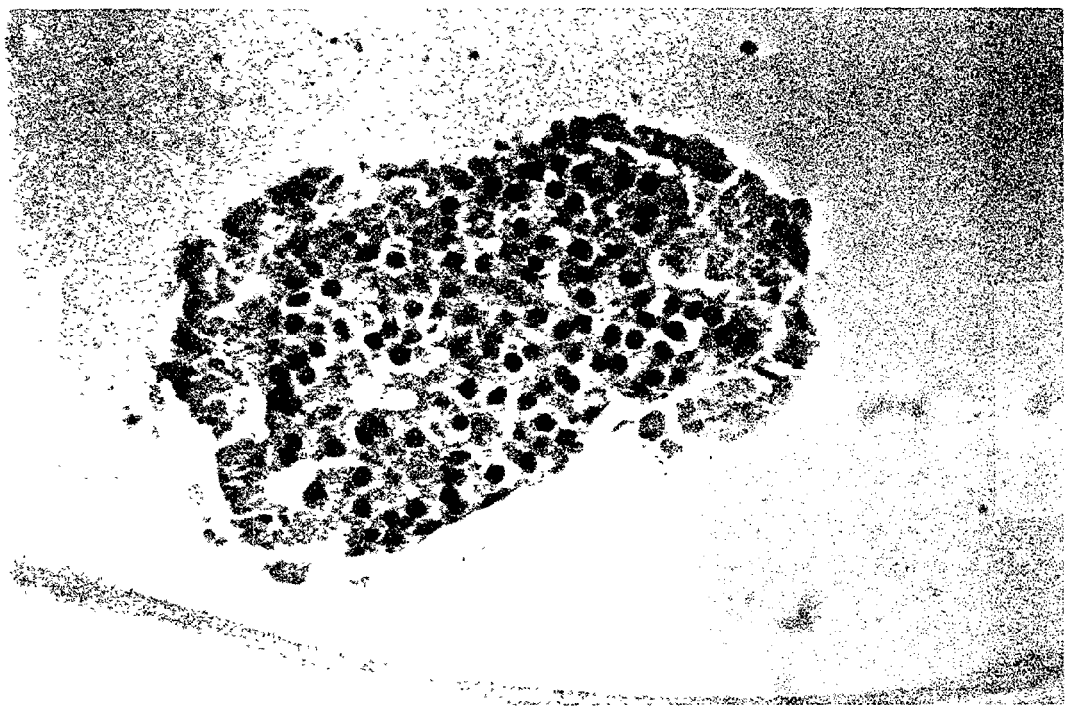

FIG. 30: Biopsy of microencapsulated pig islet xenograft from functioning (normoglycemic) transplant into spontaneously diabetic NOD mouse, day #239 after transplantation. Note viable islet cells within microcapsule. Hematoxylin & Eosin (H&E), ×400. NOD treated with CTLA4Ig for only 21 days after grafting.

Figure 31:
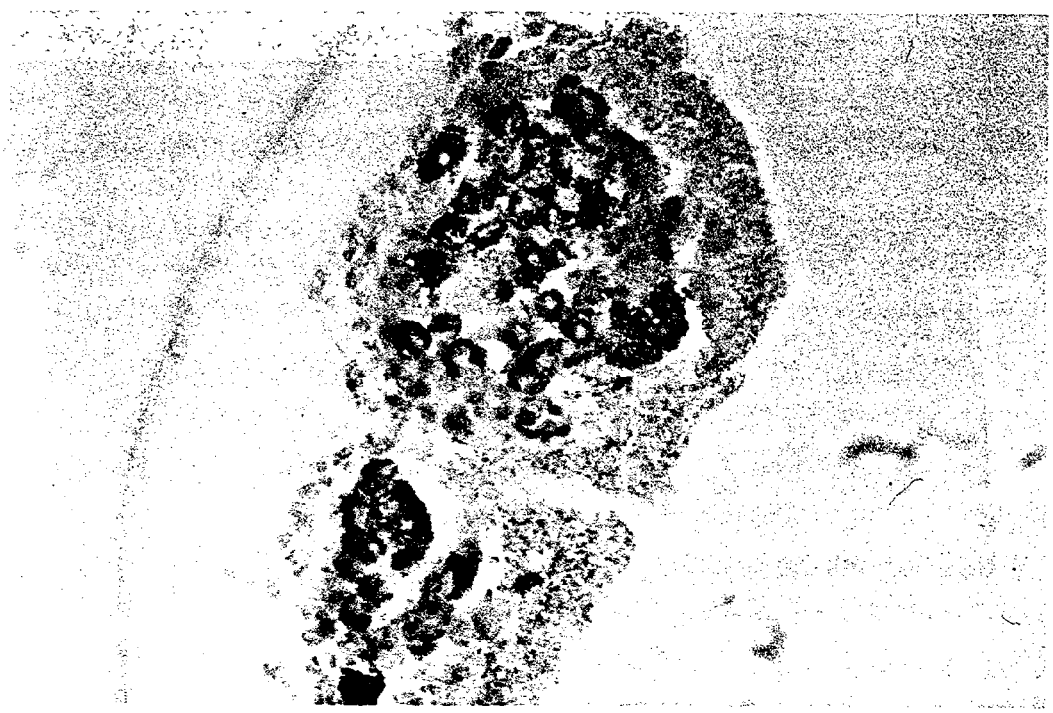

FIG. 31: Same biopsy as in FIG. 29; anti-insulin immunohistochemical stain, showing insulin (dark brown) granules in cytoplasm of pig islet "beta" cells within intact microcapsule. Note absence of host NOD cellular reaction on outside of microcapsule membrane (×400).

Figure 32:

FIG. 32: Microencapsulated pig islet xenograft biopsied on day #83 after successful transplant to CTLA4Ig-treated NOD mouse. Note intact "double-walled" microcapsule membrane, viable pig islet cells, and absence of NOD cellular reaction on outside of membrane (H&E, ×400).

Figure 33:

FIG. 33: Microencapsulated pig islet xenograft biopsied on day #180 with successful transplantation to NOD mouse. Note absence of NOD reaction to graft (clean, intact capsule membrane). NOD treated with CTLA4Ig for only 21 days (×400, H&E).

Figure 34:
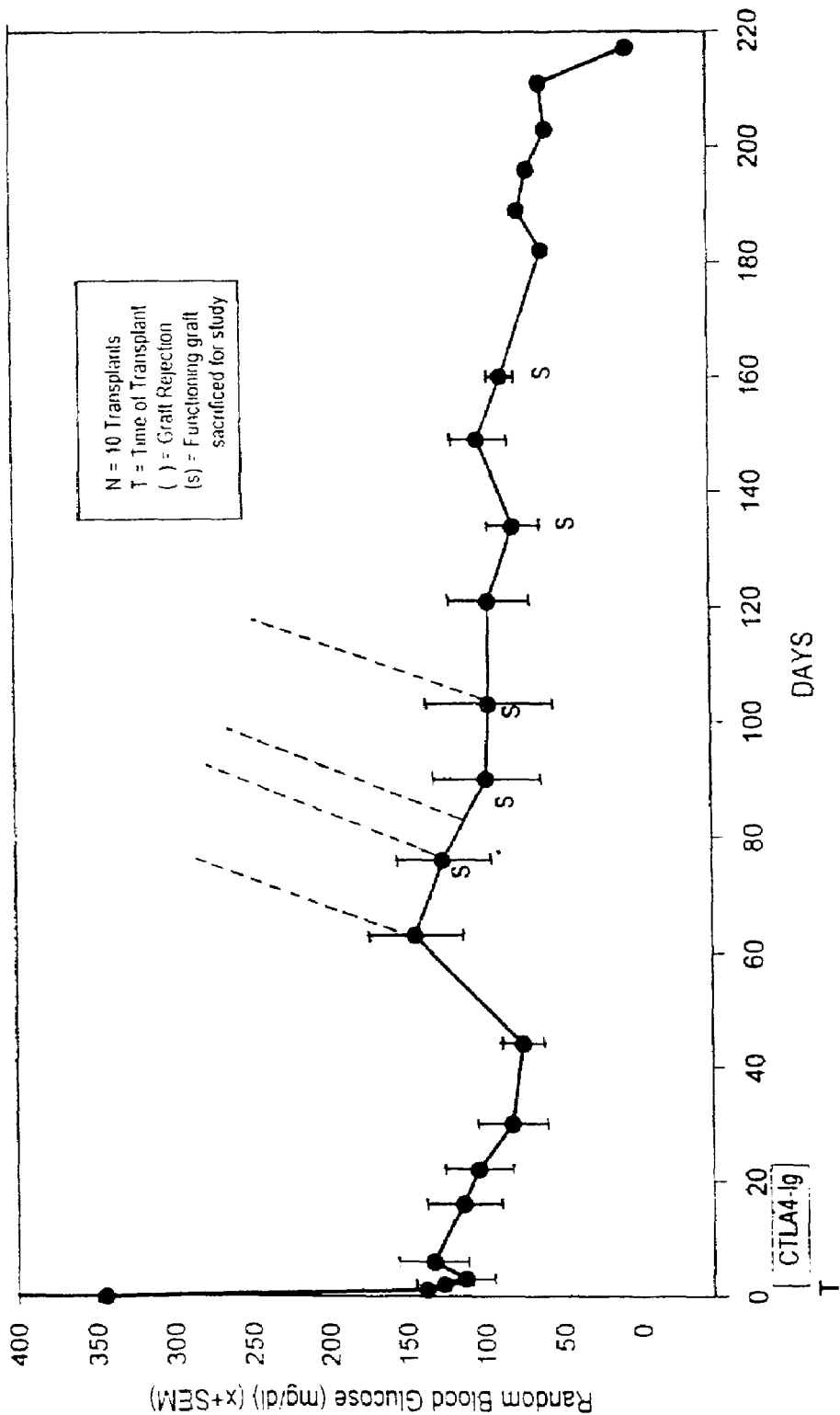

FIG. 34: Microencapsulated neonatal pig islet transplants into diabetic NOD mice treated with CTLA4-Ig for 21 days.

Figure 35:
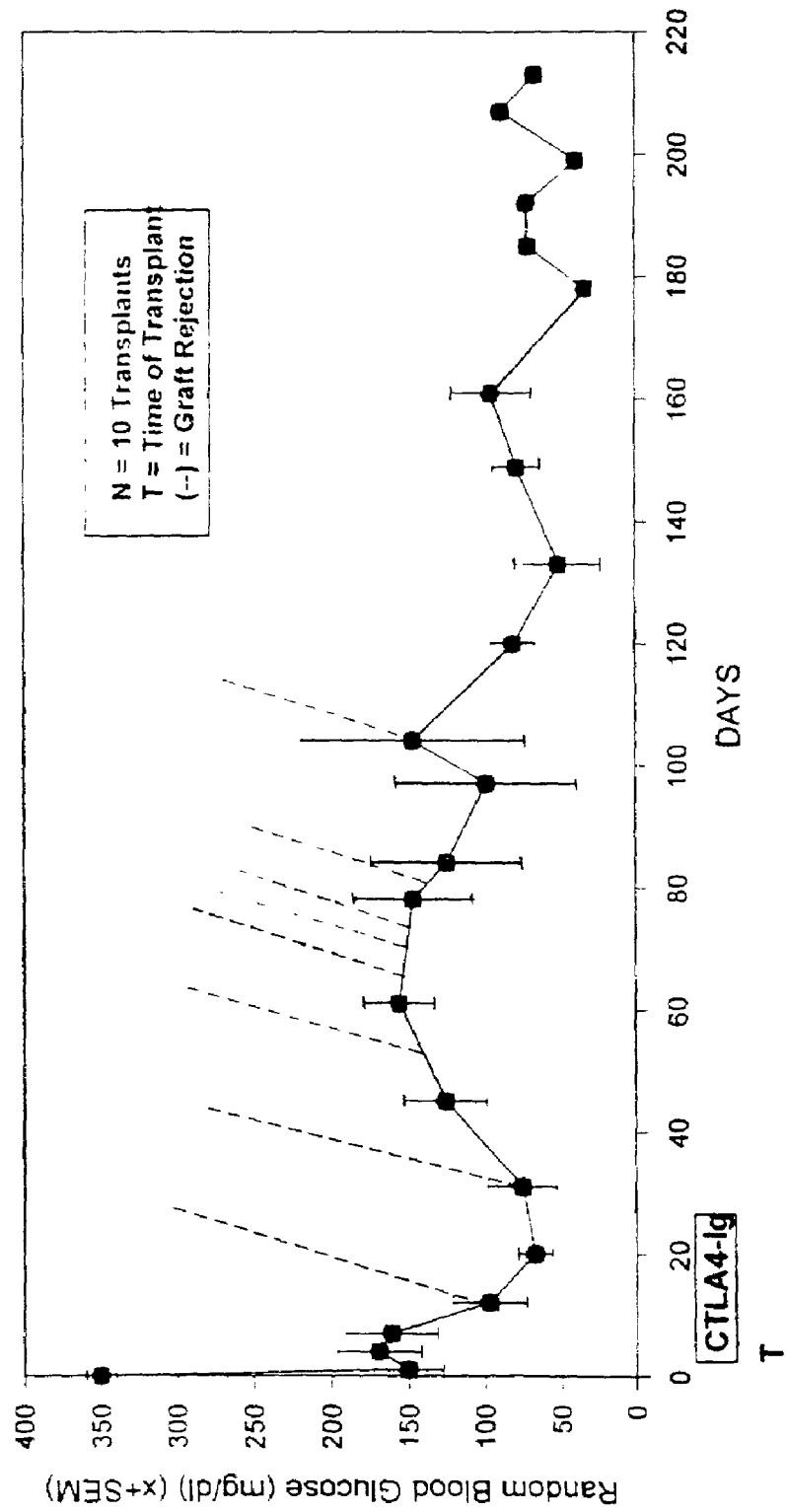

FIG. 35: Microencapsulated neonatal pig islet transplants into diabetic NOD mice treated with mutant CTLA4-Ig for 21 days.

Figure 36:
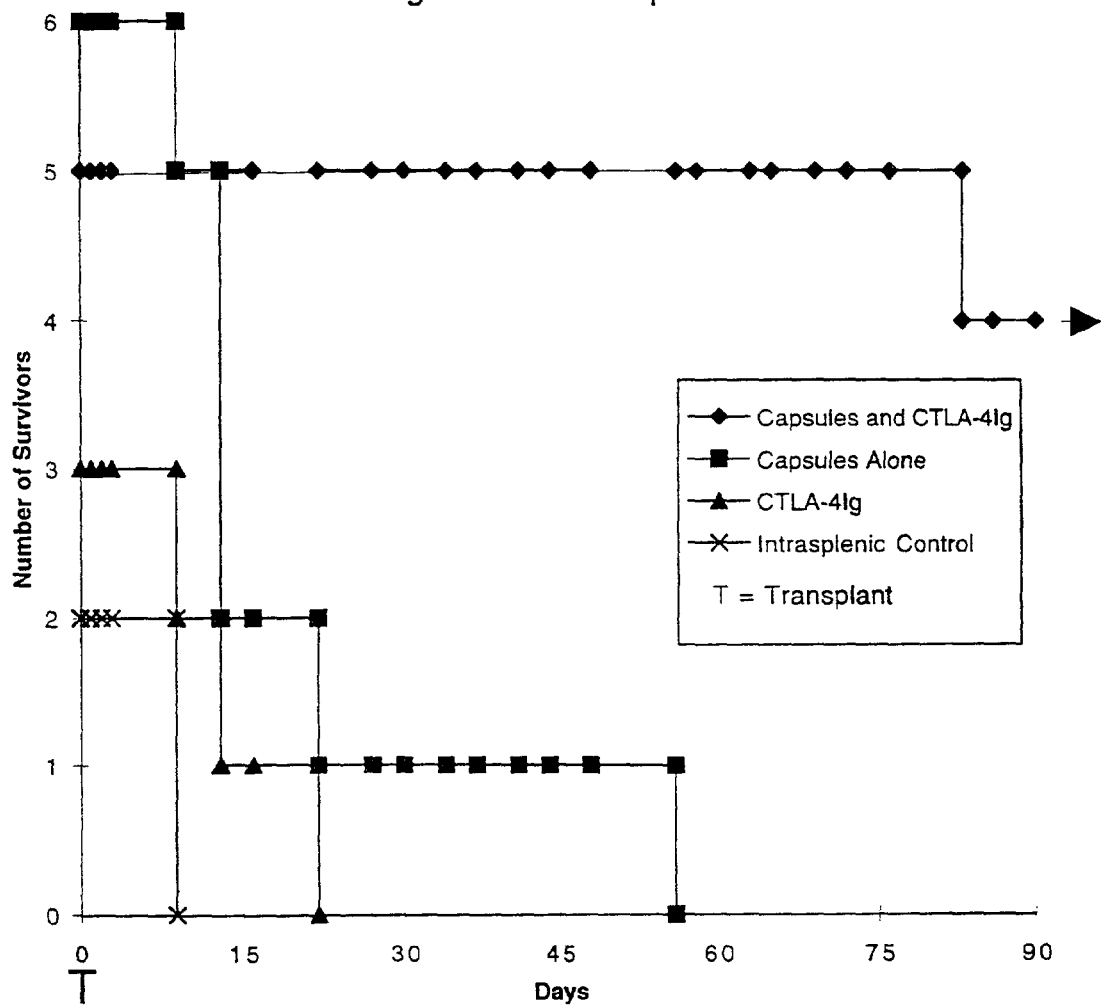

FIG. 36: Neonatal porcine islet xenografts in NOD mice: effets of CTLA4-Ig and microencapsulation.

Figure 37:
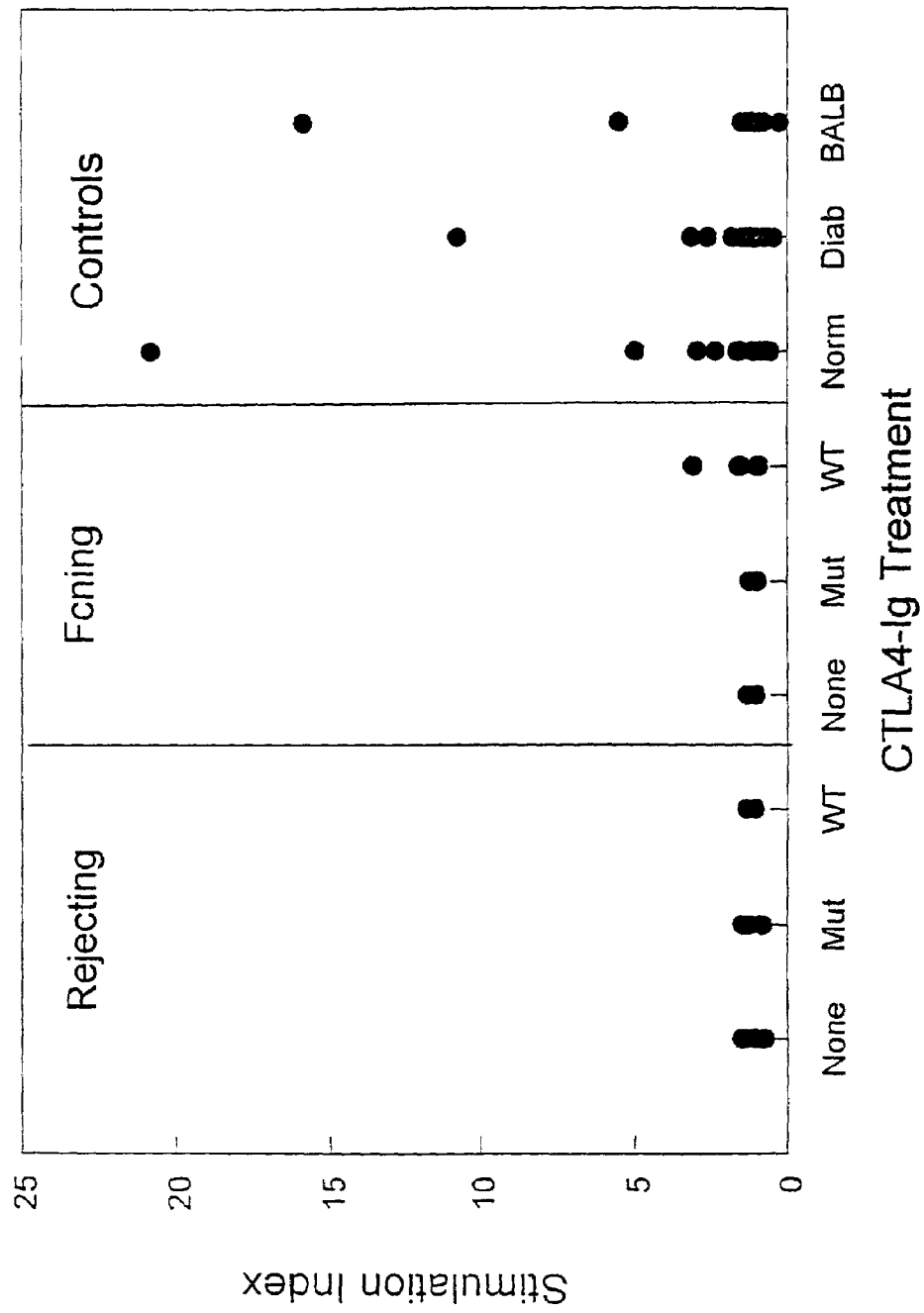

FIG. 37: Islet-specific proliferation by spleen cells (SPC) from NODs with rejected or functioning grafts.

Figure 38:
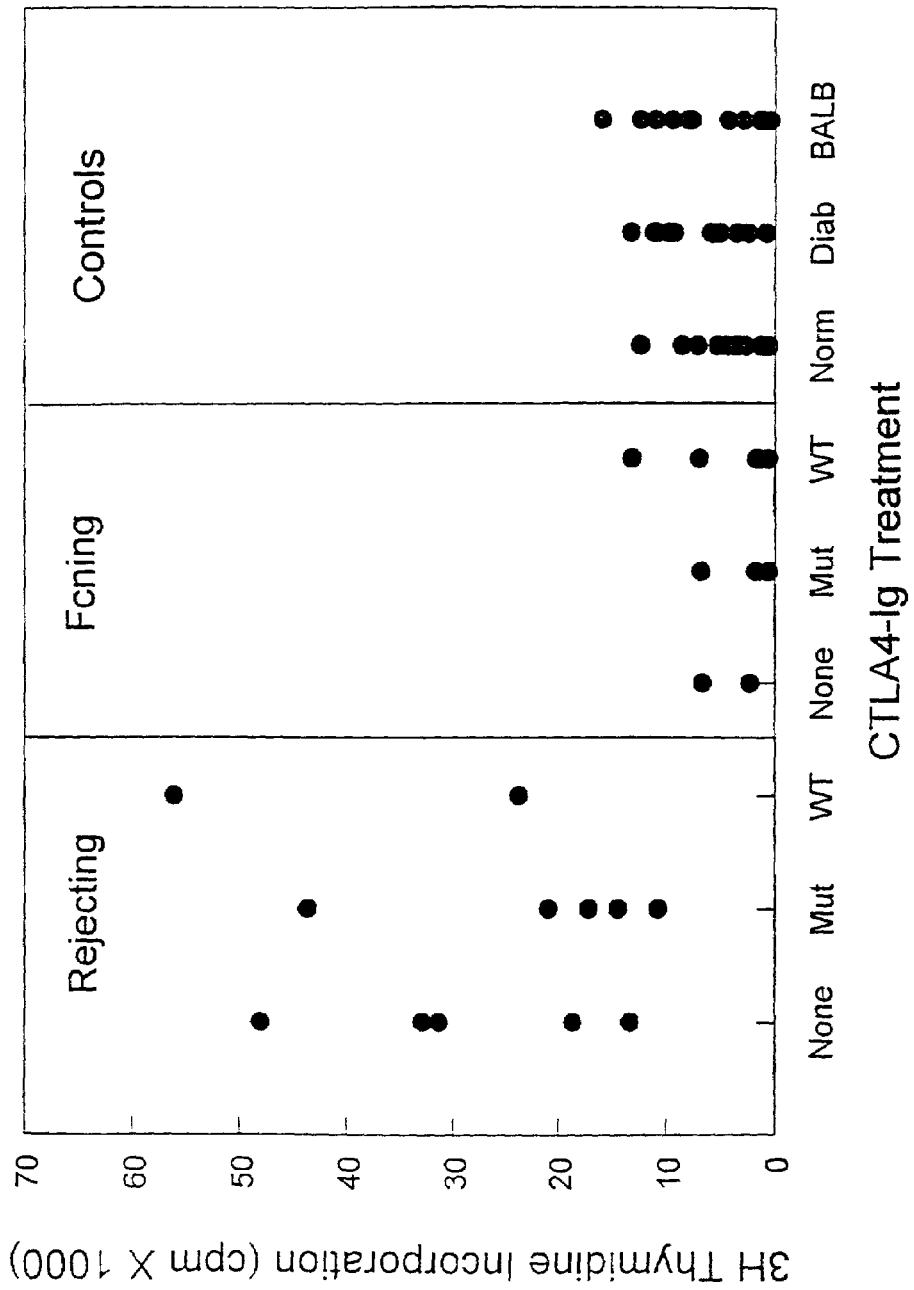

FIG. 38: Spontaneous proliferation by spleen cells (SPC) from NODs with rejected or functioning grafts.

FIGS. 39A–B: (A) IL-2 present in peritoneal fluid on sacrifice (sac) day, transplanted NODs. (B) IL-2 present in peritoneal fluid on sacrifice (sac) day, untransplanted mice.

FIGS. 40A–B: (A) IL-2 secreted by spleen cells (SPC) cultured with porcine islets, transplanted NODs—not rejecting. (B) IL-2 secreted by spleen cells (SPC) cultured with porcine islets, transplanted NODs—rejecting.

FIGS. 41A–B: (A) IFN-gamma present in peritoneal fluid on sacrifice (sac) day, transplanted NODs. (B) IFN-gamma present in peritoneal fluid on sacrifice (sac) day, untransplanted mice.

FIGS. 42A–B: (A) IFN-gamma secreted by spleen cells (SPC) cultured with porcine islets, transplanted NODs—not rejecting. (B) IFN-gamma secretion by spleen cells (SPC) cultured with porcine islets, transplanted NODs—rejecting.

FIGS. 43A–B: (A) IL-4 present in peritoneal fluid on sacrifice (sac) day, transplanted NODs. (B) IL-4 present in peritoneal fluid on sacrifice (sac) day, untransplanted mice.

FIGS. 44A–B: (A) IL-4 secreted by spleen cells (SPC) cultured with porcine islets, transplanted NODs—not rejecting. (B) IL-4 secreted by spleen cells (SPC) cultured with porcine islets, transplanted NODs—rejecting.

FIGS. 45A–B: (A) IL-5 present in peritoneal fluid on sacrifice (sac) day, transplanted NODs. (B) IL-S present in peritoneal fluid on sacrifice (sac) day, untransplanted mice.

FIGS. 46A–B: (A) IL-10 present in peritoneal fluid on sacrifice (sac) day, transplanted NODs. (B) IL-10 present in peritoneal fluid on sacrifice (sac) day, untransplanted mice.

FIGS. 47A–B: (A) IL-10 secreted by spleen cells (SPC) cultured with porcine islets, transplanted NODs—not rejecting. (B) IL-10 secreted by spleen cells (SPC) cultured with porcine islets, transplanted NODs—rejecting.

FIGS. 48A–B: (A) IL-12 present in peritoneal fluid on sacrifice (sac) day, transplanted NODs. (B) IL-12 present in peritoneal fluid on sacrifice (sac) day, untransplanted mice.

FIGS. 49A–B: (A) IL-12 secreted by spleen cells (SPC) cultured with porcine islets, transplanted NODs—not rejecting. (B) IL-12 secreted by spleen cells (SPC) cultured with porcine islets, transplanted NODs—rejecting.

FIGS. 50A–B: (A) TNF-alpha (TNF-α) present in peritoneal fluid on sacrifice (sac) day, transplanted NODs. (B) TNF-alpha (TNF-α) present in peritoneal fluid on sacrifice (sac) day, untransplanted mice.

FIGS. 51A–B: (A) TNF-alpha (TNF-α) secreted by spleen cells (SPC) cultured with porcine islets, transplanted NODs—not rejecting. (B) TNF-α secreted by spleen cells (SPC) cultured with porcine islets, transplanted NODs—rejecting.

FIGS. 52A–B: (A) TGF-beta (TGF-β) present in peritoneal fluid on sacrifice (sac) day, transplanted NODs. (B) TGF-beta (TGF-β) present in peritoneal fluid on sacrifice (sac) day, untransplanted mice.

FIGS. 53A–B: (A) TGF-beta (TGF-β) secreted by spleen cells (SPC) cultured with porcine islets, transplanted NODs—not rejecting. (B) TGF-beta (TGF-β) secreted by spleen cells (SPC) cultured with porcine islets, transplanted NODs—rejecting.

FIGS. 54A–B: (A) $NO_2$ produced by spleen cells (SPC) cultured with pig islets, transplanted NODs—not rejecting. (B) $NO_2$ produced by spleen cells (SPC) cultured with pig islets, transplanted NODs—rejecting.

Figure 55A:
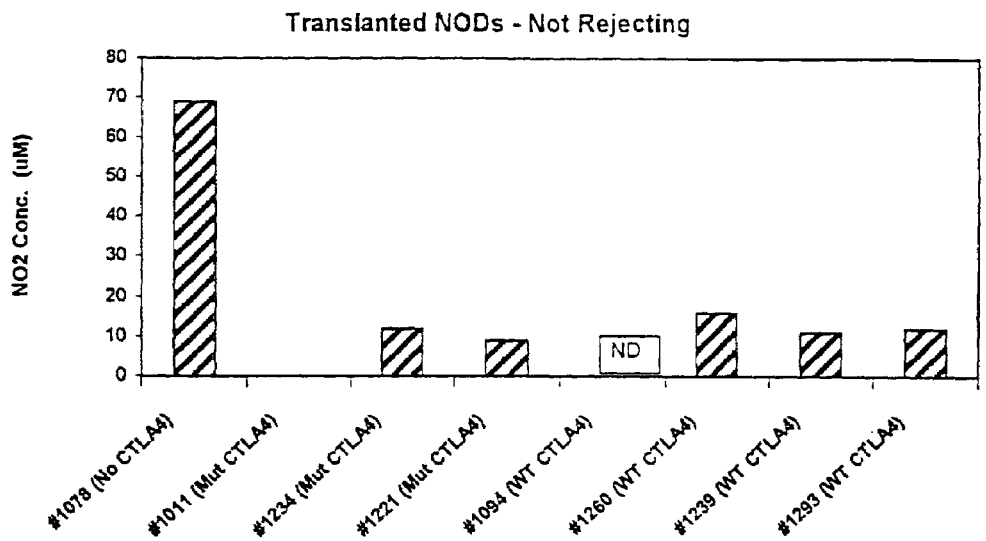
Figure 55B:
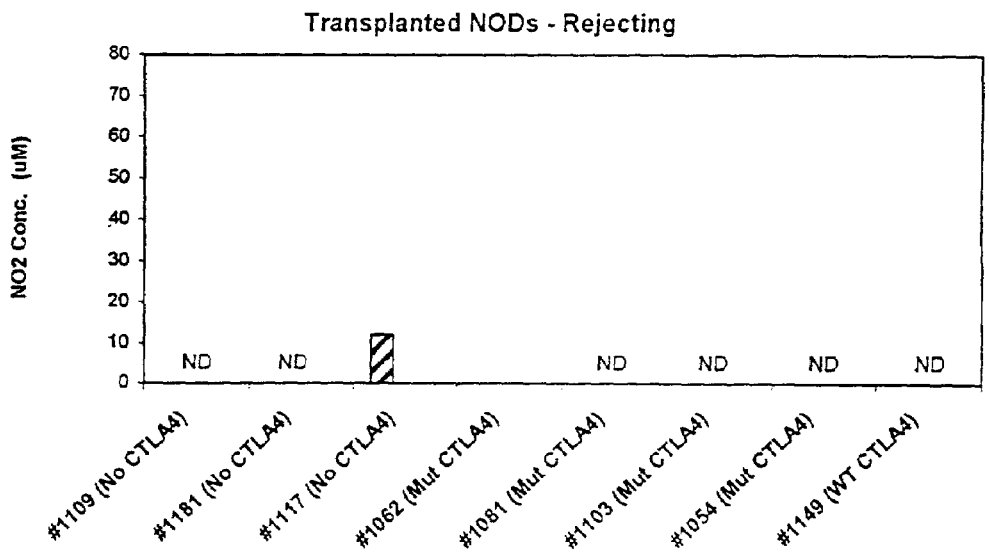

FIGS. 55A–B: (A) $NO_2$ produced by peritoneal exudate cells (PECs), i.e. from the "belly", after 96 hr in culture with original encapsulated porcine islets, transplanted NODs—not rejecting. (B) $NO_2$ produced by (PECs) after 96 hr in culture with original encapsulated porcine islets, transplanted NODs—rejecting.

Figure 56:
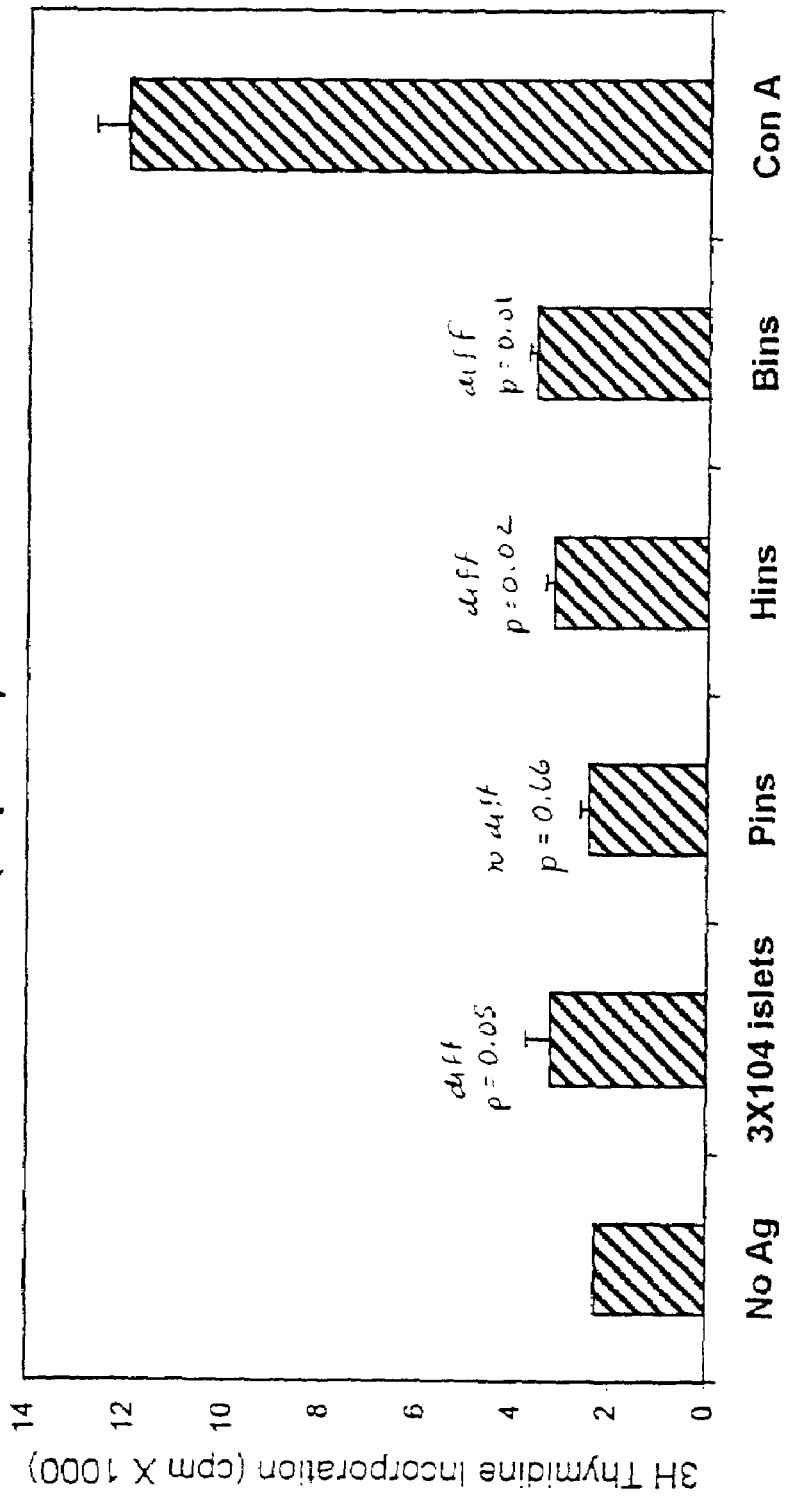

FIG. 56: Proliferation of spleen cells (SPC) from NOD #1335 to pig islets or insulin (Expt 288)

FIG. 57A–B: (A) Proliferation of spleen cells (SPC) from NOD #1335 to pig islet cells in vitro (Expt 288); (B) Proliferation of spleen cells (SPC) from NOD #1335 (Expt 288).

FIG. 58: $NO_2$ Production by cells from NOD #1335 (Expt 288).

DETAILED DESCRIPTION OF THE INVENTION

This invention provides a method of inhibiting viable cells transplanted into a subject from being destroyed by the subject's immune system which comprises: a) containing the viable cells, or tissue comprising the viable cells, prior to transplantation within a device comprising a semipermeable membrane; and b) treating the subject with a substance which inhibits an immune-system costimulation event in an amount effective to inhibit the subject's immune system from responding to said contained cells or tissue.

As used herein, an "immune-system costimulation event" is an interaction between an APC and a T-cell required in conjunction with the binding of an MHC-bound antigen on the surface of the APC to the T cell receptor. As used herein, APCs are "antigen presenting cells", which are known to those of skill in the art. Immune-system costimulation events include any specific binding of an APC cell-surface molecule (other than an MHC-bound antigen) to a specific ligand on a T cell. Such specific bindings include, but are not limited to, binding of a B7 molecule (present on the surface of an APC) to a CTLA4 receptor or a CD28 receptor on the surface of a T cell, and binding of a CD40 molecule (present on the surface of an APC) to GP39 (on the surface of a T cell).

Substances which inhibit immune-system costimulation events are known in the art and include, but are not limited to, T cell or APC cell-surface-molecule analogs, such as MR1 (which blocks the binding of CD40 expressed on the surface of an APC to GP39 expressed on the surface of a T cell), or CTLA4 (which blocks the binding of a B7 molecule to a CD28 receptor or a CTLA4 receptor).

In one embodiment of the method for inhibiting destruction of viable transplanted cells described herein, the substance which inhibits an immune-system costimulation event is CTLA4. The term CTLA4, for purposes of this invention, is meant to indicate any proteinaceous construct which comprises an amino acid sequence which is the same as or sufficiently the same as the amino acid sequence of the CTLA4 receptor such that the proteinaceous construct is capable of binding to a B7 molecule, thereby blocking the B7 molecule from binding to a CTLA4 receptor on a T cell. Proteinaceous constructs are well known in the art and indicate any molecule which comprises amino acid moieties linked to one another by peptide bonds; including peptides, polypeptides, and molecules comprising peptide and/or peptide subunits. Thus, the term CTLA4 includes, but is not limited to, molecules expressed by the gene encoding the B7-binding site of the CTLA4 receptor in genetically engineered cells, molecules expressed by mutants of the gene encoding the B7-binding site of the CTLA4 receptor which molecules are capable of binding to a B7 molecule, and synthetic amino acid chains having an amino acid sequence which is the same as or sufficiently the same as the amino acid sequence of the CTLA4 receptor such that they are able to bind to B7. CTLA4 also includes soluble CTLA4 comprising the extracellular binding domain of the CTLA4 receptor, such as CTLA4Ig. Accordingly, the term CTLA4 for purposes of this invention also includes CTLA4Ig, i.e. a recombinant soluble fusion protein which combines the extracellular binding domain of the CTLA4 receptor with the constant region of $IgG_1$.

In an embodiment of this invention, the substance which inhibits an immune-system costimulation event also alters the cytokine profile of the subject so as to protect the contained cells or tissue from the subject's immune system. The term "cytokine profile" means the type and quantity of each type of cytokine produced in a subject at a given time. Cytokines are proteins which have an immune effect and which are released by white blood cells. Examples of cytokines include, but are not limited to interferon (such as gamma-interferon), tumor necrosis factor, interleukin (IL) 1, IL-2, IL-4, IL-6, and IL-10. For example, the substance may be a substance which increases the production of gamma-interferon in the subject. An example of a substance which alters the cytokine profile of a subject so as to protect contained cells or tissue grafted into the subject is CTLA4Ig.

In another embodiment, the substance which inhibits an immune-system costimulation event binds complement. Substances which bind complement favor prolonged survival of contained cells or tissue grafted into the subject. An example of a substance which binds complement is CTLA4Ig.

In another embodiment of this invention, the substance which inhibits an immune-system costimulation event does not alter the cytokine profile of the subject so as to protect the contained cells or tissue from the subject's immune system. The term "cytokine profile" means the type and quantity of each type of cytokine produced in a subject at a given time. Cytokines are proteins which have an immune effect and which are released by white blood cells. Examples of cytokines include, but are not limited to interferon (such as gamma-interferon), tumor necrosis factor, interleukin (IL) 1, IL-2, IL-4, IL-6, and IL-10. For example, the substance may be a substance which increases the production of gamma-interferon and IL-2 in the subject. An example of a substance which does not alter the cytokine profile of a subject so as to protect contained cells or tissue grafted into the subject is CTLA4Ig. In an embodiment, the substance and the containing of the viable cells within the device comrising the semipermeable membrane prevents host immune cell proliferation in the subject. In an embodiment of the above-described method the device comrising the semipermeable membrane is a hollow, fiber, a disc, or a sphere. In a further embodiment of the above-described method the device comrising the semipermeable membrane is a microcapsule.

This invention also provides a method of inhibiting viable cells transplanted into a subject from being destroyed by the subject's immune system which comprises: a) containing the viable cells, or tissue comprising the viable cells, prior to transplantation within a device comprising a semipermeable membrane; and b) treating the subject with CTLA4 in an amount effective to inhibit the subject's immune system from responding to said contained cells or tissue.

Devices comprising a semipermeable membrane useful for transplantation of viable cells or tissue are well-known to those of ordinary skill in the art, and any such device may be used in the subject invention. Devices useful for the subject invention may be comprised of various materials and may be formed into various shapes, such materials and shapes being well known in the art. Any particular device for an application of this invention is selectable based on factors including, but not limited to, the biocompatibility of the material with the subject, the site of transplantation, whether the transplantation is intravascular or extravascular, the method of transplantation, availability, and economy. Examples of suitable shapes for devices include, but are not limited to, hollow fibers, discs, and spheres. Suitable materials include, but are not limited to, agarose hydrogel, plastics, polymers, and polyamino acids. A device may be comprised of more than one material.

In a preferred embodiment of the subject invention, the device is a microcapsule. As used herein, the term "microcapsule" means any polyamino acid spherical capsule. Microcapsules as defined herein and their methods of manufacture are well known in the art and include, but are not limited, single layered, double layered, or multilayered polyamino acid spheres, as well as polyamino acid spheres comprising a layer or more than one layer of alginate.

The viable cells or the tissue comprising the viable cells in the aforementioned method of this invention may be derived from any source for viable cells. In one embodiment, the viable cells or the tissue are derived from a xenogeneic donor, i.e. a subject which is a different species from the subject into which the viable cells or tissue are transplanted. In another embodiment, the viable cells or the tissue comprising the viable cells are derived from an allogeneic donor, i.e. a subject which is of the same species as the subject into which the viable cells or tissue are transplanted. In a further embodiment, the viable cells or the tissue comprising the viable cells are derived from the subject into which they are transplanted, i.e. they are, inter alia, obtained from the subject, contained within the device, and transplanted back into the subject. Viable cells obtained from the subject may, for example, be genetically engineered after they are obtained and before they are transplanted back into the subject.

The viable cells or tissue comprising viable cells may be obtained from any donor. In one embodiment, the donor is a mammal. Such a mammalian donor may, for example, be a calve, a pig, a rabbit, a rat, a mouse, or a human. The viable cells or tissue comprising viable cells may be obtained from a mammalian neonate, such as a neonatal pig.

The subject of the invented method described herein may be any subject into which transplantation of viable cells is desired. In one embodiment, the subject is a human. If the subject is a human, the viable cells, or tissue containing them, are in one embodiment derived from a mammal, for example a human.

In another embodiment, the subject is a domesticated animal. As used herein, a domesticated animal is any animal subjected to human intervention. Domesticated animals include, for example, farm animals which are raised by humans and which are used as a resource for products for human consumption. Such products include, but are not limited to, meat, milk, and leather. Examples of domesticated animals include, but are not limited to, cows, pigs, sheep, horses, and chickens. Domesticated animals useful in applications of the subject invention may be adults, infants, or domesticated animals at any other developmental stage.

In one embodiment wherein the subject is a domesticated animal, the viable cells comprise cells which secrete a hormone which promotes growth in the domesticated animal. Such hormones are well known to those of ordinary skill, including hormones such as growth hormone and insulin. The viable cells secreting such a hormone are in one embodiment genetically engineered to secrete the hormone. That is they have been genetically engineered to contain the gene encoding the hormone and are capable of expressing the gene.

In the aforementioned method of this invention, the viable cells in one embodiment comprise cells which secrete a biologically active substance. The term "biologically active substance" as used herein means any substance which is capable of eliciting a physiological response in a subject. The biologically active substance may illicit a response in the subject into which the cells producing it are transplanted. Cells which secrete biologically active substances are well known in the art, and any such cells may be used in the subject invention.

In one embodiment, the cells which secrete a biologically active substance are endocrine cells. Endocrine cells are well known to those of ordinary skill in the art and include, but are not limited to, insulin-producing cells, hepatocytes, parathyroid cells, and pituitary cells. In another embodiment, the cells which secrete a biologically active substance are neuroectodermal cells. Neuroectodermal cells are also well known in the art, and include, but are not limited to, adrenal cells and lymphocytes.

In another embodiment, the cells are genetically engineered to secrete a biologically active substance. For example, the cells may be genetically engineered to secrete a biologically active substance useful for treating the subject into which they are transplanted. Thus, the subject method provides a novel, useful, and advantageous drug delivery system for treatment of subjects afflicted with conditions including, but not limited to, cancer and HIV infection. If the subject is afflicted with cancer, the transplanted viable cells may, for example, be genetically engineered to secrete Interleukin-2, a cytokine, or a lymphokine. If the subject is infected with HIV, the transplanted viable cells may, for example, be genetically engineered to secrete a substance which stimulates lymphocyte production in the subject, such as a T cell growth factor or the HIV T cell receptor.

In the method of the subject invention, the permeability of the semipermeable membrane of the device is determined based on factors well known in the art, for example, the size of the cells or tissue being contained, the size of any substances needed to permeate the membrane in order to sustain the cells or tissue, and the size of any biologically active substances secreted by the cells which are desired to permeate from the device. In one embodiment, the semipermeable membrane is impermeable to lymphocytes. In another embodiment, the semipermeable membrane is impermeable to lymphocytes and immunoglobulins. Using a semipermeable membrane which is impermeable to immunoglobulins and/or lymphocytes prevents contact between the immunoglobulins and/or lymphocytes of the subject and the contained viable cells, and thereby prevents destruction of the contained cells which would result from such contact.

Any suitable method of treatment may be used in the subject invention to treat the subject with the substance which inhibits an immune-system costimulation event, and such methods are well-known in the art. For example, the substance may be administered by injection to the subject in the form of a pharmaceutically acceptable composition. If the substance is CTLA4, CTLA4Ig may be directly administered to the subject, or in another embodiment, cells genetically engineered to secrete CTLA4, that is cells which have been genetically engineered to contain a gene encoding a molecule capable of binding to a B7 molecule and to express that molecule, may be transplanted into the subject.

In another embodiment of the invention, treatment of the subject with the substance comprises transplanting into the subject cells genetically engineered to secrete the substance. If cells genetically engineered to secrete the substance are transplanted into the subject, such cells may themselves be contained within a device comprising a semipermeable membrane prior to transplantation. In different embodiments, the semipermeable membrane of the device containing the cells secreting the substance is impermeable to immunoglobulins and/or lymphocytes, thereby preventing destruction of these cells which would otherwise result from such contact.

In the aforementioned embodiments, treatment with the substance may occur before, after, of contemporaneously with transplantation of the viable cells or tissue.

In another embodiment of the subject invention, treating the subject with the substance comprises containing cells genetically engineered to secrete the substance within the device containing the viable cells or tissue prior to transplantation.

In a further embodiment of the invention, treating the subject with the substance comprises genetically engineering the viable cells transplanted into the subject to secrete the substance prior to transplantation.

The amount of the substance effective to inhibit the subject's immune system from responding to said contained cells or tissue is determined by factors well-known to those of skill in the art, including, but not limited to, the amount of viable cells or tissue transplanted into the subject, and the size and weight of the subject.

Inhibiting the subject's immune system from responding to the contained viable cells or tissue by the method of the subject invention involves an inhibition of immunoglobulin production in the subject and an inhibition of macrophage activation in the subject. Such immunoglobulins and activated macrophages would otherwise be capable of reacting with, and destroying, the contained viable cells or tissue.

This invention also provides a method of treating diabetes in a subject which comprises: a) containing viable insulin-producing cells, or tissue comprising viable insulin-producing cells, within a device comprising a semipermeable membrane so as to obtain contained viable insulin-producing cells; b) transplanting contained viable insulin-producing cells obtained in step (a) into the subject in an amount effective to treat diabetes in the subject; and c) treating the subject with a substance which inhibits an immune-system costimulation event in an amount effective to inhibit the subject's immune system from responding to an amount of contained viable insulin-producing cells according to step (b).

Substances which inhibit an immune-system costimulation event are known in the art, and any such substance may be used in the method for treating diabetes described herein. Substances which inhibit an immune-system costimulation event which may be used in the subject method for treating diabetes are described above. In one embodiment, the substance is CTLA4.

The viable insulin-producing cells, or tissue comprising viable insulin-producing cells, may be obtained from any known source for insulin-producing cells or tissue comprising insulin-producing cells.

In one embodiment of the subject invention, viable insulin-producing cells are derived from pancreatic islet tissue. In another embodiment, the viable insulin-producing cells comprise cells which have been genetically engineered prior to transplantation to secrete insulin. The viable cells or tissue may be derived from a xenogeneic donor, an allogeneic donor, or they may be derived from the subject prior to transplantation. If the cells are derived from the subject, in one embodiment, they are genetically engineered to produce insulin after they have been removed from the subject, prior to being transplanted back into the subject.

The viable insulin-producing cells or tissue comprising viable insulin-producing cells, such a pancreatic islet tissue, may be obtained from any donor. In one embodiment, the donor is a mammal. Such a mammalian donor may, for example, be a calve, a pig, a rabbit, a rat, a mouse, or a human. The viable insulin-producing cells or tissue comprising viable insulin-producing cells, such as pancreatic islet tissue, may be obtained from a mammalian neonate, such as a neonatal pig. In one embodiment, the viable insulin-producing cells or tissue comprising viable insulin-producing cells used in the subject invention comprises neonatal porcine (pig) pancreatic cells.

The subject of the invented method described herein may be any subject into which transplantation of viable cells is desired. In one embodiment, the subject is a human. If the subject is a human, the viable cells, or tissue containing them, are in one embodiment derived from a mammal, for example a human.

Devices comprising a semipermeable membrane are well-known to those of ordinary skill as described above, and any such device may be used in the subject method of treating diabetes. In different embodiments of the method, the device is a hollow fiber, a disk, and a sphere. In another embodiment of the method, the device is a microcapsule as described above.

The method of treating diabetes described herein may be applied to any subject for whom diabetes treatment is desired. In one embodiment of the invented method for treating diabetes in a subject, the subject is afflicted with insulin-dependent diabetes mellitus (IDDM). In another embodiment of the method, the subject is a mammal, for example a human.

The amount of contained viable insulin-producing cells transplanted into the subject effective to treat diabetes in the subject depends on factors known to those of ordinary skill, including, but not limited to, factors such as the weight of the subject, and the severity of the diabetes.

The permeability of the semipermeable membrane of the device in the subject method of treating diabetes is determined by factors known to those of ordinary skill, including those factors for determining permeability described above.

In different embodiments of the method, the semipermeable membrane is impermeable to immunoglobulins and/or lymphocytes.

Treatment of the subject with the substance which inhibits an immune-system costimulation event in the subject method of treating diabetes includes those methods of treatment described above. If the substance is CTLA4, treatment may comprise administering CTLA4Ig to the subject, for example by injecting CTLA4Ig into the subject. Treatment with the substance may, as described above, comprise transplanting into the subject cells genetically engineered to secrete the substance. Such genetically engineered cells may themselves be contained within a device comprising a semipermeable membrane prior to transplantation. If treatment with the substance comprises transplanting into the subject cells genetically engineered to secrete the substance contained within a device comprising a semipermeable membrane, the device is in different embodiments impermeable to immunoglobulins and/or lymphocytes.

In the aforementioned methods of treating the subject with a substance, such as CTLA4, capable of inhibiting an immune-system costimulation event, treatment may occur before, after, or contemporaneously with transplantation of the contained viable insulin-producing cells into the subject.

In another embodiment of the subject method of treating diabetes, treating the subject with the substance capable of inhibiting an immune-system costimulation event comprises containing cells genetically engineered to secrete the substance within the device containing the viable insulin-producing cells or tissue prior to transplantation.

In another embodiment of the subject method of treating diabetes, treating the subject with the substance comprises genetically engineering the viable insulin-producing cells to secrete the substance prior to transplantation.

Inhibiting the subject's immune system from responding to contained viable insulin-producing cells or tissue by the subject method of treating diabetes involves an inhibition of immunoglobulin production and of macrophage activation in the subject which would otherwise react with and lead to the destruction of the viable insulin-producing cells or tissue.

This invention will be better understood from the "Experimental Details" section which follows. However, one skilled in the art will readily appreciate that the specific methods and results discussed therein are not intended to limit, and rather merely illustrate, the invention as described more fully in the claims which follow thereafter.

Experimental Details

Improvements in Microcapsule Design

Figure 1:
FIG. 1: Encapsulated Lewis rat islet, day #150 after xenografting to unmodified diabetic NOD H&E. (×250). The microcapsule is a "double-wall" microcapsule.
Figure 2:
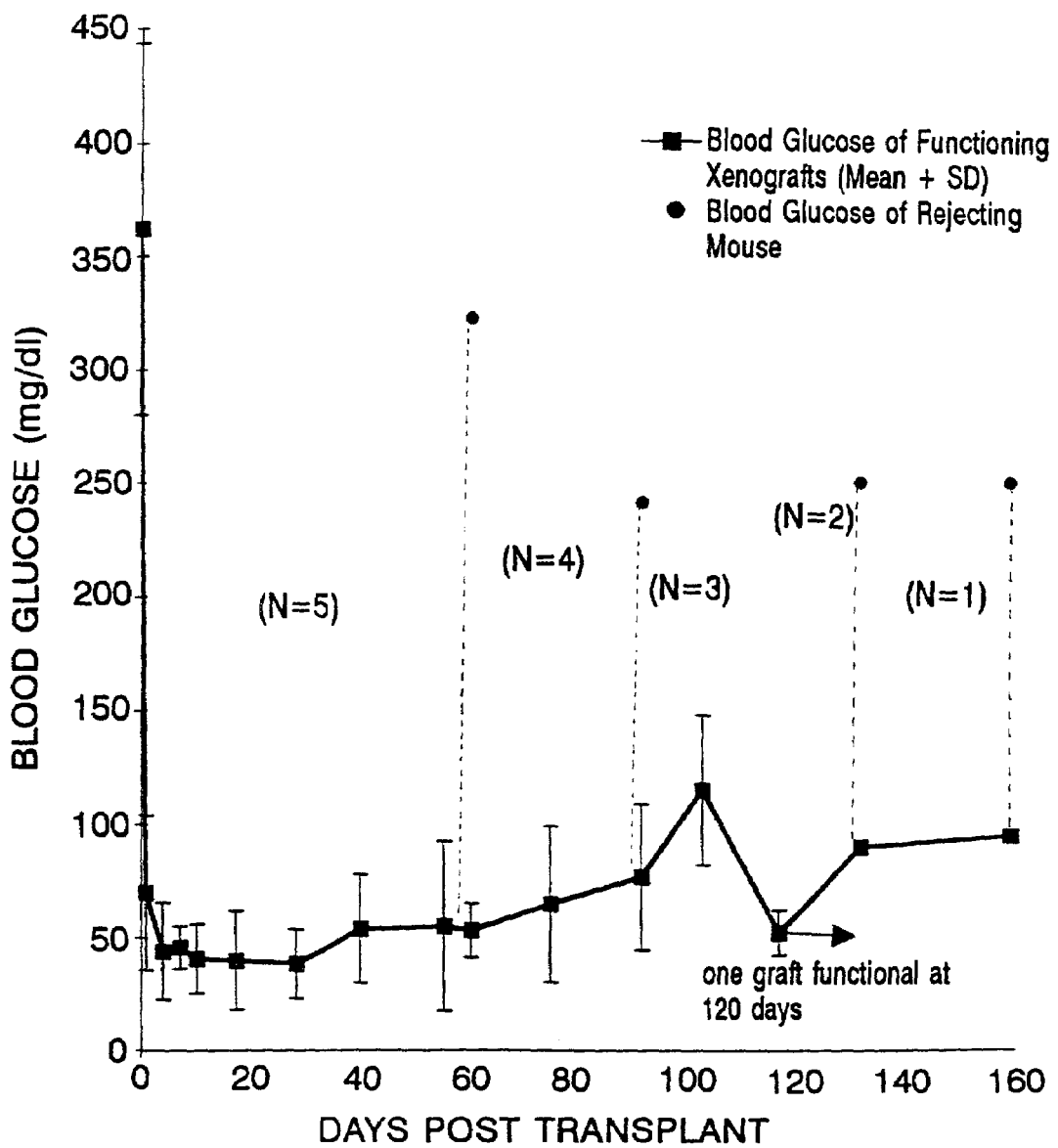
FIG. 2: Survival of islet xenograft, "double-wall" microcapsule.

An improved formulation of poly-l-lysine-alginate microencapsulation which allows nearly indefinite survival of rat islets in spontaneously diabetic NOD mice is the "double-wall" microcapsule (FIGS. 1 and 2). This double-wall microcapsule is more durable than conventional microcapsules, with fewer capsule wall defects, has a measured membrane permeability of approximately 100,000 Kd, and excludes IgG (unlike conventional design capsules, which allowed passage of IgG and 148,000 Kd fluoresceinated dextran) (9, 19, 20, 118). These data support the relevance of encapsulated islet xenografts for eventual application in humans with IDDM.

Poly-L-Lysine (PLL) Concentration Alters Permeability of PLL-Alginate Microcapsules It was postulated that microencapsulated islet xenograft survival would be influenced by microcapsule permeability. We found that microcapsule permeability may be altered by increasing or decreasing the concentration of PLL (poly-l-lysine) in the microcapsule formula. Red blood cells were encapsulated in alginate via an air jet system and then incubated with various polyamino acids including PLL. The RBCs were then lysed and hemoglobin (MW 64,500) efflux was measured spectophotometrically at 480 nm as a function of time alongside a concurrent control. Permeability coefficient was calculated according to the following formula: $(2.303*Cf*Vt*S)/(Ci*At)$, where Cl and Cf are the initial and final hemoglobin concentrations, Vt and At are the total volumes and areas of capsules respectively, and S=slope of 1n $(Ct-Cf)/(Ci-Ct)$ (119). PLL substitutions (poly-l-ornithine, alanine, aspartate and histidine) did not result in viable capsules. PLL molecular weight alterations did not effect permeability.

Figure 3:
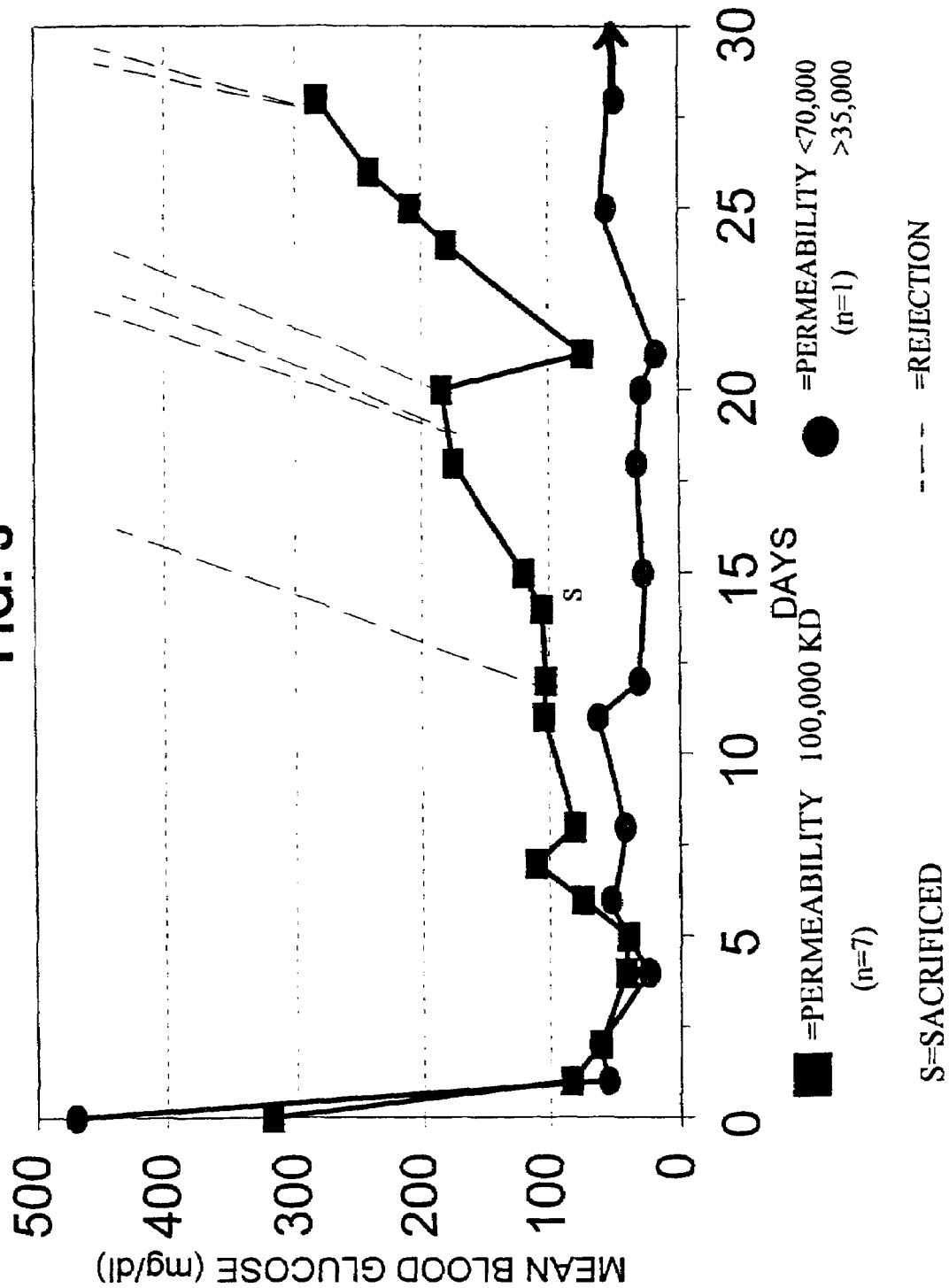
FIG. 3: Comparison of survival of rabbit islets encapsulated in microcapsules with a permeability of up to 70,000 Kd to survival of rabbit islets in microcapsules having a permeability of 100,000 Kd.

PLL concentration was the most critical factor in altering capsule diffusion. These observations are supported by the recent findings of other investigators (119). There was a thirteen fold decrease in hemoglobin efflux occurring in capsules that had a fourfold increase in PLL (see Table 1). In experiments, encapsulated rabbit islet survival in NODs is prolonged using microcapsules with permeability <70,000 Kd vs. 100,000 Kd (see FIG. 3).

TABLE 1

Increasing PLL Concentration Reduces Microcapsule Permeability to Hemoglobin

| PLL Concentration (% w/v) | 0.050 | 0.125 | 0.137 | 0.144 | 0.150 | 0.200 |
|---|---|---|---|---|---|---|
| Permeability constant (E–06 cm/sec) | 50 | 56 | 52 | 30 | 6.7 | 3.8 |

Microcapsules Prevent or Delay Host Sensitization

Figure 4:
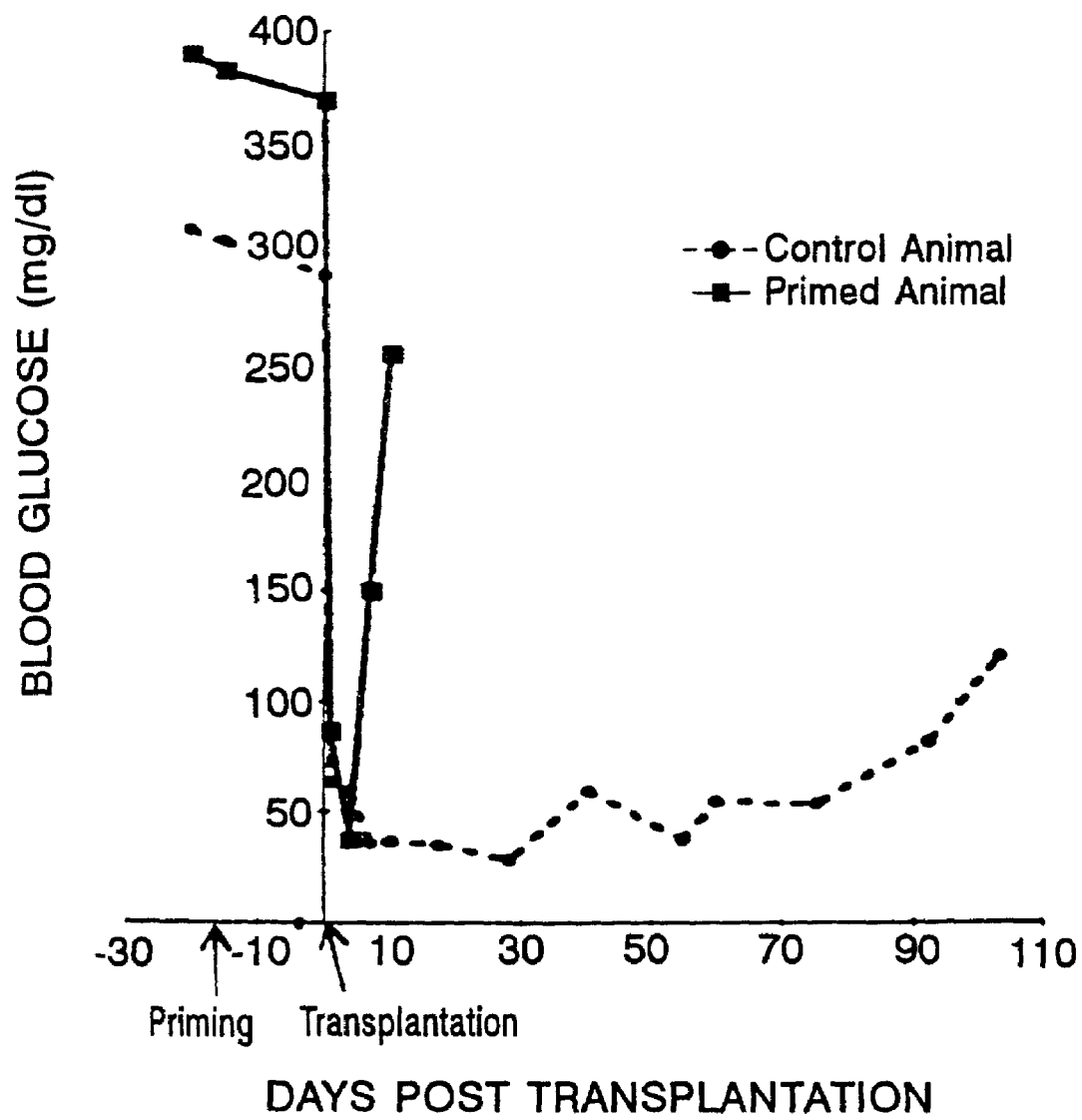
FIG. 4: Effect of Lewis rat splenocyte priming on Lewis rat-to-NOD microencapsulated islet transplantation.
Figure 5:
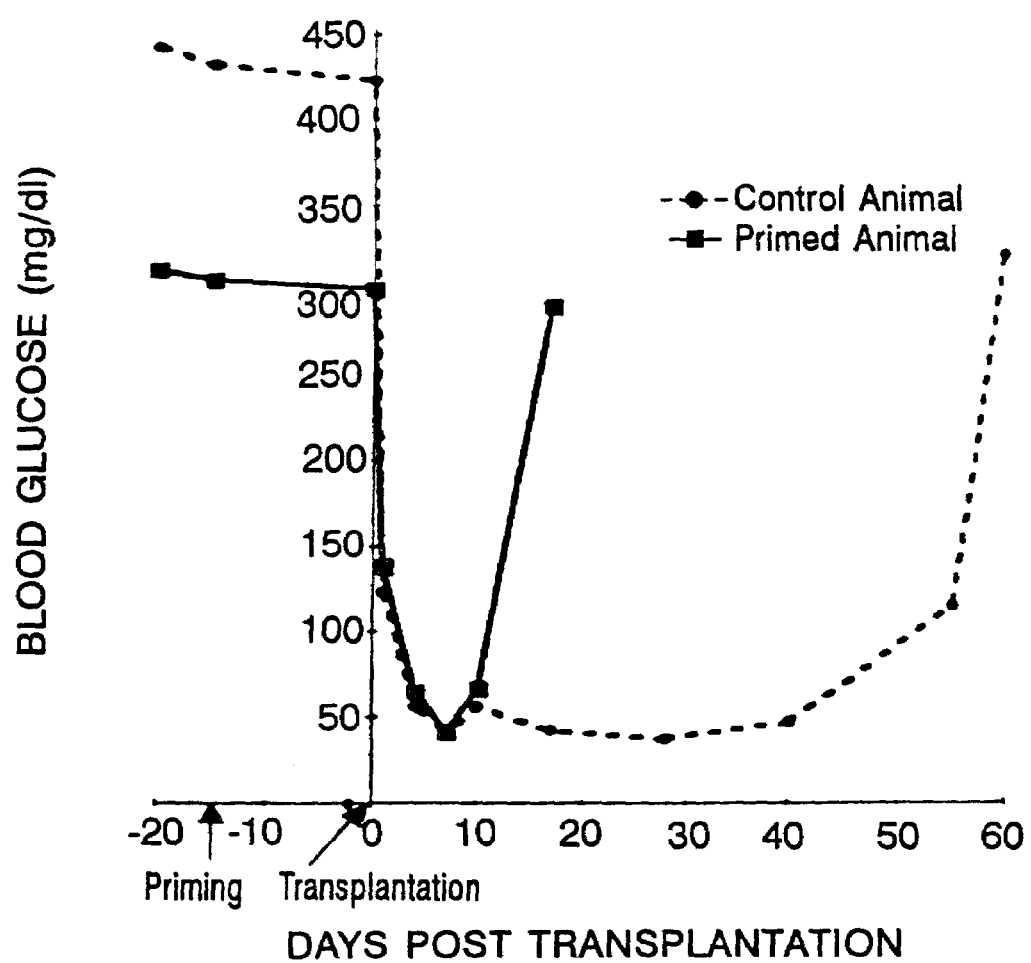
FIG. 5: Effect of Lewis rat islet priming on Lewis rat-to-NOD encapsulated islet transplantation.

To clarify the mechanism of long-term microcapsule protection of xenogeneic rat islets, experiments were performed in which paired diabetic NODs were pre-treated with saline or Lewis rat islets (200 intra-peritoneally) or $10^6$ Lewis rat splenocytes intra-peritoneally. Encapsulated Lewis islets were xenografted into presensitized and control NODs 14 days later. As shown in FIGS. 4 and 5, both islet- and splenocyte pretreatment resulted in rapid graft rejection while non-presensitized NODs accepted encapsulated islet xenografts long-term. These data suggest that a major function of microcapsules is to prevent host sensitization, rather than to protect grafts from the effector arm of the response. Thus, maneuvers which reduce islet Immunogenicity may be synergistic with islet encapsulation.

Comparisons of Encapsulated Islet Iso-, Allo- and Xenograft Survival in NODs

We have found that microencapsulation allowed islet xenograft survival in NODs of 79±15 days (N=8) (X±SE) for Lewis rat islets, vs. 20±2 days (N=7) for rabbit islets and 14±4 (N=3) for dog islets (Table 2), with similar peri-microcapsule NOD cell accumulations at rejection. NODs also rejected encapsulated, allogenic Balb/c islets in 73±31 days (N=4) and encapsulated isologous NOD islets in 44±7 days (N=4) (Table 2). However, biopsies of these allo- and isologous grafts, at rejection, have shown few host macrophages adherent to microcapsules, while free peritoneal cells (thus far not characterized) were present. Thus encapsulated islet xenograft rejection is distinct from iso- and allo-graft rejection in this model.

TABLE 2

Islet Iso-, Allo- and Xenografts in NOD Mice

| Group | Donor-Recip | Technique | Rx. | (N) | Surv (days) @ |
|---|---|---|---|---|---|
| 1 | NOD-NOD | CAP/I.P. | (−) | 4 | 44 ± 7* |
| 2 | Balb-NOD | CAP/I.P. | (−) | 4 | 6, 7, 7 |
| 3 | LeRat-NOD | CAP/I.P. | (−) | 8 | 5, 5 |
| 4 | Dog-NOD | CAP/I.P. | (−) | 3 | 73 ± 31 |
| 5 | Rabbit-NOD | CAP/I.P. | (−) | 7 | 79 ± 15 |
| 6 | Rabbit-NOD | CAP/I.P. | CyA | 4 | 14 ± 4 |
| 7 | Rabbit-NOD | CAP/I.P. | CTLA4Ig | 7 | 20 ± 2 |
| 8 | Rabbit-NOD | Splenic | CTLA4Ig | 2 | 22 ± 3 |
| 9 | Rabbit-NOD-Scid | Splenic | — | 1 | 22 ± 6 |
| 10 | Rabbit-NOD-Scid | CAP/I.P. | — | 1 | 98 ± 25# |
| 11 | LeRat-NOD-Scid | Splenic | — | 2 | 6 |
| 12 | Rabbit-NOD-Scid | Splenic | — | 1 | 119$^8$ |
| 13 | Rabbit-NOD-Scid | CAP/I.P. | — | 4 | 56 ± 11 |
| 14 | LeRat-NOD-Scid | Splenic | — | 2 | 124$^8$ |
| 15 | Calf-NOD | CAP/I.P. | (−) | 1 | 24 |
| 16 | Pig-NOD | CAP/I.P. | (−) | 2 | 6, 8 |
| 17 | Human-NOD | CAP/I.P. | (−31) | 1 | 6 |

*= $p < .002$ vs. Group 7;
@ = Mean ± SEM;
# = $P < .05$ vs. Group 7;
** = $p < .003$ vs. Group 7
CAP/I.P. = microencapsulated islet graft to peritoneal cavity;
Splenic = Nonencapsulated islets grafted beneath splenic capsule.

We have also found that microencapsulation prolongs the functional survival of islet xenografts in NODs, when compared to survival of unencapsulated islets injected into the spleen. The same is true for islet allografts and for islet isografts into NODs (Table 3).

TABLE 3

Beneficial Effect of "Double-Wall" Microencapsulation of Survival of Islet Iso-, Allo- and Xenografts in NOD Mice

| Donor-Recip | Technique | (N) | Surv (days) @ |
|---|---|---|---|
| NOD-NOD | CAP/I.P. | 4 | 44 ± 7* |
| NOD-NOD | Splenic | 3 | 6, 7, 7 |
| Balb-NOD | CAP/I.P. | 4 | 73 ± 31* |
| Balb-NOD | Splenic | 2 | 5, 5 |
| Lewis Rat-NOD | CAP/I.P. | 8 | 79 ± 15* |
| Lewis Rat-NOD | Splenic | 9 | 19 ± 3 |
| Dog-NOD | CAP/I.P. | 3 | 14 ± 4* |
| Dog-NOD | Splenic | 2 | 0, 0 |
| Rabbit-NOD | CAP/I.P. | 7 | 20 ± 2* |
| Rabbit-NOD | Splenic | 2 | 5, 6 |
| Neonatal Pig-NOD | CAP/I/P. | 8 | 27 ± 13* |
| Neonatal Pig-NOD | Splenic | 3 | 6 ± 1 |

$p < .01$ vs. splenic:
@ = Mean ± SEM.CAP/I.P. = microencapsulated islet graft to peritoneal cavity;
Splenic = Nonencapsulated islets grafted beneath splenic capsule.

Functioning and rejected encapsulated xenografts were biopsied from the peritoneal graft sites of spontaneously diabetic NOD mice, on days #4–#50 post-transplantation. Controls included normal mouse peritoneal fluid and peritoneal fluid from NOD mice bearing empty capsules or capsules with functioning (recipient normoglycemic) rat islets (20, 74). However, cell number increased dramatically at rejection on days #14 and #50. Pipetting of biopsied capsules freed adherent cells. Flow cytometric analyses revealed that 20–50% of non-adherent peritoneal cells were B220$^+$ (B cells), and that the majority of free peritoneal cells and cells adherent to microcapsules were Mac1$^+$ (20, 74). The percentages of CD4$^+$ and CD8$^+$ peritoneal cells were low (4–9%). By FACS analysis, the phenotype of peritoneal Maci cells shifted from predominantly Gran 1− to Gran 1$^+$ during rejection of xenogeneic islets in microcapsules (vs. empty capsules) (20, 74, 120). These findings were confirmed by immunocytochemistry (20, 74). In addition, immunocytochemistry documented IgG and IgM around microcapsules, and IL-1 and TNF alpha both around and within microcapsules (20, 74).

Analysis of Cytokine Messenger RNA (mRNA) in Encapsulated Islet Xenografts Biopsies from NODs To elucidate the pathogenesis of NOD destruction of encapsulated islets, mRNA was extracted from recipient NOD peritoneal cells and expression of mRNA for IL-2, IL-4, and IL-10 was studied by RT-PCR, as previously described (121). Integrity of RNA samples was assessed by inspection of northern transfer and hybridization with the probe for the 3' untranslated region of beta actin (121). IL-4 was detected in the majority of xenografts undergoing rejection. IL-10 expression was variable (Table 4). IL-2 was detected during autoimmune destruction of NOD isografts, (and in one allograft) but only rarely in rejecting xenografts (Table 4). These data suggest that the primary T cell response in rejecting encapsulated islet xenografts is "Th2-like". This interpretation is consistent with the observation that large numbers of activated macrophages and immunoglobulins are associated with rejecting encapsulated islet xenografts in NODs. Thus, it is possible that rejection of encapsulated islet xenografts is initiated by soluble, or shed, xenoantigens that are processed via the Class II pathway by host APC. These APC then activate Th2 cells via B7/CD28 dependent mechanisms. We postulate that formation of antigen-antibody complexes in the peritoneal cavity activates macrophages to release cytokines that are directly toxic to encapsulated islets.

TABLE 4

CYTOKINE mRNA IN BIOPSIES OF ENCAPSULATED XENO- ISLETS IN NOD MICE

| Islet Donor | NOD# | Sample | Day Rejected | Day Biopsied | mRNAs IL2 | IL4 | IL10 |
|---|---|---|---|---|---|---|---|
| NOD | 194 | FC | 39 | 40 | + | + | − |
|  | 291 | FC | 14 | 21 | + | − | − |
| Balb/c | 487 | Cap | 12 | 14 | + | − | − |
| Rat | 154 | Cap | 18 | 20 | − | + | − |
|  | 154 | FC | 18 | 20 | − | + | − |
|  | 58 | Cap | 34 | 38 | − | + | + |
|  | 165 | Cap | 21 | 28 | − | + | − |
|  | 54 | Cap | 136 | 143 | + | + | + |
|  | 54 | FC | 136 | 143 | + | − | − |
|  | 107 | FC | 41 | 45 | − | − | − |
|  | 453 | Cap | 132 | 134 | + | − | − |
| Canine | 141 | Cap | 17 | 24 | − | + | + |
|  | 268 | Cap | 13 | 14 | − | − | − |
|  | 268 | FC | 13 | 14 | − | − | − |
|  | 69 | FC | 18 | 24 | − | + | + |
| Rabbit | 91 | Cap | 35 | 49 | − | − | − |
|  | 91 | FC | 35 | 49 | − | + | − |
|  | 151 | Cap | 28 | 32 | + | + | − |
|  | 46 | FC | 12 | 15 | − | + | − |
|  | 55 | FC | 18 | 21 | − | + | − |
|  | 152 | FC | Funct. | 15 | − | + | − |
|  | 157 | FC | Funct. | 15 | + | − | − |
| Human | 136 | Cap | 6 | 8 | − | + | + |

Cap = Cells adherent to capsules
*F C = Free peritoneal cells
φ = RT-PCR (−) is undetachable and (+) is detachable The NOD-MHC is Necessary for Rejection of Encapsulated Islet Xenografts Both NOD and (SZN-diabetic) B10.H-$2^{g7}$ (expresses the NOD-MHC-linked disease allele) rejected encapsulated rat islets, while NOD.H-$2^b$ mice, which express all of the non-MHC-linked diabetes susceptibility genes, accepted encapsulated rat islets for >100 days (similar to B10 controls) (75). This suggests that the NOD-MHC may contribute to destructive responses against encapsulated islets which are distinct from diabetes susceptibility, since neither B10.H-$2^{g7}$ nor NOD.4-$2^b$ mice develop diabetes spontaneously (20, 75). The possibility that SZN treatment of B10.H-$2^{g7}$ mice may have initiated an autoimmune response was considered; however, 2/2 non-diabetic (no SZN treatment) B10.H-$2^{g7}$ mice rejected encapsulated rat islets (by biopsy histology, day #60) (75).

CD8$^+$ Depletion Does Not Protect Encapsulated Islet Xenografts in NODs

It was found that treatment of NOD recipients of encapsulated rabbit islets with either monoclonal antibody 53.6.7, (100 µg i.p. day −5 and then twice weekly) (anti-CD8) or cyclosporine (CyA), 30. Mg/kg, s.c., daily had no effect on graft survival (Table 2). CD8$^+$ cell depletion was confirmed by flow cytometry of NOD spleen and peritoneal cells. Biopsies of failed grafts revealed intense host cellular responses and non-viable islets within intact microcapsules. These data are consistent with prior observations, that CD4$^+$ (but not CD8) T-cells play a dominate role in non-encapsulated islet xenograft rejection (83). They also are consistent with a predominantly Th2 NOD rejection mechanism of encapsulated islet xenografts.

Figure 6:
FIG. 6: Microencapsulated dog islet, day #80, from peritoneum of NOD mouse treated with Gk1.5. H&E (×250).
Figure 7:
FIG. 7: Functioning, encapsulated rabbit islets, biopsied day #86, from peritoneum of NOD mouse, treated with CTLA4Ig. Note absence of NOD cell response and the presence of viable islets within capsule. H&E (×400).
Figure 8:
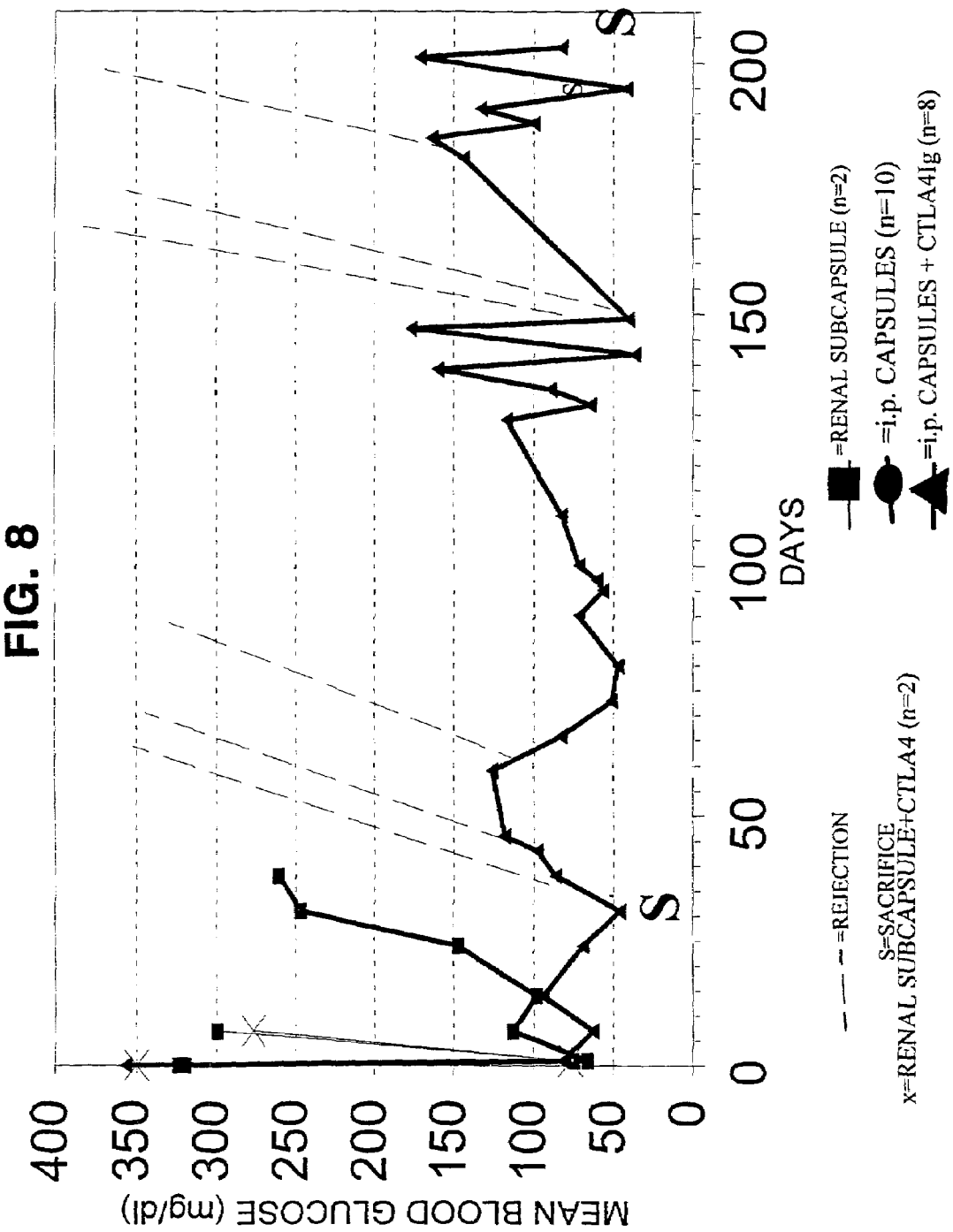
FIG. 8: Effects of microencapsulation of islets combined with CTLA4Ig treatment on islet xenografts.

Co-Stimulatory Blockade Prolongs Encapsulated Islets Xenografts in Diabetic NODs It was shown previously that inhibition of CD4$^+$ helper T-cells by administration of monoclonal antibody GK 1.5 to diabetic NOD recipients resulted in significantly increased survival (>100 days) of both encapsulated rat and dog islets (7, 84) (FIG. 6). The experiments herein show that treatment of NOD mice with CTLA4Ig (200 µg i.p. day #0, and QOD until day #90) significantly prolonged encapsulated rabbit islet survival, from 20±2 days to 98±25 days (p<0.05) (see Table 2 and FIGS. 7 and 8).

This suggests that an "indirect" pathway of antigen presentation is dominant in NOD responses to encapsulated islet xenografts. Unlike findings with human islet transplanted to SZN-diabetic mice (12), CTLA4Ig alone did not increase nonencapsulated rabbit or rat islet survival in NODs (intrasplenic or renal subcapsule) (Table 2), suggesting that encapsulation and CTLA4Ig both were required to prolong graft survival.

Figure 9:
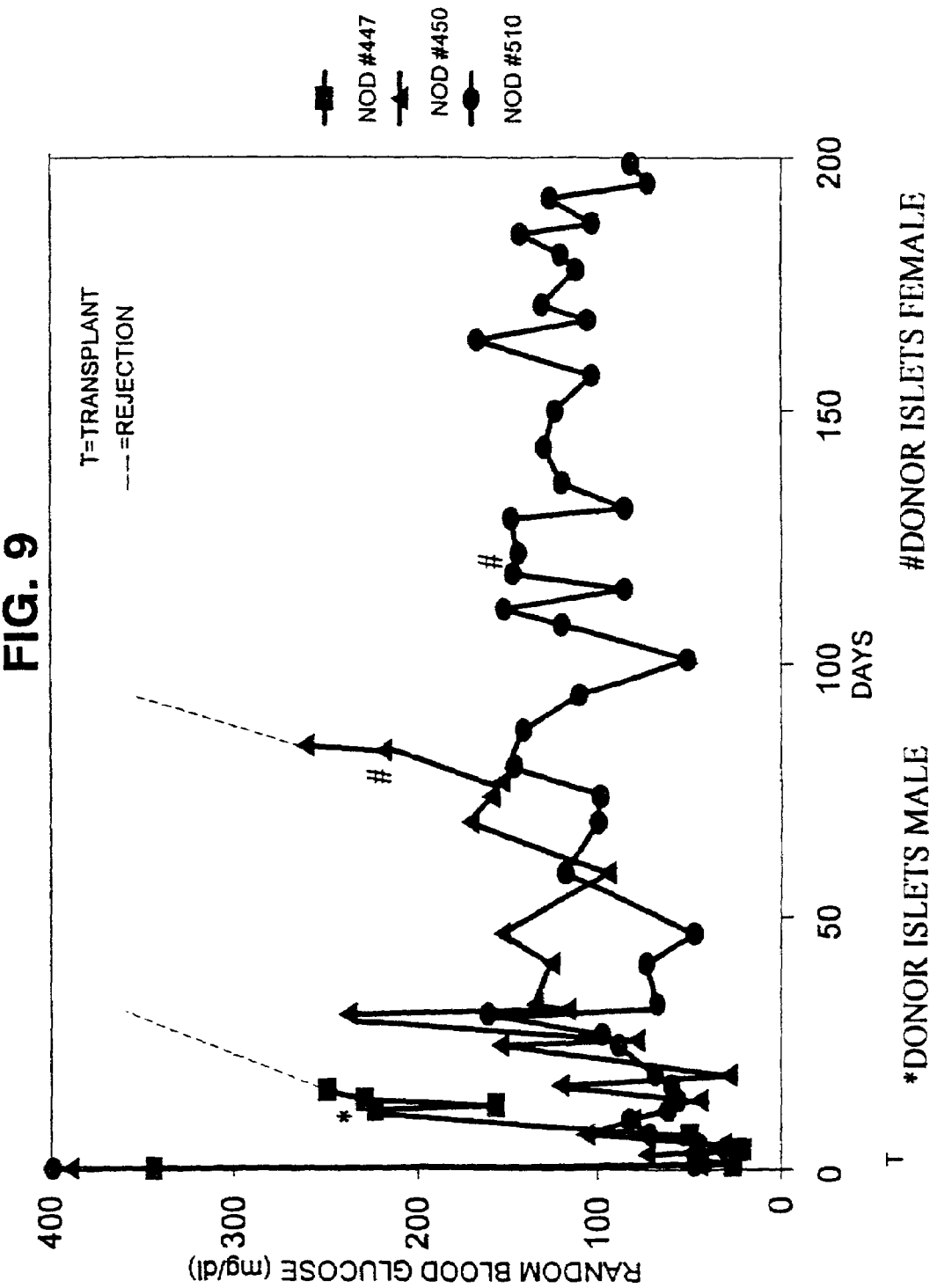
FIG. 9: Survival of microencapsulated mouse INS-CTLA4 islets transplanted into NODs. These islets express CTLA4.

Furthermore, the experiments herein show that encapsulated female islets from INSCTLA4 mice, which express CTLA4 on the beta cell insulin promoter, function long-term in NODs (see FIG. 9). Unencapsulated INSCTLA4 islets were rejected by NODs in 6–7 days. These data suggest that indefinite survival of discordant islet xenografts may be achieved by combinations of donor islet encapsulation and limited host immunomodulation. These data also support the working hypothesis that donor antigen(s) are shed from microcapsules and processed by APCs which activate CD4$^+$ T cells via B7/CD28-dependent mechanisms. In this model, CTLA4-transgenic mice secrete CTLA4, along with insulin, and CTLA4 inhibits antigen presentation. Interestingly, female mice secrete more CTLA4 than do male mice in this transgenic model (pers. Comm.).

NOD-Scid Mice Accept Rat and Rabbit Islet Xenografts Long-Term

Figure 10:
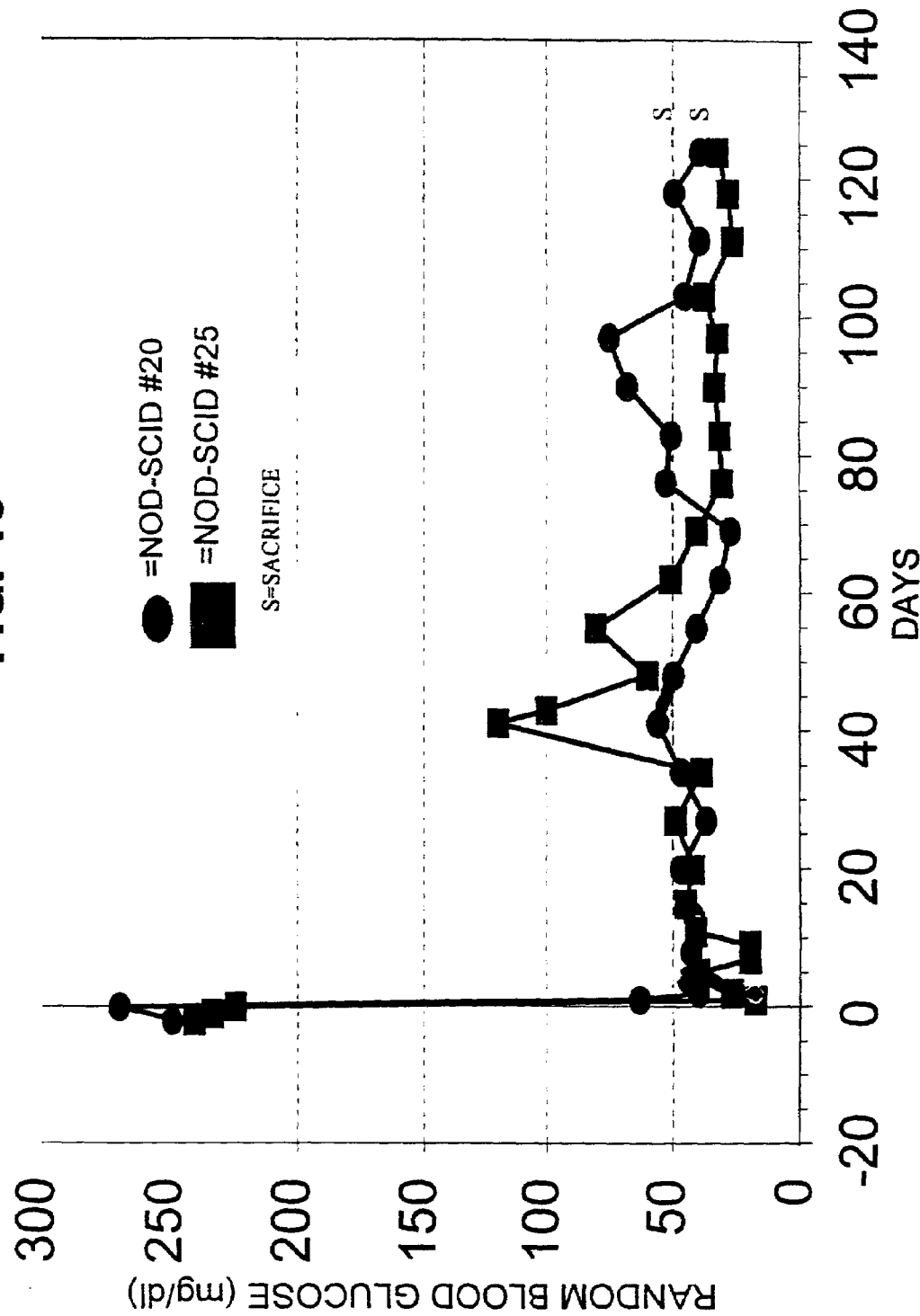
FIG. 10: Effects of transplanting rat islets into streptozotocin SZN-diabetic NOD-Scid mice.
Figure 11:
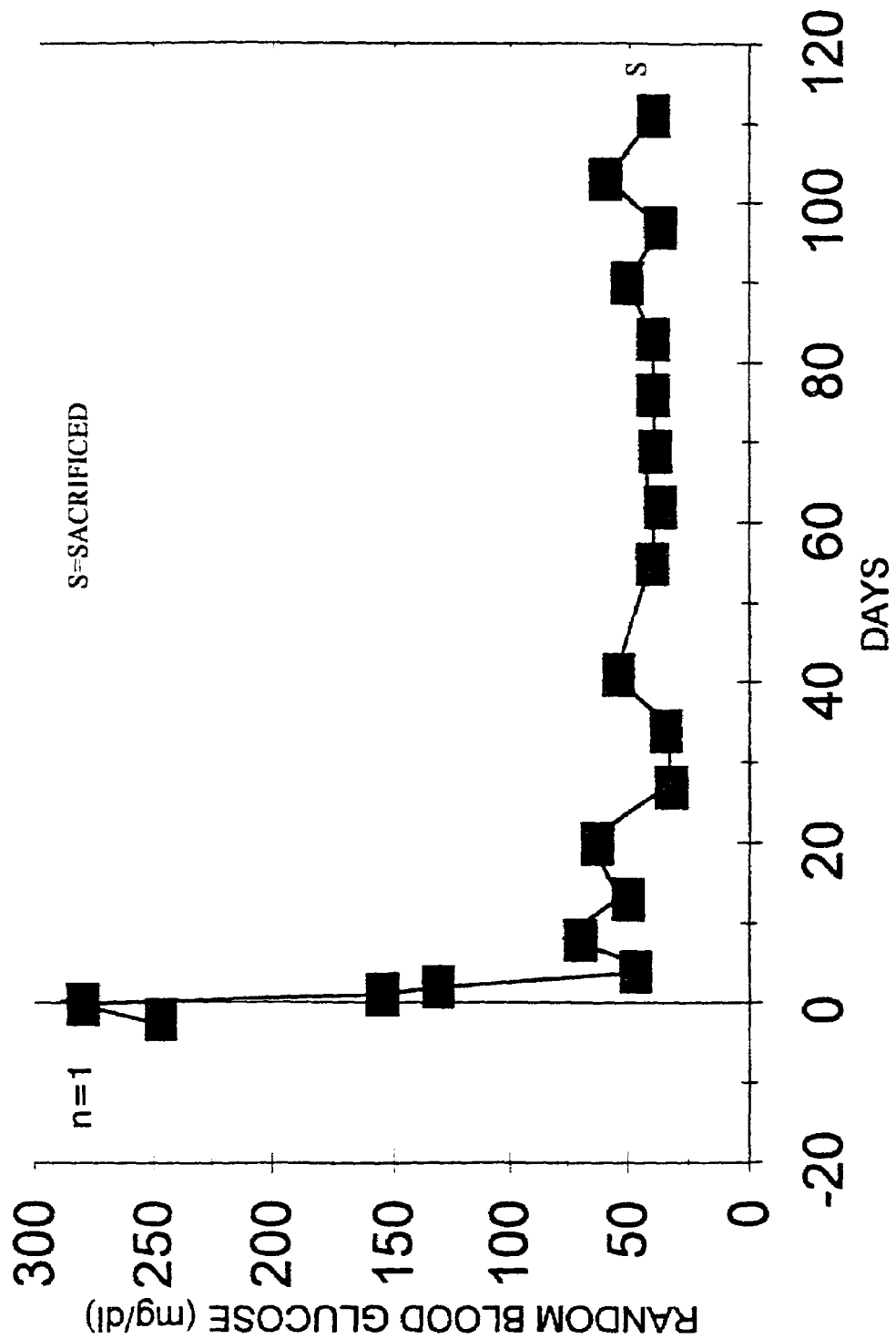
FIG. 11: Effects of transplanting rabbit islets into streptozotocin (SZN)-diabetic NOD-Scid mice.
Figure 12:
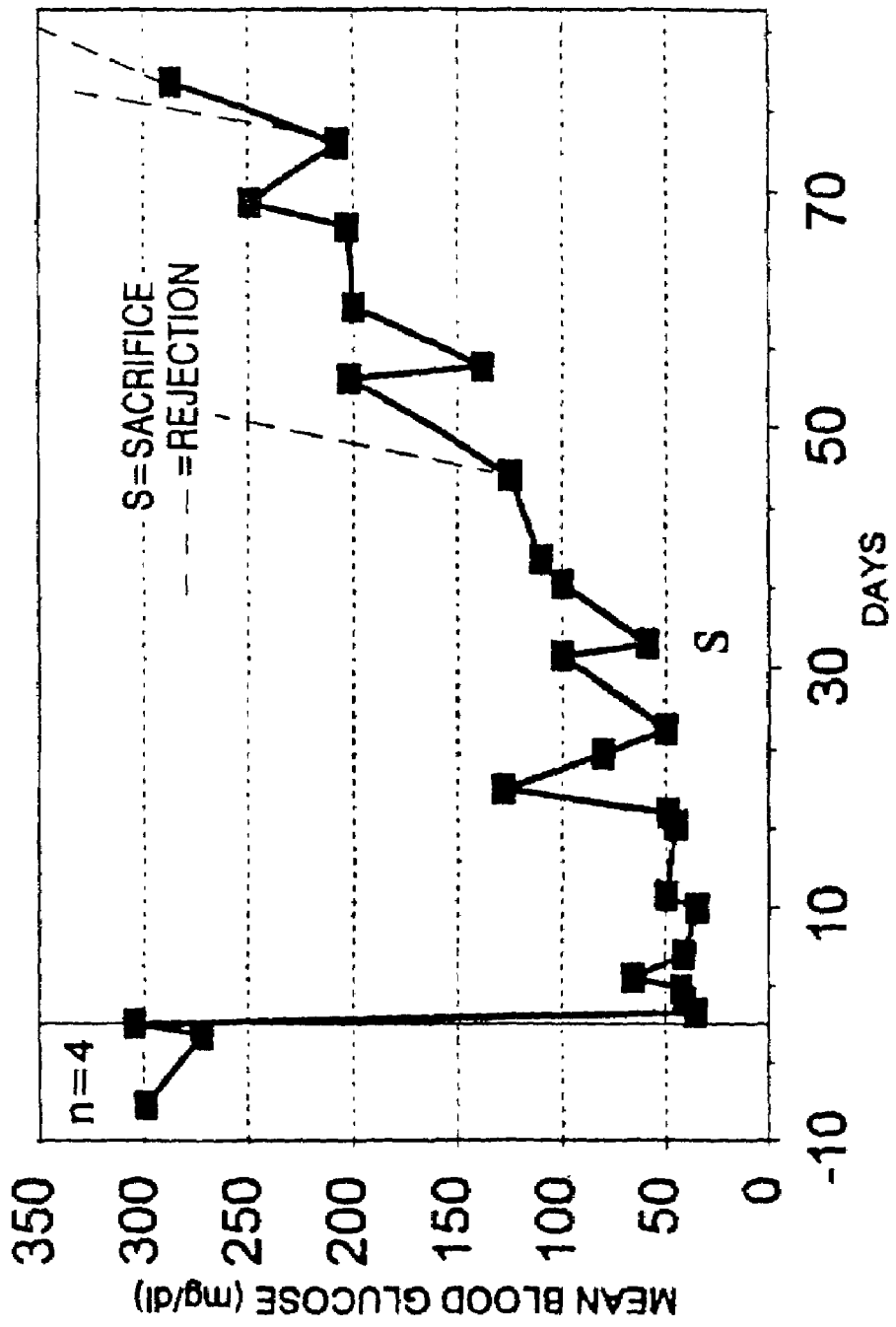
FIG. 12: Effects of transplanting microencapsulated rabbit islets into streptozotocin (SZN)-diabetic NOD-Scid mice.

These experiments demonstrate that NOD-scid mice are susceptible to MLD-SZN diabetes (30 mg/kg daily ×5); and reversal of NOD-scid diabetes with xenografts of nonencapsulated and encapsulated rat and rabbit islets for greater than 50 days is documented (see FIGS. 10, 11, and 12 and Table 2). Thus, the NOD-scid mice will serve as a good recipient model for the transfer of antibodies and/or T cells for studies of the mechanisms by which encapsulated islets are rejected. We noted recurrent hyperglycemia in 3/4 NOD-scids receiving microencapsulated rabbit islets, on days #51, #68, and #70. Biopsies revealed disrupted capsules and minimal cellular failure for technical reasons, since empty microcapsule controls done concurrently, showed broken microcapsules (in 1/3) and intact microcapsules (in 2/3) at day #50.

Costimulation Blockade with CTLA4Ig

Method:

Adult New Zealand rabbit islets were isolated by duct-injection, collagenase digestion. Rabbit islets (approx. 2000) were encapsulated in double-wall, poly-l-lysine-alginate microcapsules and xenografted intraperitoneally in NODs, as previously reported (7, 20). Controls received approximately 2000 unencapsulated rabbit islets xenografted beneath the splenic or renal capsule, as previously described (7, 20).

Murine CLTA4Ig, provided by Bristol-Myers-Squibb, Seattle, Wash., was administered at 200 ug intraperitoneally (i.p.), day-1 and then Q.O.D. for 14 or 92 days, or until graft rejection.

Controls included NODs receiving identically encapsulated rabbit islets (i.p), and given no additional treatments, cyclosporine 30 mg/kg s.c., day-1, and then daily, or monoclonal anti-CD8 antibody #53.6.7.7 (A.T.C.C.), 100 µg i.p. day−5, +2, and then weekly.

Biopsies of long-term functioning peritoneal microcapsules were done periodically, using metafane anesthesia and sterile technique. Removal of 100–200 microcapsules allowed histologic light microscopic studies without altering graft-related normogycemia.

At 180 days after successful encapsulated rabbit islet xenografting, splenectomy was performed on one long-term functioning, biopsy-proven, CTLA4Ig-treated NOD. These splenocytes (10$^7$) were passively transferred, intraperitoneally, to two naive diabetic NODs, which subsequently received identically encapsulated fresh rabbit islets (donor-type New Zealand, not inbred), intraperitoneally, on day 10–14 after splenocyte transfer. Statistical difference between groups were assessed by use Student's "t"-tested and by ANOVA.

Figure 13:
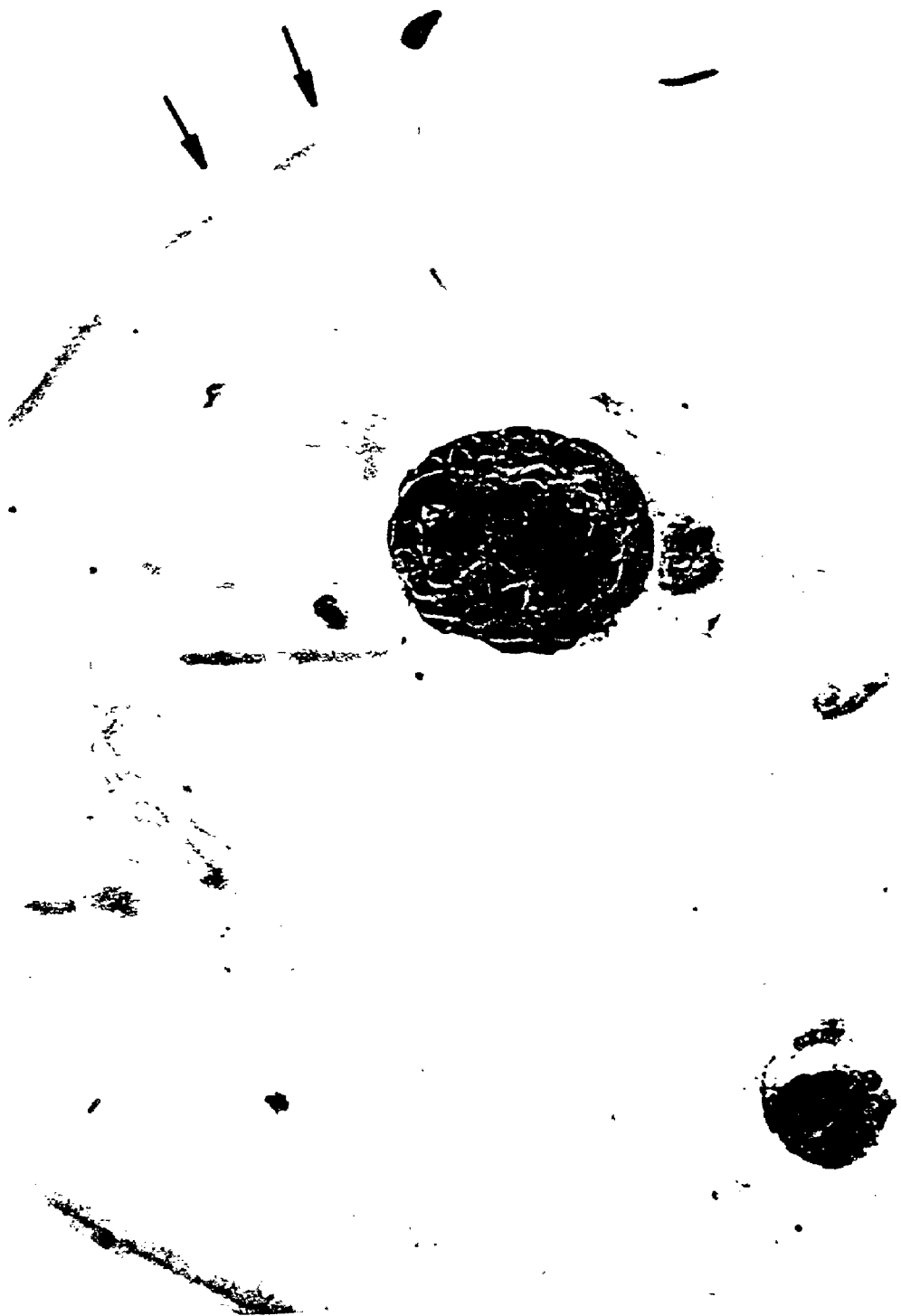
FIG. 13: Functioning, encapsulated rabbit islets, biopsied day #86, from peritoneum of NOD mouse, treated with CTLA4Ig. Note absence of NOD cell response and viable islets within capsule. H&E. (×400). Arrows point to outside of capsule wall.

Results:

Treatment of NODs with CTLA4Ig prolonged survival of intraperitoneal poly-l-lysine-alginate microencapsulated donor rabbit islet xenografts (CAP/I.P.) In spontaneously diabetic NODs, when compared to either islet microencapsulation or host CTLA4Ig treatment alone. The longest functioning grafts were in NODs treated for 92 days with CTLA4IgK, but mean graft survival was not statistically different from that of NODs which received CTLA4Ig for only 14 days (See Table 5). By contrast, recipient NOD treatment with cyclosporine A (CyA), monoclonal antibodies specific for CD8 (53.6.7.7) or CTL4Ig alone were ineffective (See Table 5). Biopsies of long-term surviving encapsulated rabbit islets from NODs documented intact microcapsules, viable donor islets, and absence of pericapsular NOD cellular response (See FIG. 13).

Biopsies of failed CTLA4Ig-treated, encapsulated rabbit islet xenografts showed primarily disrupted (broken) microcapsules, few viable islets, and minimal pericapsular cellular reaction. Biopsies of intrasplenic rabbit islets at rejection showed nuclear and cytoplasmic damage and nonviable islets. Biopsies of controls receiving intraperitoneal encapsulated rabbit islets, plus CyA or 53.6.7.7 recipient treatments or no treatment, performed at rejection on days 12–52 post-grafting, uniformly showed marked pericapsular accumulations of macrophages, neutrophils, and lymphocytes, as previously described (143, 3, 144).

Both NODS receiving encapsulated rabbit islets 10–14 days following passive transfer or $10^7$ splenocytes from a long-term normoglycemic NOD, (with functioning encapsulated rabbit islets, off CTLA4Ig treatment for 90 days) rejected their grafts in 10–12 days, with graft biopsies which were indistinguishable from untreated control NODs. Biopsies of pancreas from NODs in all experimental groups showed uniform absence of islets, and occasional accumulation of lymphocytes in perivascular areas.

TABLE 5

EFFECTS OF CTLA4Ig, CyA AND ANTI-CD8 MONOCLONAL ANTIBODY ON ENCAPSULATED RABBIT ISLET XENOGRAFT SURVIVAL IN DIABETIC NOD MICE

Figure 14:
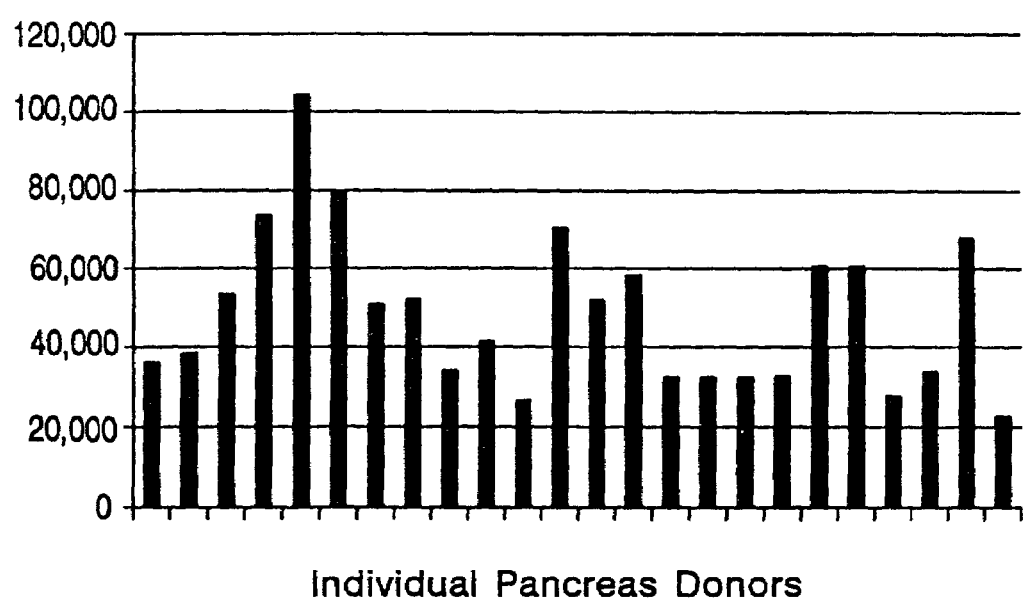
FIG. 14: Yield of Islets from Neonatal Porcine Pancreas (Total Islet #).
Figure 15:
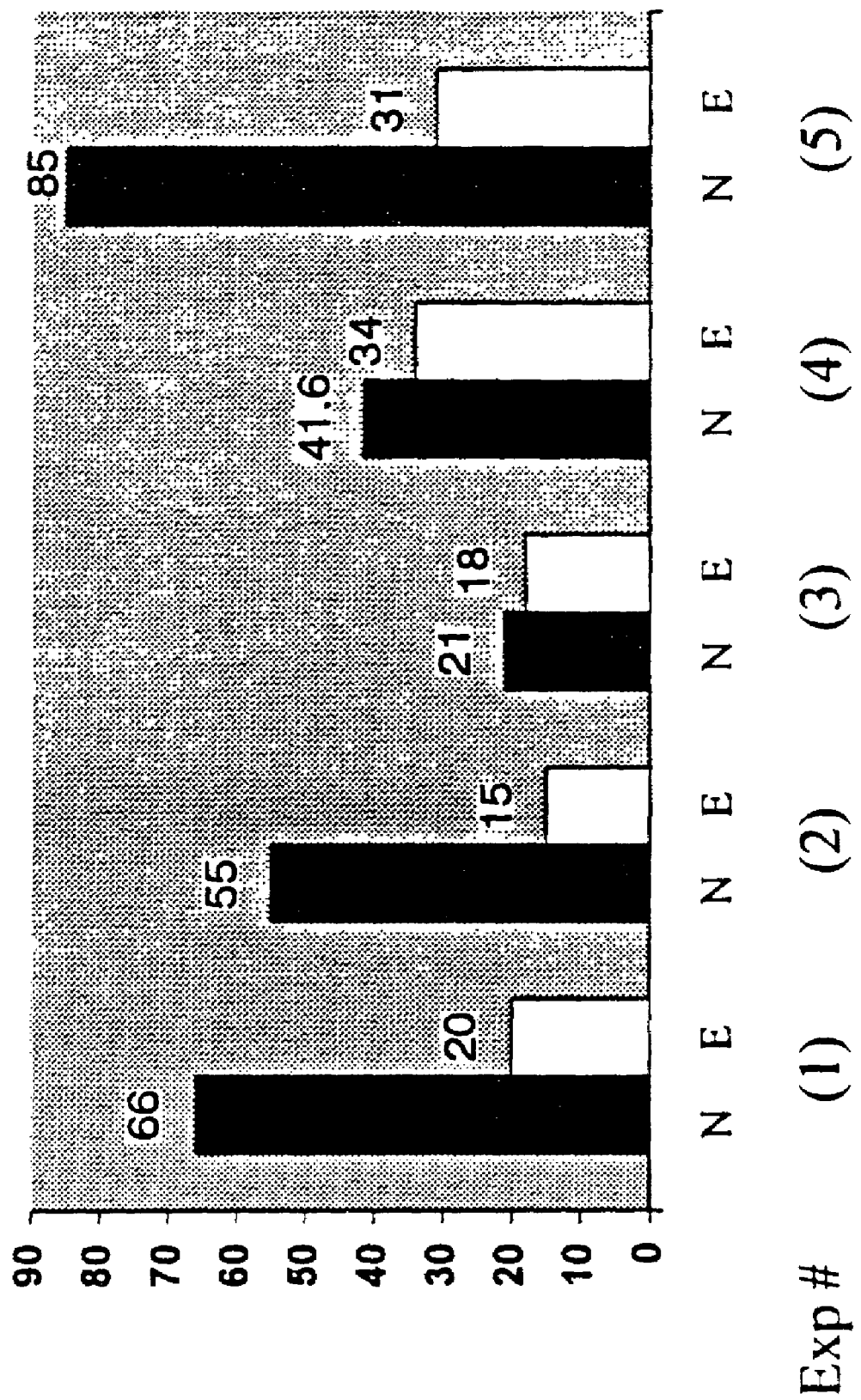
FIG. 15: In Vitro Insulin Release form Nonencapsulated (N) and Encapsulated (E) Neonatal Porcine Islets (uU/1000 islets/24 hr.)
Figure 16:
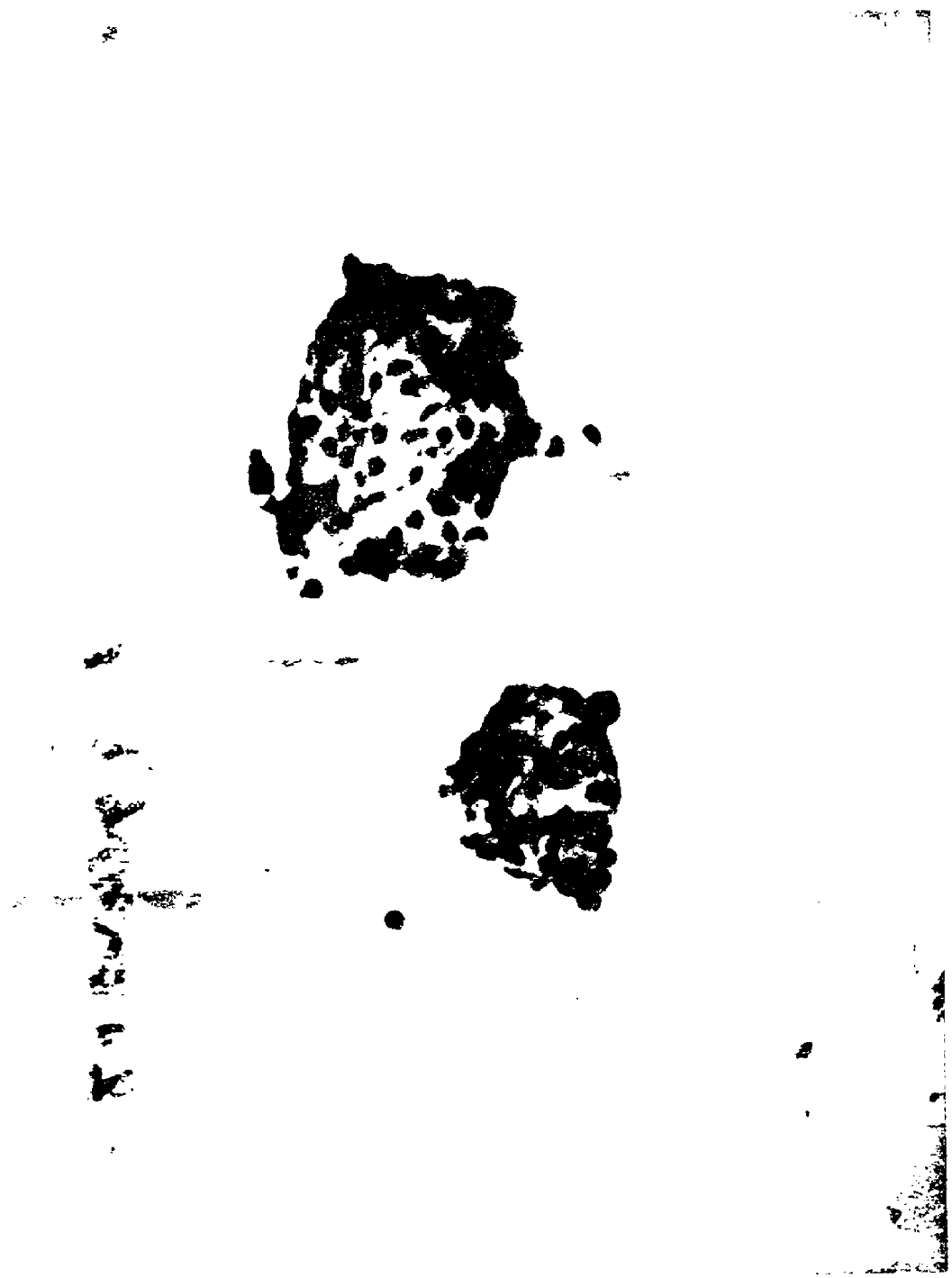
FIG. 16: Dispersed neonatal porcine "islets", in tissue culture, day #5. Anti-insulin immunocytochemistry demonstrates 5–10% beta cells. Approx. 400×.
Figure 17:
FIG. 17: Neonatal islet in microcapsule, biopsied day #103 from SZN-diabetic NOD-Scid mouse. anti-insulin immunohistochemistry, showing intensely insulin-positive beta cells, occupying approximately 80% of islet. Approx. 400×. Arrow points to outer surface of microcapsule membrane.

| Group | Donor-Recip | Technique | Rx. | (N) | X ± SE | Graft Survival Days |
|---|---|---|---|---|---|---|
| #1 | Rabbit-NOD | CAP/I.P. | None | 7 | 20 ± 2 | 12, 16, 18, 18, 20, 28, 28 |
| #2 | Rabbit-NOD | CAP/I.P. | CyA | 4 | 22 ± 3 | 13, 24, 26, 26 |
| #3 | Rabbit-NOD | CAP/I.P. | 53.6.7.7 7.7 | 4 | 5 ± 9 | 14, 15, 18, 52 |
| #4 | Rabbit-NOD | CAP/I.P. | CTLA4Ig (×92 days) | 8 | 108 ± 24 | 37[d], 43, 47, 58, 148, 151[s], 173, 205[d] |
| #5 | Rabbit-NOD | CAP/I.P. | CTLA4Ig (×14 days) | 4 | 70 ± 8**@ | 48, 66, 81, 83 |
| #6 | Rabbit-NOD | Renal/Splenic | CTLA4Ig | 3 | 6 ± 1* | 5[(s)], 6[(r)], 6[(a)] |
| #7 | Rabbit-NOD | Renal/Splenic | None | 2 | — | 5[(a)], 6[(r)] | s = sacrificed, functioning graft.
d = died, functioning graft.
*p < .005 vs. Group 1, ("t"-test).
**p < .0001 vs. Group 1, ("t"-test).
CTLA4Ig, 200 μg day −1, then Q.O.D., i.p.
CyA - 30 mg/kg day −1, then Q.D., s.c.
63.6.7.7 - 100 kg, day −5,+2, then weekly, i.p.
[(r)] = renal subcapsule, not encapsulated
[(s)] = splenic subcapsule
@ =P = .31 vs. Group #4, ANOVA Large-Scale Neonatal Porcine Islet Isolation We believe the neonatal pig is the most promising xenogeneic source of donor islets. A reproducible method for isolation of large numbers of functionally viable islets from neonatal procine donors has been developed (146, 147). With this technique, 30,000–100,000 islets may be obtained from each donor pig (FIG. 14). Neonatal pig islet cells continue to secrete insulin in vitro after microencapsulation. (FIG. 15). These neonatal pig islets are actually dispersed neonatal porcine pancreatic cells which reaggregate to form "islet"-like spheroids with approximately 5–10% beta cells (FIG. 16), which is significantly higher than the 1–2% beta cell concentration in the adult procine pancreas. Furthermore, biopsies of these "islets" 100 days following xenotransplantation reveal increased numbers of intensely insulin-positive islet cells (FIG. 17). These neonatal pig islets have an added advantage over adult islets, in that they appear to differentiate and proliferate within microcapsules after transplantation.

Both Encapsulated and Non-Encapsulated Neonatal Porcine Islets Reverse SZN-Diabetes in NOD-Scid Mice.

Recently, the Scid mutation has been back-crossed onto the NOD background, resulting in immuno-deficient NOD-Scid mice (66, 67, 68, 69). These mice are homozygous for the Scid mutation, which results in an inability to rearrange T-cell receptor and immunoglobulin genes (48, 79). Consequently, these mice lack T and B-lymphocytes. NOD-Scid mice do not develop diabetes spontaneously; but they may be rendered diabetic with multiple low-dose streptozotocin (MLD-SZN), (67, 68, 69) NOD-Scids express NOD MHC genes and other genes that are required for development of diabetes, upon transfer of lymphocytes from diabetic NODs.

Figure 18:
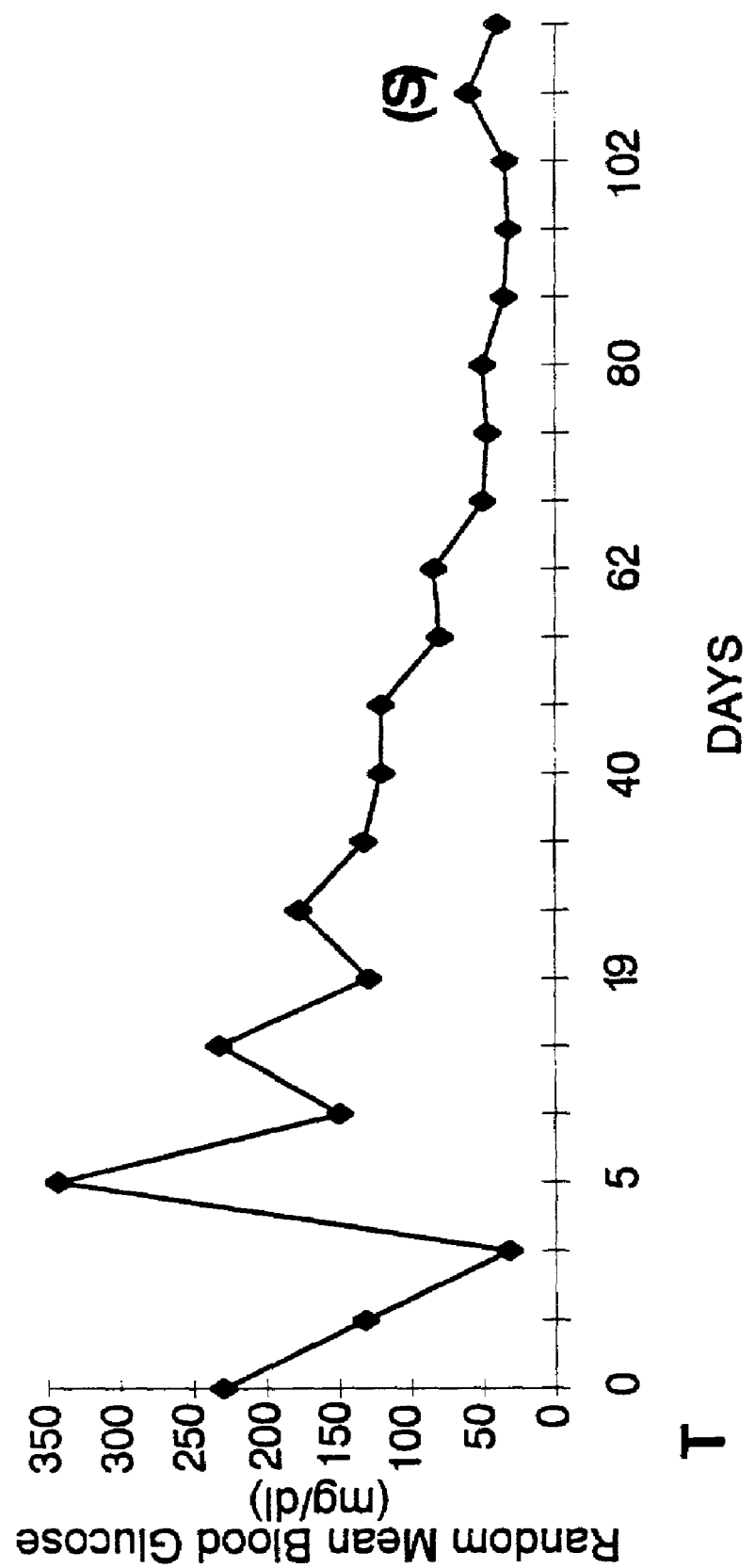
FIG. 18: Non-encapsulated intrasplenic/portal neonatal procine islet xenograft in streptozotocin diabetic NOD-Scid mouse. Biopsies (not shown) revealed viable porcine islets in both liver and splenic parenchyma.
 N=1
 T=Transplant
 S=Sacrificed for biopsies of spleen and liver
Figure 19:
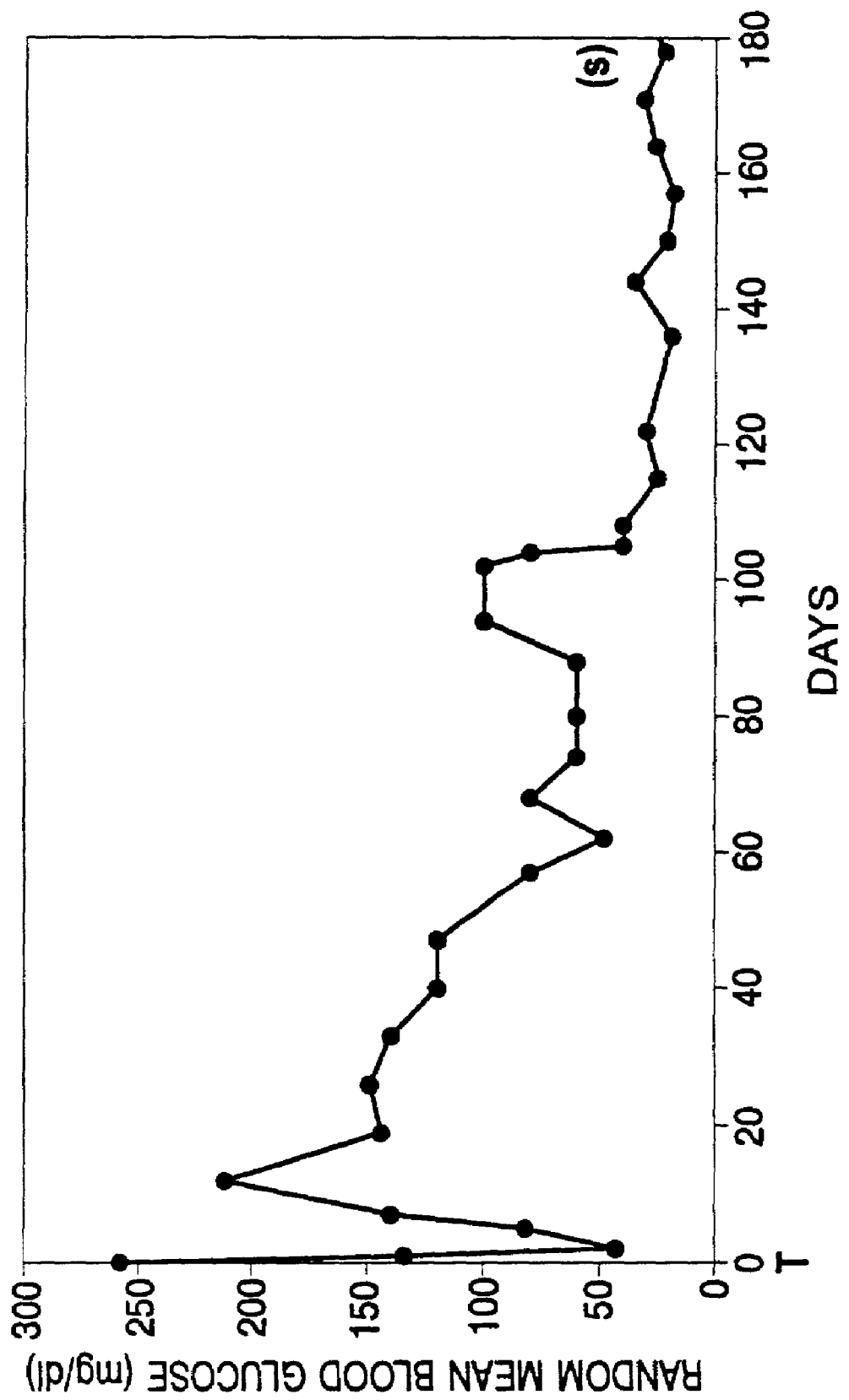
FIG. 19: Intraperitoneal microencapsulated neonatal porcine islet xenograft into streptozotocin-diabetic NOD-Scid mouse. Biopsied day #103 (see FIG. 20).
 N=1
 T=Transplant
 S=Sacrificed
Figure 20:
FIG. 20: Neonatal porcine islet in mirocapsule, biopsied day #103 after xenotransplantation to SZN-diabetic NOD-Scid mouse. H & E, ×400. Arrow points to inner surface of microcapsule membrane.

To document functional viability of neonatal procine islets, we xenografted them into SZN-diabetic normalized hyperglycemia in streptozotocin-diabetic NOD-Scid mice for >100 days (FIGS. 18, 19, 20). This data demonstrates that neonatal procine islets survive and function physiologically in xenogeneic recipients for prolonged periods, in the absence of an immunological attack.

Figure 21:
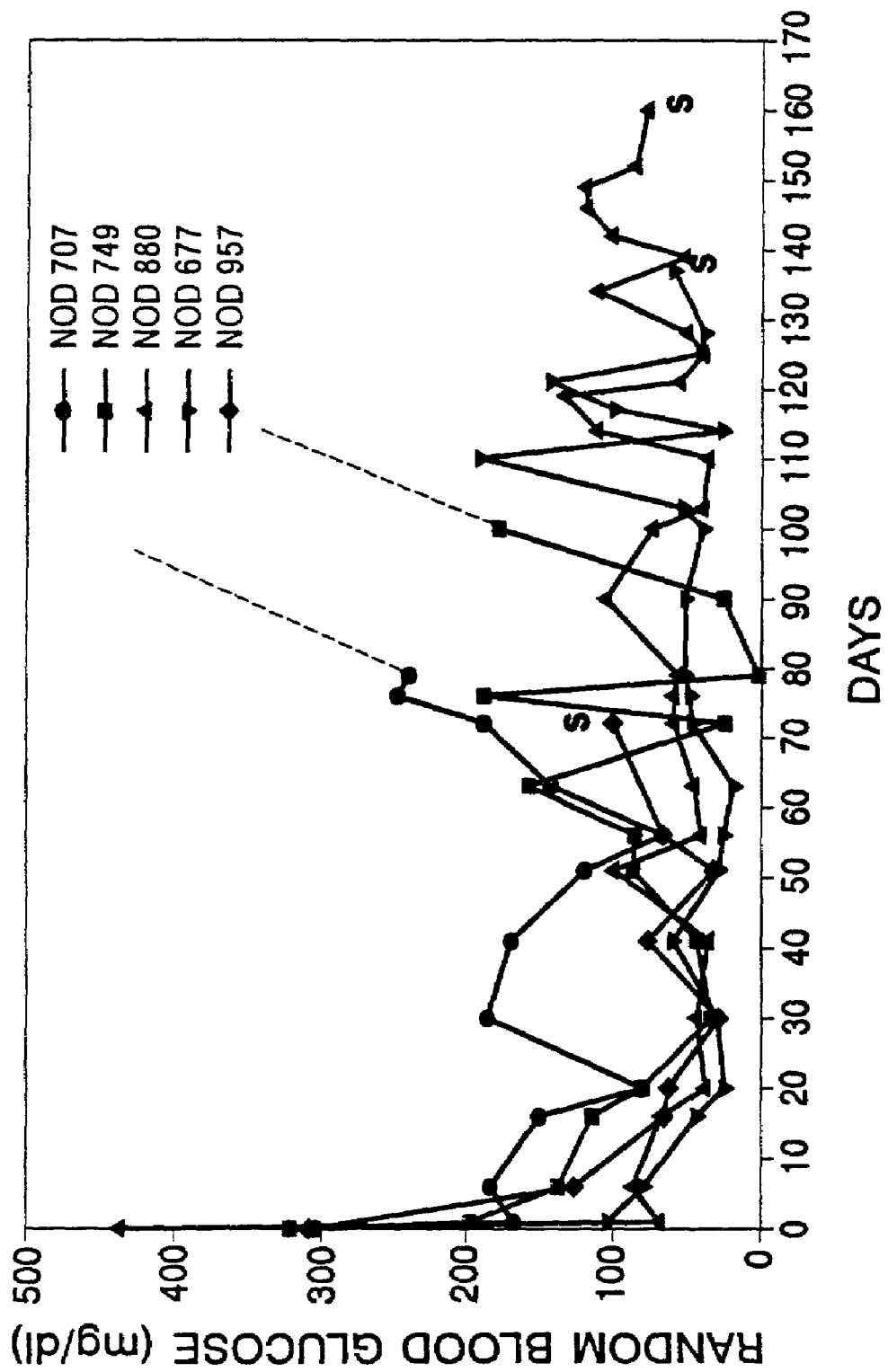
FIG. 21: Encapsuled Neonatal Porcine Islet Xenografts (N=5) in NODs, treated with CTLA4Ig, 200 µg i.p. Q.O.D., ×20 days. NOD 880 was biopsied at day #101 (see FIG. 22).
 S=Sacrificed for biopsy
 ( - - - )=Graft failure

We have found that CTLA4Ig significantly prolonged survival of encapsulated rabbit and porcine islets in NOD recipients, whereas CTLA4Ig alone did not protect non-encapsulated islet xenografts in NOD mice (Table 6 and FIG. 21).

TABLE 6

Survival of Microencapsulated (MC) Adult Rabbit and Neonatal Procine Islets in NOD Mice: Effects of NOD Treatment with CTLA4Ig

| Donor | Technique | Rx. | (N) | x ± S.E. | Graft Survival Days |
|---|---|---|---|---|---|
| Rabbit | MC/I.P. | None | 7 | 20 ± 2 | 12, 16, 18, 18, 20, 28, 28 |
| Rabbit | MC/I.P. | CTLA4-Ig[a] | 8 | 108 ± 24* | 37, 43, 47, 58, 148, 151, 173, 205 |
| Rabbit | MC/I.P. | CTLA4-Ig[b] CTLA4-Ig[a] | 4 | 70 ± 8 | 48, 66, 81, 83 |
| Rabbit | Splenic | None | 3 | 6 ± 1 | 5, 6, 6 |
| Rabbit | Splenic | None | 2 | — | 5, 6 |
| Neonatal Pig | MC/IP | CTLA4Ig[c] | 8 | 27 ± 13 | 9, 10, 11, 12, 12, 14, 23, 118[(s)] |
| Neonatal Pig | MC/IP | CTLA4Ig[c] | 5 | 111 ± 17 | 74[(s)], 80, 101[(s)], 137[(s)], 161[(s)] |
| Neonatal Pig | Splenic | None | 3 | 5 ± 1 | 4, 5, 5 |
| Neonatal Pig | Splenic |  | 3 | 6 | 5, 6, 7 |

Figure 22:
FIG. 22: Microencapsulated neonatal porcine islet, biopsied 101 days after xenotransplantation i.p. to spontaneously diabetic NOD mouse. CTLA4Ig, 200 µg i.p. Q.O.D., days # 0–21. Arrow points to inside of intact microcapsule wall. No pericapsular NOD cellular response. H. & E. ×200.
Figure 23:
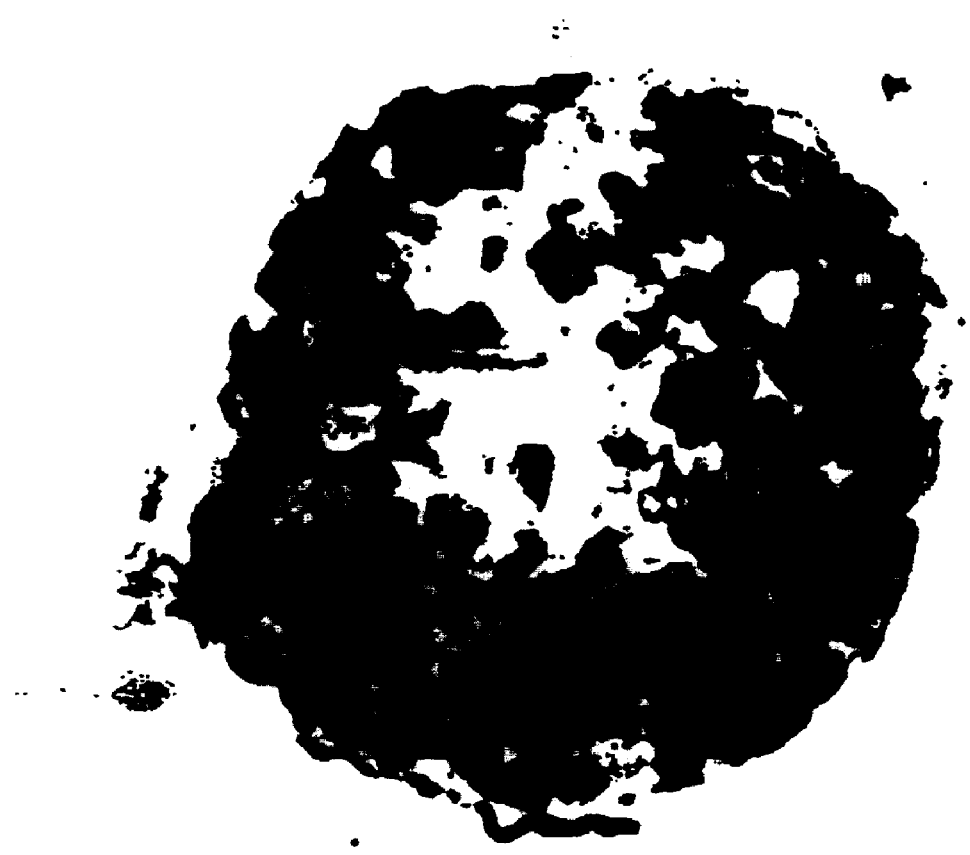
FIG. 23: Adjacent section of same biopsy Anti-insulin immunocytochemistry demonstrates that most cells are insulin-positive beta cells. ×400.
Figure 25A:
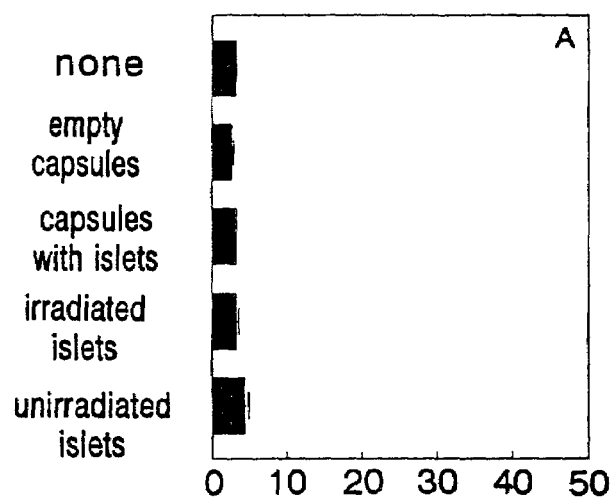
FIG. 25A-D: Spleen cells were cultured at 2×10$^6$ cells/ml in 96-well plates with no antigen, 10 empty capsules, 10 capsules containing neonatal pig islets, 4×10³ neonatal pig islets that were unirradiated or irradiated with 2000R. Spleen cells were obtained from normal NOD mice (panel A); diabetic NOD mice (panel B); diabetice NOD mice that were transplanted with encapsulated, neonatal pig islets and injected with CTLA4Ig (panel C) or mutant CTLA4Ig (panel D) as described in FIG. 24. After 48 hrs incubation, ³H-TdR was added and the cells harvested 18 hrs later. Results represent the average ±SD of triplicate cultures.
Figure 25B:
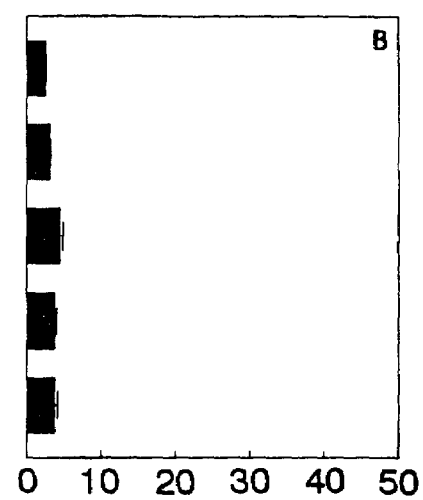
Figure 25C:
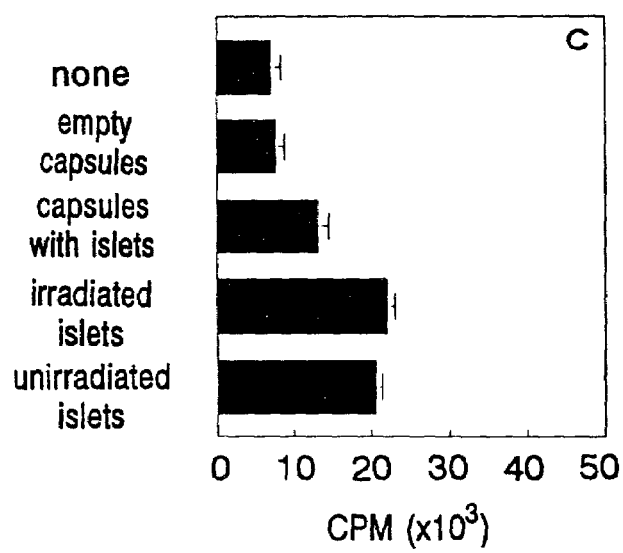
Figure 25D:
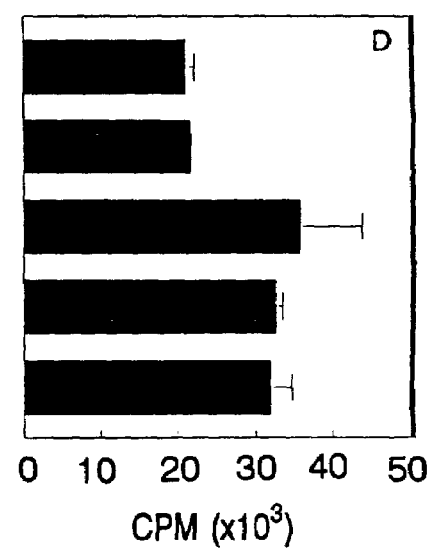

Ip = intraperitoneal
CTLA4Ig, 200 mcg I.P., QOD
* = p > .001 vs. MC alone
[(s)] = sacrifice for biopsy
[a] ×92 days
[b] ×14 days
[c] ×21 days Biopsies of long-term functioning encapsulated neonatal porcine islet xenografts showed viable porcine islets within intact microcapsules and absence of host NOD pericapsular reactivity was observed in biopsies of long-term normoglycemic NODs (FIGS. 22 and 23).

To analyze the potential mechanisms of action of CTLA4Ig in this model, we substituted a recently devised mutant of CTLA4Ig, which does not fix complement (CTLA4Ig*) (145). As shown in FIG. 24, our studies have revealed that CTLA4Ig* does not prolong graft survival above that of capsules alone. The data are distinct from findings with murine allografts, which are prolonged significantly by either conventional CTLA4Ig or mutant CTLA4Ig*. These results suggest that mechanisms of prolongation of graft survival by CTLA4Ig* may be different for allogeneic and xenogeneic islet grafts. The results suggest that the cytokine profile in a subject can be altered in favor of graft protection. In the sytem studied in this experiment, conventional CTLA4Ig altered the cytokine production so as to protect the graft by increasing gamma-interferon production in the host. Conversely, in the studied system, an increase in IL-10 production induced by CTLA4Ig* treatment favored graft rejection.

We also measured proliferative responses by spleen cells from a matched pair of diabetic NOD mice that were transplanted with the same batch of encapsulated, neonatal pig islets but were treated with either CTLA4Ig or the non-complement fixing CTLA4Ig* (FIG. 25). In this experiment, normal or diabetic NOD mice did not proliferate when stimulated by neonatal pig islets (panel A and B). The reason for the inconsistent response of nontransplanted NOD mice is not yet known but is under investigation. Empty capsules did not induce proliferation in any of the spleen cells but islets and encapsulated islets recognized by T-cells are small enough to exit from microcapsules. However, more experiments may verify this interpretation. As usual, background responses of spleen cells from mice rejecting grafts (panel D) were higher than those from mice that were not rejecting grafts (panel C).

These results suggest that spleen cells from both mice engrafted with encapsulated islets were primed in vivo, and are somewhat surprising given the fact that the mouse that received CTLA4Ig showed no signs of rejection. These results did not address the possibility that there might be different fluids from cultures stimulated with neonatal pig islets for lymphokines by ELISA (FIG. 26). These results indicate that lymphokines were produced only by mice that were engrafted with neonatal, pig islets. More importantly, spleen cells from the mouse that had accepted its graft long term (treated with CTLA4Ig) produced a preponderance of INFγ and low levels of IL-10. These results suggest that CTLA4Ig induced long term tolerance to neonatal pig islets that is associated with T cells that produce INFγ. Rejection of xenogeneic islet graft occurred when lymphokines shifted to IL-10. Thus, graft rejection is associated with a Th2-like response, whereas graft survival is associated with Th1-like responses. These findings are consistent with our working model (FIG. 27). These results differ somewhat from the picture obtained by analyzing mRNA level at the site of rejection where IL-4 predominated in mice that rejected the encapsulated, xenogeneic islets.

Discussion:

On the basis of our data, we develop a model to describe the mechanisms that we think are involved in rejection of microencapsulated xenogeneic islets by autoimmune, NOD mice (FIG. 27). Secreted insulin clearly crosses the membrane of double walled microcapsules and regulates glucose levels in engrafted mice. Potentially, other donor proteins or protein fragments of less than 100,000 mw (AgX) that are shed or secreted by islets diffuse out of the microcapsule and are endocytosed by dendritic cells. Dendritic cells process proteins via the MHC class II pathway and present peptide X complexed with class II and co-stimulatory molecules to CD4+T cells. In the presence of the appropriate cytokines, CD4$^+$ T cells are activated and develop into Th2 cells that express CD40L. B cells with surface IgM that binds AgX endocytose and process it into peptides that bind MHC class II which are expressed on the surface of B cells. Th2 specific peptide X complexed with class II binds B cells and the interaction of CD40 with CD40L causes the activation of B cells. Activated B cells mature into plasma cells under the direction of Th2 lymphokines. Plasma cells secrete specific antibody that forms complexes with AgX.

Antibodies are not able to directly damage the encapsulated islets because they are too large to enter the capsules. However, antibodies could be involved in the recruitment and activation of macrophages which are the predominant population in the peritoneal cavity of NODs rejecting encapsulated islet xenografts. Specific antibodies in the peritoneal cavity could form complexes with antigens shed or secreted from the capsules. Such antigen-antibody complexes efficiently bind to FcR expressed on the surface of peritoneal macrophages. Binding of complexes to FcR activates macrophages to secrete a variety of mediators including IL-1, TNFα and nitric oxide (NO) (122, 123), all of which have toxic effects on islets and all of which are small enough to cross a double walled microcapsule. The effector arm could be further augmented by the activation of complement (c) by antigen complexes. C3b bound to the complexes enhances the activation of macrophages by increasing the binding of the complexes via the C3b receptor (124) and small peptides such as C3b released during complement activation induce local inflammatory responses thereby attracting more macrophages into the peritoneal cavity (125).

We demonstrated synergy of donor islet microencapsulation and NOD CTLA4Ig treatment in prolonging islet xenograft survival. Our data represent the longest biopsy-proven survival of discordant islet xenografts in NODs reported to date. Neither CTLA4Ig nor encapsulation alone were effective. Furthermore, splenocytes from a long-term successful graft recipient did not transfer donor-specific unresponsiveness. Failure of anti-CD8 and CyA therapies is consistent with our hypothesis of a primarily Th2 type response in this model.

There is considerable evidence that xeno-recognition (unlike allorecognition) occurs primarily via the so-called "indirect" antigen presentation pathway, by which host APC present peptides scavenged from extracellular (donor) proteins to host helper T-cells (27, 137, 29, 138). Our recent report, that the host MHC is critical to NOD rejection of encapsulated islet xenografts (75), and our prior observations, that helper T-cells are essential for this response (7), both are consistent with an "indirect" pathway. Our prior findings of more rapid destruction of encapsulated "discordant" (widely unrelated) islets (canine, rabbit, bovine, porcine) than "concordant" (closely related) (rat) islets (20), also support this hypothesis, since the "direct" pathway would favor an accelerated reaction to "concordant" donor tissue. Furthermore, our current data suggest that "indirect" antigen presentation may be blocked by CTLA4Ig in this model of encapsulated islet xenotransplantation. In conclusion, we have found that neither microencapsulation nor CTLA4Ig alone prevent NOD destruction of rabbit islets. However, we have observed synergy between CTLA4Ig treatment of NOD recipients plus encapsulation with significantly prolonged discordant islet xenograft survival.

REFERENCES

1. The Diabetes Control and Complications Trials Research Group. The effect of intensive treatment of diabetes on the development and progressions of long-term complications in insulin-dependent diabetes mellitus. NEJM 1993; 329:977–986.
2. Lacy P. Status of islet cell transplantation. Diabetes Review 1993; 1:76–92.
3. Parker C. Naji A. Perspectives and islet transplantation for diabetes-cures or curiosities? NEJM 1992; 327:1861–1868.
4. Warnock G., Rajotte R. Human pancreatic islet transplantation. Transplantation Reviews 1992; 6:195–208.
5. Remuzzi F., Ruggenenti P., Mauer S. Pancreas and kidney/pancreas transplants; experimental medicine or real improvement? Lancet 1994; 343:27–31.
6. Weber C., Hardy M., Riveria S., Bailey-Braxton D., Michler R., Thomas W., Chabot J., Pi-Sunyer F., Wood M., Reemtsma K. Diabetic mouse bioassay for functional and immunologic human and primate islet xenograft survival. Transplant proceedings 1986; 18:823–828.
7. Weber C., Zabinski S., Koschintzky T., Rajotte R., Wicker L., D'Agati V., Peterson L., Norton J., Reemtsma K. The role of CD4$^+$ helper T cells in destruction of microencapsulated islet xenografts in NOD mice. Transplantation 1990; 49:396–404.
8. Mandel T., Koulmanda M., Loudovaris R., Bacelj A. Islet grafts in NOD mice: A comparison of iso-, allo-, and pig xenografts. Transplant Proceedings 1989; 21:3813–3814.
9. Weber C., D'Agati V., Ward L., Costanzo M., Rajotte R., Reemtsma K. Humoral reaction to microencapsulated rat, canine, porcine islet xenografts in spontaneously diabetic NOD mice. Transplantation Proceedings 1993; 25:462–463.
10. Akita K., Ogawa M., Mandel T. Effect of FK506 and anti-CD4 therapy on fetal pig pancreas xenografts and host lymphoid cells in NOD/Lt, CBA, and BALB/c mice. Cell Transplantation 1994; 3:61–73.
11. Morris C., Fung M., Simeonovic S., Wilson D., Hapel A. Cyokine expression in CDA.H mice following xenotransplantation of fetal pig proislets. Transplantation Proceedings 1994; 26:1304–1305.
12. Lenschow D., Zeng Y., Thistlewaite J., Montag A., Brady W., Gibon M., Linsley P., Bluestone J. Long-term survival of xenogeneic pancreatic islet grafts induced by CTLAIg. Science 1992; 257:789–795.
13. Falqui L., Finke E., Carel J., Scharp D., Lacy P. Marked prolongation of human islet xenograft survival (human-to-mouse) by low temperature culture and temporary immunosuppression with human and mouse antilymphocyte sera. Transplantation 1991; 51:1322–1325.
14. Ricordi C., Scharp D., Lacy P. Reversal of diabetes in nude mice after transplantation of fresh and seven day cultured (24° C.) human pancreatic islets. Transplantation 1988; 45:994–996.
15. Ricordi C., Kneteman N., Scharp D., Lacy P. Transplantation of cryopreserved human pancreatic islets into diabetic nude mice. World J Surgery 1988; 12:861–865.
16. Ricordi C., Lacy P., Sterbenz K., Davie J. Low-temperature culture of human islets or in vivo treatment with L3T4 antibody produces a marked prolongation is islet (human-to mouse). Transplantation 1987; 44:465–468.
17. Ricordi C., Lacy P., Sterbenz K., Davie M. Low-temperature culture of human islets plus in vivo treatment of L3T4 antibody produces a marked prongation of islet human-to-mouse xenograft survival. Proc Natl Acad Sci 1987; 84:8080–8084.
18. Ricordi C., Finke E., Lacy P. A method for the mass isolation of islets from the adult pig pancreas. Diabetes 1986; 35:649.
19. Weber C., Costanzo M., Zabinski S., Krekun S., Koschitzky T., D'Agati V., Wicker L., Rajotte R., Reemtsma K. Xenografts of microencapsulated rat, canine, porcine, and human islets into streptozotocin (SZN)-and spontaneously diabetic NOD mice. In: Ricordi C. (Eds.) *Pancreatic Islet Transplantation*, R. G. Landes, Austin, 1992: 177–190.
20. Weber C., Reemtsma K. Microcapsulation in small animals-II: Xenografts. In: Lanza R., Chick W. (Eds.). *PANCREATIC ISLET TRANSPLANTATION SERIES; VOL III: IMMUNOISOLATION OF PANCREATIC ISLETS*. R. Landes, Austin, 1994:59–79.
21. Zhou D., Sun Y., Vacek I., Ma P., Sun A. Normalization of diabetes in cynomolgus monkeys by xenotransplantation of microencapsulated porcine islets. Transp Proc 1994; 26:1091–1092.
22. Giannarelli R., Marchetti P., Villani G., DiCarlo A., Cosimi S., Andreozzi M., Cruschelli L., Masieco P., Coppelli A., Navalesi R. Preparation of pure, viable porcine and bovine islets by a simple method. Transplantation Proceedings 1994; 26:630–631.
23. Jos C., Connolly J., Deardon D., Pearson R., Parrot N., Johnson R. A simple method for isolation from the rabbit pancreas. Transplantation 1994; 58:390–392.
24. Reemtsma K., Weber C., Kazin M., Pi-Sunyer F., Nilaver G., Fenoglio C. Xenogeneic islets of Langerhans for human transplantation: Functional and morphologic studies of primate, bovine and rabbit islets. In: Friedman E., L'Esperance L. (Eds). *Diabetic-Renal-Retinal Syndrome Vol.* 3, Grune and Stratton, New York, 1986:521–546.
25. Forty J., Cary N., White D., Wallwork J. Hyperacure rejection of rabbit hearts by human blood is mediated by the alternative pathway of complement. Transplantation Proceedings 1992; 124:488–489.
26. Platt J., Back F. The barrier to xenotransplantation. Transplantation 1991; 52:937–947.
27. Auchincloss H. Xenogeneic transplantation. Transplantation 1988; 46:1–20
28. Lanza R. P., Beyer A. M., Chick W. L. Xenogeneic humoral responses to islets transplanted in biohybrid diffusion chambers. Transplantation 1994; 57:1371–1375.
29. Faustman F., Coe C. Prevention of xenograft rejection by masking donor HLA class I antigens. Science 1991; 252:1700–1702.
30. Colton C., Avgoustiniatos E. Bioengineering in development of the hybrid artificial pancreas. J. Biochem Enf. 1991; 113:152–170.
31. Lanza R., Sullivan S., Chick W. Islet transplantation with immunoisolation. Diabetes 1992; 41:1503–1510.
32. Scharp D., Swanson C., Olack B., Latta P., Hegre O., Doherty E., Gentile F., Flavin K., Ansara M., Lacy P. Protection of encapsulated human islets implanted without immunosuppression in patients with Type I or Type II diabetes and in nondiabetic control subjects. Diabetes 1994; 43:1167–1170.
33. Ricker A., Stockberger S., Halban P., Eisenbarth F., Bonner-Weir S. Hyperimmune response to microencapsulated xenogeneic tissue in non obese diabetic mice. In:

Jaworski M. (Eds). *The Immunology of Diabetes Mellitus*. Elseview, Amsterdam, 1986:193–200.

34. Weber C., Zabinski S., Norton J., Koschitzky T., D'Agati V., Reemtsma K. The future role of microencapsulation in xenotransplantation. In: Hardy M. (Eds). *Xenograft* 25, Elseview, Amsterdam, 1989:297–308.

35. Halle J., Bourassa S., Leblond F., Chevalier S., Beaudry M., Chapdelaine A., Cousineau S., Saintonge J., Yale J. Protection of islets of langerhans from antibodies by microencapsulation with alginate-poly-l-lysine membranes. Transplantation 1993; 44:350–354.

36. Horcher A., Zekorn T., Siebers U., Klock G., Frank H., Houben R., Bretzel R. G., Zimmerman U., Federlin K. Transplantation of microencapsulated islets in rates: Evidence for induction of fibrotic overgrowth by islets alloantigens released from microcapsules. Transpl Proc 1994; 26:784–786.

37. Sibers R., Zekorn T., Horcher A., Klock G., Houben R., Frank H., Bretzel R. G., Zimmerman U., Federlin K. Microencapsulated transplantation of allogeneic islets into specifically presensitized recipients. Transpl Proc 1994; 26:787–788.

38. Lanza R., Kuhtreiber W., Ecker D., Staruk J., Chich W., Xenotransplantation of porcine and bovine islets without immunosuppression using uncreated alginate microspheres. Transplantation 1995; 59:1377–1384.

39. Lanza R., Ecker D., Kuhtrieber W., Staruk J., Marsh J., Chick W. A simple method for transplanting discordant islets into rats using alginate gel spheres. Transplantation 1995; 59:1485–1487.

40. Soon-Shiong P., Feldman E., Nelson R., Komtebedde J., Smidsrod O., Skauk-Braek G., Espevik T., Heintz R., Lee M. Successful reversal of spontaneous diabetes in dogs by using intraperitoneal microencapsulated islets. Transplantation 1992; 54:769–774.

41. Soon-Shiong P., Heintz R. E., Merideth N., Yao Q. X., Yao Z., Zheng T., Murphy M., Moloney M. K., Schmehl M., Harris M., Mendez R., Sandford P. A. Insulin independence in a type I diabetic patient after encapsulated islet transplantation. Lancet 1994; 343:950–951.

42. Heald K., Jay T., Downing R. Assessment of the reproducibility of alginate encapsulation of pancreatic islets using the MTT calorimetric assay. Cell transplantation 1994; 3:333–337.

43. Jarpe A., Hickman M., Anderson J. Flow cytometric enumeration of mononuclear cell populations infiltrating the islets of Langerhans in prediabetic NOD mice: Development of model of autoimmune insulitis for Type I diabetes. Regional Immunology 1990; 3:305–317.

44. Miller B., Appal M., O'Neil J., Wicker L. Both the Lyt-2+ and L3T4+T call subsets are required for the transfer of diabetes in nonobese diabetic mice. J. Immunol 1988; 140:52–58.

45. Haskins K., Portas M., Bradley B. T-lymphocyte clone specific for pancreatic islet antigen. Diabetes 1988; 37:1444–1448.

46. Jansen A., Homo-Delarche F., Hooijkaas J., Leenen P., Dardenne M., Drexhage H. Immunohistochemical characterization of monocytes-macrophages and dendritic cells involved in the initiation of the insulitis and B-cell destruction in NOD mice. Diabetes 1994; 43:667–674.

47. Prins J., Todd J., Rodrigues N., Ghosh S., Hogarth M., Wicker L. Gaffney E., Fishcer P., Sirotina A., Peterson L. Linkage on Chromosome 3 of autoimmune diabetes and defective Fc receptor for IgG in NOD mice. Science 1993; 260:695–695.

48. Lipes M., Rosenzweig A., Tan K., Tanigawa G., Lass D., Seidman J., Eisenbarth G. Progression to diabetes in nonobese diabetic (NOD) mice with transgenic T cell response. Science 1993; 259:1165–1169.

49. Gelber C., Pabrosky L., Singer S., McAteer D., Tisch R., Jolicoeur C., Buelow R., McDevitt H., Fathman G. Isolation of nonobese diabetic mouse T-cells that recognize novel autoantigens involved in the early events of diabetes. Diabetes 1994; 43:33–39.

50. Podolin P., Pressey A., DeLarato N., Fischer P., Peterson L., Wicker L. I-E+ nonobese diabetic mice develop insulitis and diabetes. J Exp Med 1993; 178:793–803.

51. Haskins K., Portas M., Bergman B., Lafferty K., Bradley B. Pancreatic islet-specific T-cell clones from nonobese diabetic mice. PNAS 1989; 86:8000–8004.

52. Haskins K., McDuffie M. Acceleration of diabetes in young NOD mice with a $CD4^+$ islet-specific T cell clone. Science 1990; 249:1433–1436.

53. Supon P., Stecha P., Haskins K. Anti-islet cell antibodies from NOD mice. Diabetes 1990; 39:1366–1392.

54. Bergman B., Haskins K. Islet-specific T-cell clones from the NOD mouse respond to B-granule antigen. Diabetes 1994; 43:197–203.

55. Peterson J., Pike B., McDuffie M., Haskins K. Islet-specific T-cell clones transfer diabetes to nonobese diabetic (NOD) $F_1$ mice. J. Imminol 1994; 153:2800–2806.

56. Kaufman D., Clare-Salzier M., Tian J. Spontaneous loss of T-cell tolerance to flutamic acid decarboxylase in murine insulin-dependent diabetes. Nature 1993; 365:69–72.

57. Tisch R., Yang X., Singer S., Liblau R., Fugger L., McDevitt H. Immune response to glutamic acid decarboxylase correlates with insulitis in non-obese diabetic mice. Nature 1993; 366:72–75.

58. Dylan D., Gill R., Schloot N., Wegmann D. Epitope specificity, cytokine production profile and diabetogenic activity so insulin-specific T cell clones isolated from H=NOD mice. Eur J. Immunology 1995; 25:1062.

59. Wang Y., Hao L., Gill R., Lafferty K. Autoimmune diabetes in NOD mouse is L3T4 T-lymphocyte dependent. Diabetes 1987; 36:535–538.

60. Boitard D., Bendelac A., Richard M., Carnaud C., Bach J. Prevention of diabetes in nonobese diabetic mice by anti-l-A monoclonal antibodies: Transfer of protection by splenic T cells. PNAS 1988; 85:9719–9723.

61. Serrese D., Gaskins H., Leiter E. Defects in the differentiation and function of antigen presenting cells in NOD/lt. Mice. J Imunol 1993; 150:2534–2543.

62. Rabinovitch A., Sumoski W., Rajotte R., Warnock G. Cytotoxic effects of cytokines on human pancreatic islet cells in monolayer culture. J. Of Clinical Endocrinology and Metabolism 1990; 71:152–156.

63. Bergmann L., Kroncke K., Suschek D., Kolb H., Kolb-Bachofen C. Cytotoxic action of IL-LB against pancreatic islets in mediated via nitric oxide formation and is inhibited by $N^G$-monomethyl-L-arginine. FEBS letter 1992; 299:103–106.

64. Xenos D., Stevens R., Gores P., Casanova D., Farney A., Sutherland D., Platt J. IL-1 induced inhibition of B-cell function is mediated through nitric oxide. Transpl Proc 1993; 25:994–994.

65. Anderson H., Jorgensen K., Egeberg J. Mandrup-Poulsen R., Berup J. Nicotinamide prevents Interleukin-I effects on accumulated insulin release and nitric oxide production in rat islets of Langerhans. Diabetes 1994; 43:770–777.

66. Christianson S., Shultz L., Leiter D. Adoptive transfer of diabetes into immunodeficient NOD-Scid/Scid mice. Diabetes 1993; 42:44–45.
67. Gerling I., Friedman H., Greiner D., Schultz L., Leither E. Multiple low-dose streptozotocin-induced diabetes in NOD-Scid/Scid mice in the absence of functional lymphocytes. Diabetes 1994; 43:433–440.
68. Rohane P., Shimada A., Ki m D., Edwards C., Charlton B., Shultz L., Fathman C. Islet infiltrating lymphocytes from prediabetic NOD mice rapidly transfer diabetes to NOD-scid/scid mice. Diabetes 1995; 44:550–554.
69. Shultz L., Schweitzer P., Christian S., Gott B., Schweitzer I., Tennent B., McKenna S., Mobraaten L., Rajan R., Greiner D., Leiter E. Multiple defects in innate and adaptive immunologic function in NOD/LtSz-scid mice. J of Immunology 1995; 154:180–191.
70. Weber C., Krekun S., Loschitzky S., Zabinski S., D'Agati C., Hardy M., Reemtsma K. Prolonged functional survival of rat-to-NOD mouse islet xenografts by ultraviolet-B (UV-B) irradiation plus microencapsulation of donor islets. Transplantation Proceedings 1991; 23:764–766.
71. Lafferty K. Circumventing rejection of islet grafts; An overview. In: Van Schifgaarde R., Hardy M. (Eds). Elsevier, Amsterdam, 1988:279–291.
72. Ricker A., Bhatia V., Bonner-Weir S., Eisenbarth G. Microencapsulated xenogeneic islet grafts in NOD mouse: Dexamethasone and inflammatory response. Diabetologia 1989; 32:53.
73. Lafferty K. J., Hao L. Approaches to the prevention of immune destruction of transplanted pancreatic islets. Transpl Proc 1994; 26:399–400.
74. Weber C., Price J., Costanzo M., Becker A., Stall A. NOD mouse peritoneal cellular response to poly-l-lysine-alginate microencapsulated rat islets. Transplantation Proceedings 1994; 26:1116–1119.
75. Weber C., Tanna A., Costanzo M., Price J., Peterson L., Wicker L. Effects of host genetic background on survival or rat->mouse islet xenografts. Transplantation Proceedings 1994; 26:1186–1188.
76. Wijsman J., Atkinson P., Mazheri R. Histological and immunopathological analysis of recovered encapsulated allogeneic islets from transplanted diabetic BB/W rates. Transplantation 1992; 54:588–592.
77. Cole D., Waterfall M., McIntyre M., Baird J. Microencapsulated islet grafts in the BB.E rat a possible role for cytokines in graft failure. Diabetologia 1992; 35:231–237.
78. Mazaheri R., Atkinson P., Stiller C., Dupre J., Vose J., O; Shea F. Transplantation of encapsulated allogeneic islets into diabetic BB/W rates: Effects of immunosuppression. Transplantation 1991; 51:750–754.
79. Darquy S., Reach G. Immunoisolation of pancreatic B cells by microencapsulation. Diabetolgia 18=985; 28:776–780-.
80. Baldwin W., Pruitt S., Brauer R., Daha M., Sanfillippo F. Complement in organ transplantation. Transplantation 1995; 59:797–808.
81. Iwata H., Takagi R., Amemiya H. Marked prolongation of islet xenograft survival (hampster-to-mouse) by microencapsulation and administration of 15-deoxyspergualin. Transplantation Proceedings 1992; 24:1516–1518.
82. Pierson R., Winn H., Russell P., Auchincloss H. CD-4 positive lymphocytes play a dominant role in murine xenogeneic responses. Transplantation Proceedings 1989; 21:519–521.
83. Gill R., Wolf L., Daniel D., Coulombe M. CD4+ T cells are both necessary and sufficient for islet xenograft rejections. Transp Proc 1994; 26:1203–1204.
84. Weber C., Zabinski S., Koschitzky T., Wicker L., Rajotte R., Peterson L., D'Agati V., Reemtsma K. Microencapsulated dog and rat islet xenografts into streptozotocin-diabetic and NOD mice. Hoem Metab Res 1990; 35:219–226.
85. Cirulli V., Halban P., Rouiller D. Tumor necrosis factor a modifices adhesion properties of rat islet B cells. J Clim Invest 1993; 92:1868–1876.
86. Campbell I., Iscara A., Harrison L. Interferon gamma and tumor necrosis factor alpha: cytotoxicity to murine islets of Langethans. J Immunol 1988; 141:1325–1329.
87. Rabionovitch A. Immunoregulatory and cytokine imbalances in the pathogenesis of IDDM. Diabetes 1994; 43:613–621.
88. Ablamunits V., Baranove F., Mandrup-Poulsen R., Nerup J. In vitro inhibition of insulin release by blood mononuclear cells from insulin-dependent diabetic and healthy subjects: synergistic action of IL-1 and TNF. Cell Transplantation 1994; 3:55–60.
89. Mandrup-Poulsen T., Bendtzen D., Dinarello C., Nerup J. Human tumor necrosis factor potentiates interleukin-mediated rate of pancreatic B-cell cytotoxicity. J Immunol 1987; 139:4077–4082.
90. Thai N., Wang S., Valdivia L., Celli S., Reilly M. Demetris A., Simmons R., Stazi T., Fung J. Cytokine messenger RNA profiles in hamster-to-rat liver xenografts. Transplantation Proceedings 1993; 25:444–445.
91. O'Connell P., Pacheoco-Silca A., Nickerson P., Muggia R., Bastos M., Kelly V., Strom R. Unmodified pancreatic islet allograft rejection results in preferential expression of certain T cell activation transcripts. J Immunol 1993; 150:1093–1104.
92. Nickerson P., Pacheco-Silca A., O'Connell P., Steurer W., Kelly V., Strom R. Analysis of cytokine transcripts in pancreatic islet cell allografts during rejection and tolerance induction. Transplantation Proceedings 1993; 25:984–985.
93. Lowry R., Takeuchi T. The Th1, Th2 paradigm and transplantation tolerance R. Landes, Austin. 1994; In press.
94. Lederer J., Liou J., Todd M., Glicher L., Lichtman A. Regulation of cytokine gene expression in T helper cell subsets. J Immunol 1994; 1:78–86.
95. Janeway C., Bottomly K. Signals and signs for lymphocyte responses. Cell 1994; 76:275–285.
96. Aguilar-Diosdada M., Parkinson D., Corbett J., Kwon G., Marshall C., Gingerich R., Santiafo J., McDaniel M. Potential autoantigens in IDDM: expression of carboxypeptidase-H and insulin but not glutamate decarboxylase on the B-cell surface. Diabetes 1994; 43:418–425.
97. Jenkins M. The ups and downs of T cell costimulation. Immunity 1994; ':443–446.
98. Liu Y., Jones B., Brady W., Janeway C., Linsley P. Co-stimulation of murine CD4 T cell growth: cooperation between B7 and heat-stable antigen. Eur J Immunol 1992; 22:2855–2859.
99. Harding F. McArthur J., Fross J., Raulet D., Alliston J. CD28-mediated signaling co-stimulates murine T cells and prevents induction of anergy in T-cell clones. Nature 1992; 356:607–609.
100. Galvin F., Greeman G., Razi-Wolf Z., Hall W., Benacerraf B., Nadler L., Reiser H. Murine B7 antigen provides a sufficient costimulatory signal for antigen-specific and MHC-restricted T cell activation. J Immunol 1992; 149:3802–3808.
101. Hathcock K., Laszio G., Dickler H., Bradshaw J., Linsley P., Hodes R. Identification of an alternative CTLA-4 ligand costimulatory for T cell activation. Science 1993; 262:905–907.
102. Perrin P., Scott D., Quigley L., Albert P., Feder O., Gray G., Abe R., June C., Racke M. Role of B7: CD28/CTLA-4 in the induction of chronic relapsing experimental allergic encephalomyelitis. J of Immunology 1995; 154:1481–1490.
103. Gimmi C., Freeman G., Gribben J., Gray G., Nadler L. Human T-cell anergy is induced by antigen presentation in the absence of B7 costimulation. Immunology 1993; 90:6586–6590.
104. Guerder S., Meyerhoff J., Flavell R., The role of the T-cell costimulatory B7-1 in autoimmunity and the induction and maintenance of tolerance of peripheral antigen. Immunity 1994; 1: 155–166.
105. Finck B., Linsley P., Wofsy D. Treatment of murine lupus with CTLA4Ig. Science 1994; 265: 1225–1227.
106. Bolling S., Turka L., Wei R., Linsely P., Thompson C., Lin H. Inhibition of B7-induced CD28 T-cell activation with CTLA4Ig prevents cardiac allograft rejection; evidence for costimulation. Transplantation of tolerance induced by CTLA-41g. Transplantation 1994; 57: 1701–1706.
108. Lenschow D., Ho S., Sattar H., Rhee L., Gray G., Nabavi N., Herold K, Bluestone J. Differential effects of anti-B7-1 and anti-B7-2 monoclonal antibody treatment on the development of diabetes in the nonobese diabetic mouse. J of Exp Medicine 1995; 181: 1145–1155.
109. Durie F., Fava R., Foy T., Aruffo A., Ledbetter J., Noelle R, Prevention of collagen-induced arthritis with an antibody to gp39, the Ligand for CD40. Science 1993; 261: 1328–1330.
110. Mohan C., Shi Y., Laman J., Datta S. Interaction between CD40 and its ligand gp39 in the development of murine lupus nephritis. The American Association of Immunologists 1995; 154: 1470–1480.
111. Gin H., Cadic C., Baquey C., Dupuy B. Peritoneal exudates from microencapsulated rat islets of Langerhans xenografted mice presenting characteristics of potentially cytotoxic non-specific inflammation. J of Microencapsulation 1992; 9: 489–494.
112. Clayton H., London N., Colloby P., Bell P., James R. The effect of capsule composition on the biocompatibility of alginate-poly-l-lysine capsules. J. Microencapsulation 1991; 8: 221–233.
113. Soon-Shiohg P., Oterlie M., Skjak-Braek G., Smidsrod O., Heintz R., Lanza R. P., Espevik T. An immunologic basis for the fibrotic reaction to implanted microcapsules. Transpl Proc 1991; 23: 758–759.
114. DeVos P., Wolters G., Vanschilfgaarde R. Possible relationship between fibrotic overgrowth of alginate-polysine-alginate microencapsulated pancreatic islets and the microcapsule integrity. Transp Proc 1994; 26: 782–783.
115. Chang T. Artificial cells in immobilization biotechnology. Art Cells & Immob Biotech 1992; 20: 1121–1143.
116. Lum Z., Tai I., Krestow M., Norton J., Vacek I., Sun A. Prolonged reversal of diabetic state in NOD mice by xenografts of microencapsulated rat islets. Diabetes 1991; 40: 1511–1516.
117. Chicheportiche D., Reach G. In vitro kinetics of insulin release by microencapsulated rat islets: effects of the size of the microcapsules. Diabetologia 1988; 31: 54–57.
118. Weber C., Constanzo M., Kredun S., D'Agati V. Causes of destruction of microencapsulated islet grafts: Characteristics of a 'double-wall' poly-l-lysine-alginate microcapsule. Diabetes, Nutrition and Metabolism 1993; 1: 167–171.
119. Vanenbossche G., Van Oostveldt P., Demeester J., Remon J. The molecular weight cut-off of microcapsules is determined by the reaction between alginate and polylysine. Biotechnology and Bioengineering 1993; 42: 381–386.
120. Linderman G., Adams J., Cory S., Harris A. B-lymphoid to granulocytic with during hematopoiesis in a transgenic mouse strain. Immunity 1994; 1: 517–527.
121. Takeuchi T., Lowry R., Konoieczny B. Heart allografts in murine systems. Transplantation 1992; 53: 1281–1294.
122. Ravetch J., Kinet J. J Ann Rev Immunol 1993; 9: 457–492.
123. Takai T., Li M., Sylvestre D., Clynes R., Ravetch J. FcR y chain deletion results inpleiotrophic effector cell defects. Cell 1994; 76: 519–529.
124. Krych M., Atkinson J., Holers v. Complement receptors. Curr Opin Immunol 1992; 4: 8–13.
125. Frank M., Fries: The role of complement in inflammation and phagocytosis. Immunol Today 1991; 12: 322–326.
126. Whiteley P. J., Jensen P. E. Pierce C. W., Abruzzini A. F., Kapp J. A. Helper T-cell clones that recognize autologous insulin are stimulated in nonresponder mice by pork insulin. Proc Natl Acad Sci USA 1998; 85: 2723–2727.
127. Jensen P. E., Kapp J. A. Stimulation of helper T cells and dominant suppressor T cells that recognize autologous insulin. J Mol Cell Immunol 1985; 2: 133–133.
128. Poindexter N. J., Landon C., Whiteley P. J., Kapp J. A. Comparison of the T cells receptors on insulin-specific hybridomas from insulin transgenic and nontransgenic mice. Loss of a subpopulation of self-reactive clones. J Immunol 1992; 149: 38–44.
129. Ke Y., Li Y., Kapp J. A. ovalbumin injected with complete Freund's adjuvant stimulates cytolytic responses. Eur J Immunol 1995; 25: 549–553.
130. Seder R., Paul W. Acquisition of lymphokine-producing phenotype by CD $4^+$ T cells. Annu Rev Immunology 1994; 12: 635–635.
131. Beckerman K., Rogers H., Corbett J., Schreiber R., McDaniel M., Unanue E. Release of nitric oxide during the T-cell independent pathway of macrophage activation J Immunol 1993; 150: 888–895.
132. Weinberg B., Granger D., Pisetsky D., Seldin M., Misukonis M., Mason N., Pippen A., Ruiz P., Wood E., Gilkeson G. The role of nitric oxide in the pathogenesis of spontaneous murine autoimmune disease: Increased nitric oxide production and nitric oxide synthase expression in MRL-1pr/1pr mice, and reduction of spontaneous glomerulonephritis and arthritis by orally administered $N^g$-monomethyl-l-arginine. J. Exp Med 1994; 179: 651–660.
133. Ravetch J. Fc Receptors: Rubor Redux. Cell 1994; 78: 553–560.
134. Unreels J., Scigliano E., Freedman V. Structure and function of human an murine receptors for IgG. Annual Review of Immunology 1988; 6: 251–281.
135. Platt J., Lindman B., Geller R., Noreen H., Swanson J., Dalmasso A., Bach F. The role of natural antibodies in the activation of xenogenic endothelial cells. Transplantation 1991; 52: 1027–1043.
136. Baxter G., Cooke A. Complement lytic activity has no role in the pathogenesis of autoimmune diabetes in NOD mice. Diabetes 1994; 42: 1574–1578.

137. Moses R., Winn H., Auchincloss H. Evidence that multiple defects in cell-surface molecule interactions across species differences are responsible for diminished xenogenic T cell responses. Transplatation 1992; 53: 203–209.

138. Moses R., Pierson R., Winn H., Auchincloss H. Xenogeneic proliferation and lymphokine production are dependent on CD4+ helper T cells and self antigen-presenting cells in the mouse. J Exp Med 1990; 172: 567–575.

139. Hardy M., Lau H., Weber C., Reemtsma K. Pancreatic islet Transplantation; Induction of graft acceptance by ultraviolet irradiation of donor tissue. Ann Surg 1984; 200: 441–450.

140. Sullivan F., Ricordi C., Hauptfeld V., Lacy P. Effect of low-temperature culture and site of transplantation on hamster islet xenografts survival (hamster-to-mouse). Transplatation 1987; 44: 465–468.

141. Hering B., Bretzel R., Federlin K., Horm Metabol Res 1988; 20:537–545.

142. Lacy P., Lacy E., Finke E., Yasunami Y. Diabetes 1982; 31:109–111.

143. Nathan D. NEJM 1993; 328:176–1685.

144. Robertson R. NEJM 1992; 327: 1861–1868.

145. Linsley P. S., Brady W., Umes M., Grosmaire L. S., Damie N. K., Ledbetter J. A. CTLA-4 is a second receptor for the B cell activation antigen B7. J Exp Med 1991; 74: 561–569.

146. Korbutt G. S., Ao Z., Warnock G. L., Flashner M., Rajotte R. V. Successful reversal of diabetes in nude mice by transplantation of microencapsulated procine neonatal islet cell aggregats. Transplantation Proceedings 1995; 27:3212.

147. Korbutt G. S., Ao Z., Warnock G. L., Rajotte R. V. Large-scale isolation of viable porcine neonatal islet cell (NIC) aggregates. Transplantation Proceedings 1995; 27:3267.

Second Series of Experiments

The goal of this study was to clarify the mechanism(s) of destruction of microencapsulated islet xenografts by spontaneously diabetic NOD mice, the best available model of human insulin-dependent diabetes (IDDM). We have found that NOD helper T-cells and MHC both are necessary for destruction of encapsulated islets (30, 31), and we have documented that empty microcapsules are biocompatible in NOD mice (27–29, 31). Encapsulated islet xenografts biopsied at rejection in NOD mice contained abundant pericapsular macrophages and immunoglobulins, with IL-1, TNFα, and IL-4 messenger RNA (13, 28, 29). Therefore, we postulated that NOD rejection was initiated by donor antigens that were secreted from encapsulated islets, and were processed via the MHC class II pathway by host APC. NOD CD4+ T-cells then promoted a Th2 response, with donor islet destruction occurring via cytokine-mediated events.

Involvement of APC in immune responses to islet xenografts was suggested by recent studies of Lenschow et al. (15), who found that blockade of the costimulatory molecule, B7 with the soluble fusion protein, CTLA4-Ig, prolonged human-to-mouse islet xenografts in SZN-diabetic mice. Several studies, in vitro and in vivo, have shown that foreign molecules that interact with the T-cell fall on their own to stimulate naive T-cells to proliferate and may induce antigen-specific anergy. At least one additional (costimulatory) signal is required, and it is delivered by APC. In mice, one such costimulatory pathway involves the interaction of the T-cell surface antigen, CD28 with either one of two ligands, B7-1 and B7-2, on APCs (4, 7, 8, 10, 11, 17, 22). Once this full interaction of T-cells and APC occurs, reexposure of T-cells to the peptide, mitogen, etc., will result in proliferation without costimulation (10).

CTLA-4 is a cell surface protein similar to CD28; however, unlike CD28, CTLA-4 is expressed only on activated T-cells. B7-1 has a higher affinity for CLTA4 than CD28, and it has been suggested that CTLA4 may modulate functions of CD28 (5, 6, 11). CTLA4-Ig is a recombinant soluble fusion protein, with the extracellular binding domain of the CTLA4 molecule and the constant region of the IgGl gene, which inhibits T-lymphocyte responses in mice (9, 14). Administration of CTLA4-Ig to mice induces antigen-specific unresponsiveness (7, 11, 25), and long-term acceptance of murine cardiac allografts (3, 21). In addition, CTLA4-Ig has been reported to reduce the incidence of diabetes in NOD mice (16). We have recently found that murine CTLA4-Ig prolonged survival of encapsulated adult rabbit islets in NOD mice (26).

Materials and Methods

Neonatal porcine islets were isolated from White Landrace pigs and tissue cultured as previously described (12). Approximately 8000 islets were encapsulated in double-wall, Poly-L-lysine-alginate microcapsules and grafted intraperitoneally in NOD or NOD-SCID mice, as previously reported 29, 31). Controls received approximately 8000 unencapsulated neonatal islets grafted beneath the splenic or renal capsule.

Murine CLTA4-Ig, provided by Bristol-Myers-Squibb (P.S.L.) Seattle, Wash., was administered at 200 μg intraperitoneally (i.p.), day zero and then q.o.d. for 21 days, or until graft rejection if that occurred prior to day #21. Graft function was monitored daily by measurement of random blood glucose for 2 wk and then weekly (31). Graft rejection was defined as random blood glucose >250 mg/dL for 2 consecutive days.

Biopsies of long-term functioning peritoneal micro-capsules were done periodically, using metafane anesthesia and a sterile technique. Removal of 100–200 microcapsules allowed histologic light microscopic and insulin immunochemical studies without altering graft-related normoglycemia (31). Statistical differences between groups were assessed by use of Student's t-test and by ANOVA.

Results

Neonatal pig islets are actually dispersed neonatal porcine pancreatic cells that reaggregate in tissue culture to form "islet"-like spheroids with approximately 5–10% beta cells (see FIG. 16), which is significantly higher than the 1–2% beta cell concentration in the adult porcine pancreas. Approximately 30,000–100,000 islets were obtained from each 2–5-day-old neonatal donor pig (see FIG. 14). Neonatal pig islet cells secreted insulin in vitro after microencapsulation (see FIG. 15). Biopsies of these "islets" >100 days following transplantation to streptozotocin-diabetic NOD-Scid mice revealed increased numbers of intensely insulin-positive islet cells in most cell aggregates (FIG. 28). Thus, neonatal pig islets appear to differentiate and divide during the transplant period.

Treatment of NOD mice with CTLA4-Ig significantly prolonged survival of intraperitoneal poly-L-lysine-alginate microencapsulated donor neonatal porcine islet xenografts (CAP/I.P.) in spontaneously diabetic NOD mice, when compared to either islet microencapsulation or NOD CTLA4-Ig treatment alone (Table 7). Biopsies of long-term functioning encapsulated neonatal porcine islets from CTLA4-Ig-treated NOD mice documented intact microcapsules, containing viable donor islets, with many insulin-positive beta cells, and no peri-capsular NOD cellular response (FIG. 29). Biopsies of NODs controls receiving intraperitoneal encapsulated porcine islets, without CTLA4-Ig treatment uniformly showed pericapsular accumulations of macrophages, neutrophils, and lymphocytes, as previously described (2, 20, 24). Biopsies of pancreases from NOD mice in all experimental groups showed absence of beta cells, and occasional accumulations of lymphocytes in perivascular areas.

TABLE 7

Survival of microencapsulated (MC) neonatal porcine islets in NOD mice: Effects of NOD treatment with CTLA4-Ig

| | | | Mean Graft survival (days) | |
|---|---|---|---|---|
| | Technique | Rx. | (n) | x ± SE |
| Pig-NOD | MC/IP | None | 8 | 27 ± 13 | 9, 10, 11, 12, 12, 14, 14, 23, 118[s] |
| Pig-NOD | MC/IP | CTLA4-Ig | 6 | 110 ± 14* | 74[s], 81, 101[s], 108, 137[s], 161[s] |
| Pig-NOD | Splenic | CTLA4-Ig | 3 | 5 ± 1 | 4, 5, 5 |
| Pig-NOD | Splenic | None | 3 | 6 | 5, 6, 7 | i.p. = intraperitoneal;
[s] = sacrifice for biopsy;
*p < 0.001 vs. MC alone;
CTLA4-Ig, 200 μg i.p., q.o.d. × 3 wk.

Discussion

The most important finding of this invention is the synergy of donor islet microencapsulation and NOD CTLA4-Ig treatment in prolonging neonatal porcine islet xenograft survival. Neither CTLA4-Ig, nor encapsulation alone was effective. There is evidence that xeno-recoanition (unlike allorecognition) occurs primarily via the so-called "indirect" antigen presentation pathway, by which host APC present peptides scavenged from extracellular (donor) proteins to host helper T-cells (1, 18, 19, 23). Applicants' recent report, that the host MHC is critical to NOD rejection of encapsulated islet xenografts (30), and applicants' prior observations, that helper NOD T-cells are essential for this response (31), both are consistent with an "indirect" pathway. Applicants' current data suggest that "indirect" antigen presentation may be blocked by CTLA4-Ig in this model of encapsulated islet xenotransplantation.

TABLE 8

Synergy of Neonatal Porcine Islet Microencapsulation and Xenogeneic NOD Mouse Receipient Treatment with CTLA4Ig

| Technique | Rx | (N) | Graft Survival (Days) (x̄ ± SE) |
|---|---|---|---|
| MC/IP | None | 8 | 9, 10, 12, 12, 14, 18, 23, 116 (27± 36) |
| MC/IP | CTLA4Ig | 10 | 61, 74[S], 80[S], 80, 85, 101[S], 108, 137[S], 160[S], 266[S] (115.2 ± 19.3)** |
| MC/IP | CTLA4Ig* | 10 | 12, 32, 55, 63, 75, 78, 83, 103, 239[s], 287[s] (102.7 ± 28.2)** |
| Splenic | CTLA4Ig | 3 | 4, 5, 5 (5 ± 1) |
| Splenic | None | 3 | 5, 6, 7 (6 ± 1) |

[s] = sacrifice;
**p < .003 vs. MC/IP alone;
MC/IP = microencapsulation/intraperitoneal;
CTLA4Ig* = mutant CTLA4Ig, which does not bind complememt.

TABLE 9

| Pig C-Peptide (ng/ml) | |
|---|---|
| Ham's F10 media | 0.225 |
| 24 hr Supe-empty capsules | 0.677 |
| 24 hr Supe-fresh, encapsulated pig islets | 13.469 |
| 24 hr Supe-belly wash, CTLA4Ig*-treated, day #239, with functioning encapsulated pig islets | 10.603 |
| 24 hr Supe, belly wash, rejected pig islets graft | 0.082 |

Supe = supernatant

Conclusions

CTLA4Ig, Microcapsules, and Neonatal Pig Islet Xenografts in NODs

Long-term effect was found with only 21 days of CTLA4Ig. Both wild-type CTLA4Ig and mutant CTLA4Ig* (Y100 F) (which does not bind complement) were effective. (see FIGS. 34–35) There was no toxicity to recipients. There is biopsy proof of long-term graft function. (see FIGS. 30–33) Further proof that long-term grafts are functioning is provided by use of a radio-immunoassay to measure pig insulin (pig C-peptide) as secreted (see Table 9) which is rapidly degraded. Insulin is released by insulin cells that are specific for the pig (pig insulin is detected by the presence of the C-peptide tails). The presence of C-peptide tails in the grafts indicates that the graft is alive and functioning, as exemplified by a long-term graft of 239 days. (see also FIGS. 30–31)

In conclusion, applicants have found that neither microencapsulation nor CTLA4-Ig alone prevent NOD destruction of neonatal porcine islets. However, applicants observed synergy between CTLA4-Ig treatment of NOD recipients and islet encapsulation, with significantly prolonged discordant islet xenograft survival. (see Tables 7 and 8) Because of the availability of large quantities of porcine islets and bioacceptability of the microcapsules and CTLA4-Ig this approach may be clinically relevant (in humans).

References for the Second Series of Experiments
1. Auchincloss, H. *Transplantation* 46:1–20; 1988.
2. Barker, C.; Naji, A. *N. Engl. J. Med.* 327:1861–1868; 1992.
3. Boiling, S.; Turka, L.; Wei, R.; Linsley, P.; Thompson, C.; Lin, H. *Transplantation* xx:?2?413–415; 1994.
4. Galvin, F.; Freeman, G.; Razi-Wolf, Z.; et al. *J. Immunol.* 149:3802–3908; 1992.
5. Gimmi, C.; Freeman, G.; Gribben, J.; Gray, G.; Nadler, L. *Immunoloqy* 90:6586–6590; 1993.
6. Guerder, S.;, Meyerhoff, J.; Flavell, R. *Immunity* 1:155–166; 1994.
7. Harding, F.; McArthur, J,; Gross, J.; Raulet, D.; Allison, J. *Nature* 356:607–609; 1992.
8 Hathcock, K.; Laszio, G.; Dickler, H.; Bradshaw, J.; Linsley, P.; Hodes, R. *Science* 262:905–907; 1993.
9. Hering, B.; Bretzel, R,; Federlin, K. *Horm. Metabol. Res.* 20:537–545; 1988,
10. Janeway, C.; Bottomly, K. *Cell* 76:275–285; 1994.
11. Jenkins, M. *Immunity* 1:443–446; 1994.
12. Korbutt, G. S.: Ao, Z.; Warnock, G. L.; Rajotte, R. V. *Transplant. Proc.* 27:3267; 1995.
13. Krych, M.; Atkinson, J.; Holers, V. *Curr. Opin. Immunol.* 4:8–13; 1992.
14. Lacy, P.; Lacy, E.; Finke. E.; Yasunami, Y. *Diabetes* 31:109–111, 1982.
15. Lenschow, D.; Zeng, Y.; Thistlethwaite, J.; et al. *Science* 257:789–795; 1992.

16. Lenschow, D.; Ho, S.; Sattar. H.; et al. *J. Exp. Med.* 181:1145–1155; 1995.
17. Liu, Y.; Jones, B.; Brady, W.; Janeway, C.; Linsley, P. *Eur. J. Immunol.* 22:2855–1859; 1992.
18. Moses, R.; Pierson, R.; Winn, H.; Auchincloss, H. *J. Exp. Med.* 172:567–575; 1990.
19. Moses, R.; Winn, H.; Auchincloss, H. *Transplantation* 53:203–209; 1992.
20. Nathan, D. *N. Engl. J, Med.* 328:1676–1685; 1993.
21. Pearson, T.; Alexander, D.; Winn, K.; Linsley, P.; Lowry, R.; Larsen, C. *Transplantation* 57:1701–1706; 1994
22. Perrin, P.; Scott, D.; Quigley, L.; et al. *J. Immunol.* 154:1481–1490; 1995.
23. Platt, J., Back, F. *Transplantation* 52:937–947; 1991.
24. Robertson, R. *N. Engl. J. Med.* 327:1861–1868; 1992.
25. Satyaraj, E.; Rath, S.; Bal, V. *J. Immunol.* 155:4669–4675; 1995.
26. Weber, C. I.; Hagler, M. K.; Chryssochoos, J. T.; et al. *Transplant. Proc.* 28:821–823; 1996.
27. Weber, C.; Krekun, S.; Koschitzky, S.; et al. *Transplant Proc.* 23:764–766; 1991.
28. Weber, C.; Price, J.; Costanzo, M.; Becker, A.; Stall, A. *Transplant. Proc.* 26:1116–1119; 1994.
29. Weber, C.; Reemtsma, K.; Lanza, R.; Chick, W., eds. Austin: R. Landes; 1994:59–79.
30. Weber, C.; Tanna, A.; Costanzo, M.; Price, J.; Peterson, L.; Wicker, L. Transplant. Proc. xxx.?3?
31. Weber, C.; Zabinski, S.; Koschitzky, T.; et al. *Transplantation* 49:396–404; 1990.

Third Series of Experiments

T Cell Proliferation and Cytokine Production in Diabetic NOD Mice Transplanted With Encapsulated Porcine Islets.

The goal of these experiments was to develop techniques for transplanting microencapsulated xenogeneic islets as a durable physiologic source of insulin for diabetic patients. In spontaneously diabetic NOD mice, encapsulated neonatal porcine islets plus CTLA4-Ig treatment reversed diabetes for over 100 days, but encapsulated islets without CTLA4-Ig were rejected in about 2 weeks and unencapsulated islets within 1 week. (See FIG. 36)

The proliferative and cytokine responses of T cells from NOD mice transplanted with encapsulated porcine islets were compared. (see FIGS. 37 through 58) Spleen cells (SPC) from rejecting NODs spontaneously proliferated in vitro, whereas SPC from mice with functioning grafts or non-transplanted NODs did not. Islet cells induced no proliferation above background with either normal or transplanted NOD SPC. However, cytokine secretion after stimulation with procine islets was detected. (see FIGS. 39A–53B) SPC from both rejecting and non-rejecting mice secreted IFNγ, IL-10, and TGFβ as well as low levels of IL-2, IL-12 and IL-4 when stimulated with islets. In addition, fluid from peritoneal cavities (the site of transplanted encapsulated islets) contained IFNγ, NO$_2$, IL-12 and high levels of TGF-β. (see FIGS. 41A, 52A, and 58; 48A; and 52A,) By contrast, porcine islets stimulated no cytokine secretion by cells from control NOD mice. (see e.g. FIGS. 41B, 48B, 50B, 51B)

It was a surprise to find no significant differences in islet-induced proliferation or cytokines between NOD mice that rejected or accepted grafts. Therefore, additional cytokines (for example, IL-1 and TNFα) that may be present in rejecting NODs but not in those with functioning grafts will be tested.

Summary

Cytokines in Peritoneal Fluid on Day of Sacrifice

Peritoneal fluid from all transplanted NODs contained: relatively high levels of IFN-γ (500–2500 pg/ml), relatively high levels of IL-12 (50–1000 pg/ml), lower amounts of IL-5, IL-10 and TNF-α (<200 pg/ml), lower amounts of IL-2, IL-4, and TGF-β (<100 pg/ml).

No significant differences were found in cytokines from peritoneal fluid of rejecting and non-rejecting transplanted N00s, with one exception. One rejecting NOD untreated with CTLA4-Ig had very high levels of TNF-α (1400 pg/ml).

No significant differences were found in cytokines from mice given different CTLA4-Ig treatments (none, mutant, or wild type (WT)).

Peritoneal fluid from untransplanted mice (diabetic or normal NODs and BALB/c) did not contain significant levels of any cytokines.

Peritoneal fluid is to be tested for other cytokines, for example IL-1.

Nitric Oxide In Vitro

Nitric oxide was produced in cultured "belly washes" (PECs and encapsulated islets from peritoneal cavities of transplanted mice) from all animals tested.

Culturing spleen cells from transplanted mice with pig islets induced nitric oxide production above background levels.

Only non-rejecting transplanted NODs have been tested for nitric oxide production. Rejecting NODs as well as normal NODs, diabetic NODs, and BALB/c mice must be analyzed for nitric oxide generation by SPC and PECs.

Lymphokines Produced by Spleen Cells

Stimulating spleen cells from control animals (untransplanted normal NODs, diabetic NODs, or BALB/c mice) with pig islets did not induce lymphokines.

However, stimulating spleen cells from control mice with Con A induced relatively high levels of IFN-γ and IL-2, low amounts of IL-10, and no IL-4, IL-5, or TNA-α.

In over 50% of transplanted mice tested, pig islets stimulated IFN-γ secretion by spleen cells in vitro (10 of 17). Four mice (2 rejecting and 2 non-rejecting) produced relatively high IFN-γ (>1000 pg/ml).

Pig islets stimulated lower levels (100–500 pg/ml) of IL-4, IL-10, and TGF-β. In 2 of 17, >100 pg/ml IL-4 was stimulated (both not rejecting). In 5 of 17, >100 pg/ml IL-10 was stimulated (2 not rejecting; 3 rejecting). In 2 of 17, >100 pg/ml TGF-β was stimulated (both not rejecting).

Pig islets stimulated IL-12 secretion by spleen cells from 1 of 17 transplanted mice (not rejecting). Pig islets stimulated IL-2 secretion above background levels in 1 of 17 transplanted mice (not rejecting). Pig islets did not stimulate TNF-α secretion by spleen cells from any transplanted mice.

Lymphokines that are clearly associated with graft rejection have not been identified. No striking differences in lymphokines from mice given different CTLA4-Ig treatment (none, mutant, or WT) was observed.

What is claimed is:

1. A method for inhibiting destruction of a viable transplanted xenogenic cell or tissue by a subject's immune system comprising:
   (a) transplanting the cell or tissue into the subject, wherein the cell or tissue is surrounded by a semipermeable membrane that is impermeable to immunoglobulins; and (b) treating the subject with a prophylactically effective amount of CTLA4 or CTLA4Ig, wherein the cell surrounded by the semipermeable membrane and the CTLA4 or CTLA4Ig have a synergistic effect so as to inhibit the destruction of the transplanted cell or tissue by the subject's immune system.

2. The method of claim 1, wherein the semipermeable membrane comprises polylysine-alginate.

3. The method of claim 1, wherein the semipermeable membrane is a microcapsule.

4. The method of claim 1, wherein the semipermeable membrane is double-walled.

5. The method of claim 1, wherein the subject is a mammal.

6. The method of claim 1, wherein the subject is selected from the group consisting of a cow, a calf, a pig, a sheep, a lamb, a horse, a chicken and a human.

7. The method of claim 6, wherein the subject is a human.

8. The method of claim 1, wherein the xenogeneic donor is a mammal.

9. The method of claim 8, wherein the mammal is selected from the group consisting of a pig, a cow, a calf, a sheep, a lamb and a human.

10. The method of claim 1, wherein the viable cell or tissue secretes a hormone which promotes growth in an animal.

11. The method of claim 1, wherein the viable cell or tissue comprises an endocrine cell or tissue.

12. The method of claim 11, wherein the endocrine cell or tissue is selected from the group consisting of an insulin-producing cell or tissue, an hepatocyte or hepatic tissue, a parathyroid cell or tissue and a pituitary cell or tissue.

* * * * *